(12) United States Patent
Ohmoto et al.

(10) Patent No.: US 8,404,858 B2
(45) Date of Patent: Mar. 26, 2013

(54) AGENT FOR REGENERATION AND/OR PROTECTION OF NERVES

(75) Inventors: Kazuyuki Ohmoto, Osaka (JP); Akihiro Kinoshita, Osaka (JP); Hidekazu Matsuya, Mishima-gun (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 12/944,326

(22) Filed: Nov. 11, 2010

(65) Prior Publication Data

US 2011/0059920 A1  Mar. 10, 2011

Related U.S. Application Data

(63) Continuation of application No. 11/916,374, filed as application No. PCT/JP2006/311084 on Jun. 2, 2006, now Pat. No. 7,863,263.

(30) Foreign Application Priority Data

Jun. 3, 2005 (JP) ................................ 2005-164458

(51) Int. Cl.
    *C07D 277/04* (2006.01)
(52) U.S. Cl. ....................................................... 548/146
(58) Field of Classification Search ................... 548/146
    See application file for complete search history.

(56) References Cited

U.S. PATENT DOCUMENTS

| 6,288,119 | B1 | 9/2001 | Ohuchida |
| 7,402,605 | B2 | 7/2008 | Tani et al. |
| 2005/0020686 | A1 | 1/2005 | Maruyama et al. |
| 2005/0124577 | A1 | 6/2005 | Tani et al. |
| 2006/0109102 | A1 | 5/2006 | Gortz et al. |
| 2007/0129327 | A1 | 6/2007 | Ohmoto et al. |
| 2008/0021021 | A1 | 1/2008 | Okada et al. |
| 2009/0227644 | A1 | 9/2009 | Ohmoto et al. |

FOREIGN PATENT DOCUMENTS

| EP | 0 156 611 | A2 | 10/1985 |
| EP | 1 481 976 | A1 | 12/2004 |
| EP | 1 586 564 | A1 | 10/2005 |
| EP | 1 609 480 | A1 | 12/2005 |
| EP | 1 806 148 | A1 | 7/2007 |
| JP | 11-130678 | A | 5/1999 |
| WO | 2003/009872 | A1 | 2/2003 |
| WO | 03/074483 | A1 | 9/2003 |
| WO | 2004/065365 | A1 | 8/2004 |
| WO | 2004/089411 | A1 | 10/2004 |
| WO | 2005/053707 | A1 | 6/2005 |
| WO | 2005/061492 | A1 | 7/2005 |
| WO | 2006/016689 | A1 | 2/2006 |
| WO | 2006/043655 | A1 | 4/2006 |

OTHER PUBLICATIONS

Stella et al 'Prodrugs: Challenges and Rewards, Part 1' Biotechnology: Pharmaceutical Aspects, p. 24, 2007.*
Vippagunta et al 'Crystalline Solids' Advanced Drug Delivery Reviews, vol. 48, p. 3-26, 2001.*
Supplementary European Search Report dated Feb. 12, 2010 in European Application No. 04819909.5.
Kato et al., "Successful Treatment of Intermittent Claudication Due to Spinal Canal Stenosis Using Beraprost Sodium, a Stable Prostaglandin I2 Analogue," The Journal of Vascular Diseases, vol. 48, No. 5, pp. 457-461 (1997).
Yone et al., "The effect of Lipo prostaglandin E1 on cauda equina blood flow in patients with lumbar spinal canal stenosis: myeloscopic observation," Spinal Cord, vol. 37, No. 4, pp. 269-274 (1999).
Konno et al., "Effects of OP-1206 (Prostaglandin E1) on Nerve-Conduction Velocity in the Dog Cauda Equina Subjected to Acute Experimental Compression," Journal of Spinal Disorders, vol. 9, No. 2, pp. 103-106 (1996).
Orendacova et al., "Gouda equina syndrome," Progress in Neurobiology, vol. 64, No. 6, pp. 613-637 (2001).
Extended European Search Report dated Feb. 2, 2010 in European Application No. 06756919.4.
Israeli Office Action issued in Application No. 187840; dated Mar. 10, 2010.
New Zealand Office Action, Application No. 563863, issued Jul. 1, 2010.
European Office Action, Application No. 06756919.4, issued Jun. 10, 2010.
Russian Office Action, Application No. 2007148992, issued Jun. 23, 2010.
Chinese Office Action, Application No. 2006800286854, issued Jun. 9, 2010.
Bilak et al., "PGE2 Receptors Rescue Motor Neurons in a Model of Amyotrophic Lateral Sclerosis," Annals of Neurology, 2004, vol. 56, No. 2, pp. 240 to 248, full test, particularly, p. 243, left column, line 48 to p. 244, line 11, Fig 3., abstract, lines 1 to 3.
Y. Liu, "Rat Umao Shinkei Appaku Hoko Shogai Model Deno Beraprost Natrium to Limaprostal fadex Tono Hikaku", Basic Pharmacology & Therapeutics, 2002 pp. 875-880, vol. 30, No. 10.
M. Kiriyama, "Ligand binding specificities of the eight types and subtypes of the mouse prostanoid receptors expressed in Chinese hamster ovary cells", 1997, pp. 217-224, vol. 122, No. 2.
H. Kuwada, "Effects of prostaglandin derivatives on changes of gastric mucosal protein contents in ethanol-induced ulcer", Cytoprotection & Biology, 1985, pp. 217-225, vol. 3.
Kiyohiro Tsutsui, "Procylin Naifuku Toya go Soki Shita Livedo Kekkan'en no 1 Rei", The Journal of Medicine, 1994, pp. 611-613, vol. 32, No. 3.
International Search Report (PCT/ISA/210) for PCT/JP04/017961, dated Feb. 1, 2005.

(Continued)

*Primary Examiner* — Brandon Fetterolf
*Assistant Examiner* — Christopher R Stone
(74) *Attorney, Agent, or Firm* — Sughrue Mion, PLLC

(57) ABSTRACT

An EP2 agonist which may have an EP3 agonistic effect has an effect of regenerating and/or protecting nerves, and is therefore useful as a therapeutic agent for a disease of the peripheral nervous system, such as a lower or upper motor neuron disease, a nerve root disease, plexopathy, thoracic outlet compression syndrome, peripheral neuropathy, neurofibromatosis and neuromuscular transmission disease. An EP2 agonist which has an EP3 agonistic effect is a safe and effective agent for the regeneration and/or protection of nerves which has little influence on the circulatory system.

5 Claims, No Drawings

OTHER PUBLICATIONS

European Patent Office, Supplementary Search Report dated Feb. 12, 2010 from the European Patent Office in European application No. 04819909.5.

U.S. Patent Office, Communication dated Sep. 17, 2012, issued in corresponding U.S. Appl. No. 12/889,731.

Jun Han, "Advances in Characterization of Pharmaceutical Hydrates", Trends in Bio/Pharmaceutical Industry, Mar. 2006, 6 pgs total.

* cited by examiner

AGENT FOR REGENERATION AND/OR PROTECTION OF NERVES

The present application is a Continuation of U.S. application Ser. No. 11/916,374 filed Dec. 3, 2007, which is a national stage application of PCT/JP2006/311084 filed Jun. 2, 2006, which claims the benefit of Japanese Patent Application No. 2005-164458 filed Jun. 3, 2005, the disclosures of which are incorporated herein in their entireties by reference.

TECHNICAL FIELD

The present invention relates to an agent for regeneration and/or protection of nerves. More particularly, it relates to an agent for regeneration and/or protection of nerves comprising an EP2 agonist which may have an EP3 agonistic effect.

BACKGROUND OF THE INVENTION

The nervous system is roughly divided into central nervous system and peripheral nervous system, and the peripheral nervous system particularly takes charge of neurotransmission by connecting the brain and spine with somatic peripheries. The peripheral nervous system can be classified into somatic nervous system (cerebrospinal nervous system) and autonomic nerve system. Additionally, the somatic nervous system is divided into cranial nerves and spinal nerves. Also, when the somatic nervous system is functionally classified, those which transmit a neural signal (excitation) generated from a sensory receptor to the central nerves are classified into afferent or sensory nerve fiber, while those which transmit a neural signal directing from the brain and spine toward effector organs such as muscles and glands are classified into efferent or motor nerve fiber. Cranial nerves are peripheral nerves extended from the brain and 12 pairs thereof are known. Some of them consist of sensory nerve fibers; some of them consists of motor nerve fibers; and some of them consists of mixed nerve fibers. Each of the first to twelfth nerve pairs is called olfactory nerve, optic nerve, oculomotor nerve, trochlear nerve, trigeminal nerve, abducens nerve, facial nerve, auditory nerve, glossopharyngeal nerve, vagus nerve, accessory nerve and hypoglossal nerve. Among them, as nerves consisting of the sensory or mixed nerve fibers, olfactory nerve, optic nerve, trigeminal nerve, facial nerve, auditory nerve, glossopharyngeal nerve and vagus nerve are known. The spinal nerves are peripheral nerves extended from the spine and respective 31 pairs are known. Namely, 8 pairs of cervical nerve, 12 pairs of breast nerve, 5 pairs of lumbar nerve, 5 pairs of sacral nerve and a pair of coccyx nerve are known. All of the spinal nerves consist of mixed nerve fibers and contain sensory fibers (dorsal roots) extend to the skin and the like and motor fibers (ventral roots) extend to skeletal muscle.

The sensory nerve fibers, namely sensory nerves, take charge of a function to accurately transfer stimuli such as light, sound, temperature and touch received by sensory receptors such as optic organ, auditory organ, olfactory organ, gustatory organ and the skin to the central nervous system. The neural signals transferred to the central nervous system are finally transferred to each sensory area of the cerebral cortex, for example, visual area, auditory area and the like, and the sensation is normally recognized thereby. However, there is a case in which various neuropathies of these sensory nerves such as cell death and demyelination are induced through damages of axons, myelin sheaths, Schwann cells or the like caused, for example, by viral infection, tumor, cancer, diabetes mellitus, ischemia, injury, compression, drugs, radiotherapy and the like. As a result, since correct neurotransmission is not carried out in a sensory nerve which caused a disorder, for example, diseases such ad hearing loss and neuropathic pain are generated. In addition to these, there is a neuropathy in which not only a specific sensory nerve but also various peripheral nerves including sensory nerves simultaneously undergo damages caused, for example, by metabolic disease, autoimmune disease and the like diseases, injuries, drug intoxication and the like. In this disease, a single nerve, two or more nerves which present in separate regions or a large number of nerves sometimes undergo the disorder simultaneously. Its symptoms are very complex and varied, and include pain, numbness and burning sensation in a peripheral region and proprioceptive sensation reduction, hypopallesthesia, pain (including neuropathic pain), abnormal sensation, cold, heat and the like.

Additionally, the motor unit includes anterior horn cells, efferent axons thereof and all muscle fibers controlled by the axons. It is known that various peripheral nerve system diseases accompanied by motor function disorders including atrophy, weakness or consumption of a muscle (skeletal muscle or the like) are generated when the motor unit undergoes a certain disorder. The peripheral nerve system disease is divided into a neurogenic disease, a myogenic disease and a mixed type disease thereof. Examples of the neurogenic disease include diseases which are generated when any region of from motor nerve cell to neuromuscular junction in motor units undergoes a disorder, and the like. The neurogenic diseases are generated particularly when a cell body, an axon or a neuromuscular junction of the motor unit undergoes a disorder, and their symptoms occur at peripheries of the legs and arms in most cases.

Examples of the peripheral nerve system diseases include lower and upper motor neuron diseases (e.g., amyotrophic lateral sclerosis, paraneoplastic syndrome, progressive bulbar paralysis, progressive muscular atrophy, primary lateral sclerosis, progressive pseudobulbar paralysis, post poliomyelitis syndrome, genetic spinal muscular atrophy (type I spinal muscular atrophy) (Werdnig-Hoffman disease), type II (intermediate) spinal muscular atrophy, type III spinal muscular atrophy (Wohlfart-Kugelberg-Welander disease), (type IV spinal muscular atrophy) and the like); nerve root diseases (e.g., hernia of intervertebral disk, spinal canal stenosis, cervical spondylosis and the like); plexus diseases (e.g., acute brachial plexitis and the like); thoracic outlet compression syndrome; peripheral nerve disorders (e.g., mononeuropathy, multiple mononeuropathy, multiple neuropathy, Guillain-Barre syndrome, genetic neuropathy (e.g., peroneal muscular atrophy (Chalcot-Marie-Tooth disease), hypertrophic interstitial neuropathy (Dejerine-Sottas disease), diabetic peripheral nerve disorders, neurofibromatosis (e.g., peripheral neurofibroma (Recklinghausen disease), central nervefibroma and the like), *Proteus* syndrome and the like) and the like); or neuromuscular transmission diseases (e.g., myasthenia gravis, amyotonia congenita syndrome, Eaton-Lambert syndrome, botulism, systemic tetany syndrome, Isaacs syndrome and the like) and the like.

However, since the aforementioned peripheral nerve system diseases are diseases whose generation mechanisms are unknown or physical injuries of nerves, so that symptomatic therapy is mainly carried out with the aim of improving the symptoms in their treatment. Clinically useful agents applicable to the fundamental therapy by directly acting upon the nerves which underwent disorders are barely known.

On the one hand, prostaglandins have been known as a metabolite in the arachidonate cascade. It has been known that the action has cyto-protective activity, uterine contractive activity, a pain-inducing effect, a promoting effect on digestive peristalsis, an awakening effect, a suppressive effect on gastric acid secretion, hypotensive activity and diuretic activity and the like.

A recent study has proved existence of various PGE subtype receptors possessing a different physiological or pharmacological role from each other. At present, four receptor subtypes are known and they are called EP1, EP2, EP3, and EP4 (Negishi M., et al., *J. Lipid Mediators Cell Signaling*, 12, 379-391 (1995)).

It is described that a prostaglandin-like compound described in EP860430A1 has an EP2 agonistic effect and is useful for a prevention and/or a treatment of immune diseases, asthma, abnormal bone formulation, neuron cell death, liver damage, premature birth, abortion or retinal neuropathy such as glaucoma etc (Patent Reference 1).

It is described that a prostaglandin-like compound described in WO98/34916 has an EP3 agonistic effect and is useful for a prevention and/or a treatment of liver diseases, kidney diseases, pancreatitis or myocardial infarction etc (Patent Reference 2).

It is described that a prostaglandin-like compound described in WO03/074483 has an EP2 agonistic effect and is useful for a prevention and/or a treatment of immune diseases, allergic diseases, neuronal cell death, dysmenorrhea, premature birth, abortion, baldness, retinal neuropathy, erectile dysfunction, arthritis, pulmonary injury, pulmonary fibrosis, pulmonary emphysema, bronchitis, chronic obstructive pulmonary disease, hepatic injury, acute hepatitis, liver cirrhosis, shock, nephritis, renal failure, circulatory diseases, systemic inflammatory response syndrome, sepsis, hemophagocytosis syndrome, macrophage activation syndrome, still disease, Kawasaki disease, burn, systemic granuloma, ulcerative colitis, Crohn disease, hypercytokinemia at dialysis, multiple organ failure, or bone diseases etc (Patent Reference 3).

It is described in WO04/089411 that the combination of the compound which has an EP2 agonistic effect and the compound which has EP3 agonistic effect is useful for spinal canal stenosis (Patent Reference 4).

It is described in WO05/053707 that the prostaglandin-like compound is useful as the agent for increasing cauda equina blood flow (Patent Reference 5).

On the one hand, it is known that EP2 receptor, which is the subtype of PGE$_2$ receptor, relates to the protecting effect of nerves in cerebra (Non-Patent Referent 1).

However, it is neither indicated nor described that an EP2 agonist which may have an EP3 agonistic effect has the regenerating or the protecting effect of peripheral nerves.
[Patent Reference 1] EP860430A1
[Patent Reference 2] WO98/34916
[Patent Reference 3] WO03/074483
[Patent Reference 4] WO04/089411
[Patent Reference 5] WO05/053707
[Non-Patent Referent 1] Nurobiology of Disease, 24, 1, 257-268 (2004)

DISCLOSURE OF THE INVENTION

Problems to be Solved by the Invention

Great concern has been directed toward a highly safe and effective nerve regenerative and/or protective agent which directly acts on disordered nerves in peripheral nerve system diseases.

Means for Solving the Problems

The present inventors studied eagerly, and as a result, found that an EP2 agonist which may have an EP3 agonistic effect has the regenerating and the protecting effect of nerves. Furthermore, the present inventors found that the EP2 agonist which may have the EP3 agonistic effect has little influence on the blood pressure and the ventricular rate and the like, a little influence on the circulatory system and can be a high safe and effective agent for the prevention and/or treatment of a disease of the peripheral nervous system, and completed the present invention.

That is to say, the present invention relates to:

1. an agent for regeneration and/or protection of nerves comprising an EP2 agonist which may have an EP3 agonistic effect;

2. the agent for the regeneration and/or protection of nerves described in the above 1, comprising an EP2 agonist having an EP3 agonistic effect;

3. the agent described in the above 2, wherein the EP2 agonist having an EP3 agonistic effect is a compound represented by formula (I):

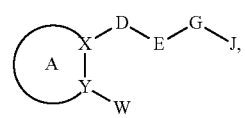

wherein ring A is a 5 or 6-membered ring which may comprise 1 to 3 hetero atom(s) selected from nitrogen, oxygen and sulfur in addition to X and Y, and furthermore may have a substituent(s), X and Y are each independently nitrogen or carbon, D is hydrocarbon which may have a substituent(s), E is a bond, oxygen or optionally oxidized sulfur, G is a bond, hydrocarbon which may have a substituent(s) or hetero ring which may have a substituent(s), J is an acidic group which may be protected, W is hydrocarbon which may have a substituent(s), a salt thereof, an N-oxide thereof, an S-oxide thereof, a solvate thereof or a prodrug thereof, or a cyclodextrin clathrate thereof;

4. the agent described in the above 3, wherein the compound represented by formula (I) is a compound represented by formula (I-1):

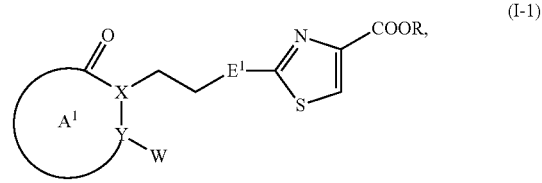

wherein ring A$^1$ is 5 or 6 membered ring which may comprise 1 to 3 hetero atom(s) selected from nitrogen, oxygen and sulfur in addition to X and Y, and may have more substituent(s), E$^1$ is oxygen or optionally oxidized sulfur, R is hydrogen or C1-8 aliphatic hydrocarbon, and the other symbols have the same meanings as those described in the above 3;

5. the agent described in the above 4 wherein the compound represented by formula (I-1) is a compound represented by formula (I-5):

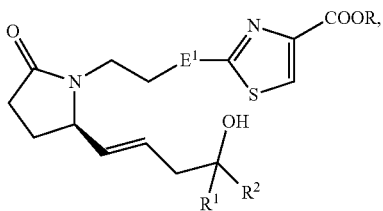
(I-5)

wherein R¹ is hydrogen or C1-4 aliphatic hydrocarbon group, R² is hydrocarbon group which may have a substituent(s), ⌁ is β-configuration, and the other symbols have the same meanings as those described in the above 4;

6. a medicament combined an EP2 agonist having an EP3 agonistic effect, with one or more selected from an EP2 agonist and an EP3 agonist;

7. the agent described in the above 1, wherein the regeneration and/or protection of nerves is a prevention and/or a treatment for a disease of the peripheral nervous system;

8. a medicament comprising an EP2 agonist which may have an EP3 agonistic effect, and one or more species selected from prostaglandins, prostaglandin derivatives, nonsteroidal anti-inflammatory drugs, vitamins, muscle relaxants, antidepressants, nitric oxide synthase inhibitors, aldose reductase inhibitors, poly ADP-ribose polymerase inhibitors, excitatory amino acid receptor antagonists, radical scavengers, astrocyte modulators, phosphodiesterase inhibitor and immunosuppressive agent in combination;

9. a method for the regeneration and/or protection of nerves, which comprises administering to a mammal an effective amount of an EP2 agonist which may have an EP3 agonistic effect;

10. a use of an EP2 agonist which may have an EP3 agonistic effect, for the manufacture of an agent for regeneration and/or protection of nerves;

11. a compound represented by formula (I-2):

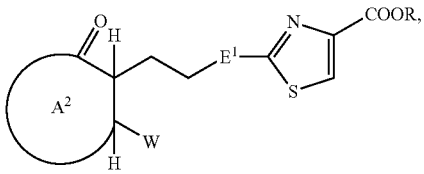
(I-2)

wherein ring A² is a 5 or 6-membered ring which may comprise 1 to 3 hetero atom(s) selected from nitrogen, oxygen and sulfur, and may have more substituent(s), and the other symbols have the same meanings as those described in the above 4, excluding 2-[(2-{(1R,2R)-2-[(1E,3S,5S)-3-hydroxy-5-methyl-1-nonenyl]-5-oxocyclopentyl}ethyl)sulfanyl]-1,3-thiazole-4-carboxylic acid, 2-[(2-{(1R,2R)-2-[(1E,3R)-3-hydroxy-4,4-dimethyl-1-octenyl]-5-oxocyclopentyl}ethyl)sulfanyl]-1,3-thiazole-4-carboxylic acid, 2-[(2-{(1R,2R)-2-[(1E)-4-hydroxy-4-methyl-1-nonenyl]-5-oxocyclopentyl}ethyl)sulfanyl]-1,3-thiazole-4-carboxylic acid, 2-[(2-{(1R,2R)-2-[(1E)-5-cyclohexyl-4-hydroxy-4-methyl-1-pentenyl]-5-oxocyclopentyl}ethyl)sulfanyl]-1,3-thiazole-4-carboxylic acid and 2-[(2-{(1R,2R)-2-[(1E)-5-cyclohexyl-4-hydroxy-4-methyl-1-pentenyl]-5-oxocyclopentyl}ethyl)sulfonyl]-1,3-thiazole-4-carboxylic acid, a salt thereof, an N-oxide thereof, an S-oxide thereof, a solvate thereof or a prodrug thereof, or a cyclodextrin clathrate thereof;

12. the compound described in the above 11, which is represented by formula (I-3):

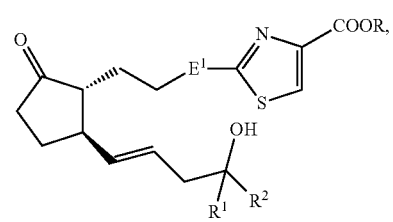
(I-3)

wherein ⌁ is α-configuration, and the other symbols have the same meanings as those described in the above 4 and above 5;

13. the compound described in the above 12, wherein R¹ is hydrogen or C1-4 alkyl group, R² is C1-8 aliphatic hydrocarbon group which may have a substituent(s), or (C3-8 cycloalkyl)-(C1-4 aliphatic hydrocarbon) group which may have a substituent(s), 14. the compound described in the above 11, which is selected from 2-[(2-{(1R,2R)-2-[(1E,4S)-5-cyclohexyl-4-hydroxy-4-methyl-1-penten-1-yl]-5-oxocyclopentyl}ethyl)thio]-1,3-thiazole-4-carboxylic acid (compound 17), 2-[(2-{(1R,2R)-2-[(1E)-4-hydroxy-4,8-dimethyl-1,7-nonadien-1-yl]-5-oxocyclopentyl}ethyl)thio]-1,3-thiazole-4-carboxylic acid (compound 18-5), 2-[(2-{(1R,2R)-2-[(1E)-4-hydroxy-4,7-dimethyl-1,7-octadien-1-yl]-5-oxocyclopentyl}ethyl)thio]-1,3-thiazole-4-carboxylic acid (compound 18-6), 2-[(2-{(1R,2R)-2-[(1E,4S)-4-hydroxy-4-methyl-1-nonen-1-yl]-5-oxocyclopentyl}ethyl)thio]-1,3-thiazole-4-carboxylic acid (compound 17-1), 2-[(2-{(1R,2R)-2-[(1E)-4-hydroxy-4-methyl-1,7-octadien-1-yl]-5-oxo cyclopentyl}ethyl)thio]-1,3-thiazole-4-carboxylic acid (compound 32), 2-[(2-{(1R,2R)-2-[(1E,4R)-4-hydroxy-4,8-dimethyl-1-nonen-5-yn-1-yl]-5-oxocyclopentyl}ethyl)thio]-1,3-thiazole-4-carboxylic acid (compound 25-2a), 2-[(2-{(1R,2R)-2-[(1E,4S)-4-hydroxy-4,7-dimethyl-1-octen-1-yl]-5-oxocyclopentyl}ethyl)thio]-1,3-thiazole-4-carboxylic acid (compound 25-3a), 2-[(2-{(1R,2R)-2-[(1E,4S)-6-cyclobutyl-4-hydroxy-4-methyl-1-hexen-1-yl]-5-oxocyclopentyl}ethyl)thio]-1,3-thiazole-4-carboxylic acid (compound 25-4a), 2-[(2-{(1R,2R)-2-[(1E,4R)-4-hydroxy-4-methyl-1-decen-5-yn-1-yl]-5-oxocyclopentyl}ethyl)thio]-1,3-thiazole-4-carboxylic acid (compound 25-5a), 2-[(2-{(1R,2R)-2-[(1E,4S)-4-hydroxy-7-methyl-1,7-octadien-1-yl]-5-oxocyclopentyl}ethyl)thio]-1,3-thiazole-4-carboxylic acid (compound 31a) and 2-[(2-{(1R,2R)-2-[(1E,4S)-6-cyclobutyl-4-hydroxy-1-hexen-1-yl]-5-oxocyclopentyl}ethyl)thio]-1,3-thiazole-4-carboxylic acid (compound 3'-1);

15. 2-[(2-{(2R)-2-[(1E)-5-cyclohexyl-4-hydroxy-4-methyl-1-pentenyl]-5-oxo-1-pyrrolidinyl}ethyl)thio]-1,3-thiazole-4-carboxylic acid (compound 24-1), 2-[(2-{(2R)-2-[(1E)-4-hydroxy-4,7-dimethyl-1-octen-1-yl]-5-oxo-1-pyrrolidinyl}ethyl)thio]-1,3-thiazole-4-carboxylic acid (compound 24-2), 2-[(2-{(2R)-2-[(1E)-4-hydroxy-4-methyl-1-decen-5-yn-1-yl]-5-oxo-1-pyrrolidinyl}ethyl)thio]-1,3-thiazole-4-carboxylic acid (compound 24-3), 2-[(2-{(2R)-2-[(1E,4R)-4-hydroxy-4-methyl-1-decen-5-yn-1-yl]-5-oxo-1-pyrrolidinyl}ethyl)thio]-1,3-thiazole-4-carboxylic acid (compound 34), 2-[(2-{(2R)-2-[(1E,4S)-4-hydroxy-4,7-dimethyl-1-octen-1-yl]-5-oxo-1-pyrrolidinyl}ethyl)thio]-1,3-thiazole-4-carboxylic acid (compound 34-1) or 2-[(2-{(2R)-2-[(1E,4S)-4-hydroxy-4,7-dimethyl-1,7-octadien-1-yl]-5-oxo-1-pyrrolidinyl}ethyl)thio]-1,3-thiazole-4-carboxylic acid (compound 34-2), a salt thereof, an N-oxide thereof, an S-oxide thereof, a solvate thereof or a prodrug thereof, or a cyclodextrin clathrate thereof;

16. an agent for the regeneration and/or protection of nerves, or an agent to increase cauda equina blood flow comprising the compound which is represented by formula (I-2) or the compound described in the above 15, the salt thereof, the N-oxide thereof, the S-oxide thereof, the solvate thereof or the prodrug thereof, or the cyclodextrin clathrate thereof;

17. the agent described in the above 16, which is a preventive and/or a therapeutic agent for spinal canal stenosis and/or cervical vertebra symptom.

The "5 or 6 membered ring" represented by ring A may comprise 1 to 3 hetero atom(s) selected from nitrogen, oxygen and sulfur in addition to X and Y. The "5 or 6 membered ring" represented by ring A is, for example, "5 or 6 membered mono-carbocyclic ring" or "5 or 6 membered mono-heterocyclic ring" and the like. The "5 or 6 membered mono-carbocyclic ring" includes, for example, cyclopentane, cyclohexane, cyclopentene, cyclohexene, cyclopentadiene, cyclohexadiene or benzene and the like. The "5 or 6 membered mono-heterocyclic ring", which is a 5 or 6 membered mono-heterocyclic ring comprising 1 to 5 hetero atom(s) selected from nitrogen, oxygen and sulfur, includes, for example, pyrrole, imidazole, triazole, tetrazole, pyrazole, pyridine, pyrazine, pyrimidine, pyridazine, triazine, furan, thiophene, oxazole, isoxazole, thiazole, isothiazole, furazan, oxadiazole, thiadiazole, pyran, thiopyran, oxazine, oxadiazine, thiazine, thiadiazine, pyrroline, imidazoline, triazoline, tetrazoline, pyrazoline, dihydropyridine, tetrahydropyridine, dihydropyrazine, tetrahydropyrazine, dihydropyrimidine, tetrahydropyrimidine, dihydropyridazine, tetrahydropyridazine, tetrahydrotriazine, dihydrofuran, dihydropyran, dihydrothiophene, dihydrothiopyran, dihydrooxazole, dihydroisoxazole, dihydrothiazole, dihydroisothiazole, dihydrofurazan, dihydrooxadiazole, dihydrooxazine, dihydrooxadiazine, dihydrothiadiazole, dihydrothiazine, dihydrothiadiazine, pyrrolidine, imidazolidine, triazolidine, tetrazolidine, pyrazolidine, piperidine, piperazine, perhydropyrimidine, perhydropyridazine, tetrahydrofuran, tetrahydropyran, perhydrooxepine, tetrahydrothiophene, tetrahydrothiopyran, tetrahydrooxazole (oxazolidine), tetrahydroisoxazole (isoxazolidine), tetrahydrothiazole (thiazolidine), tetrahydroisothiazole (isothiazolidine), tetrahydrofurazan, tetrahydrooxadiazole (oxadiazolidine), tetrahydrooxazine, tetrahydrooxadiazine, tetrahydrothiadiazole (thiadiazolidine), tetrahydrothiazine, tetrahydrothiadiazine, morpholine, thiomorpholine or oxathiane and the like. A 5 or 6 membered bridged bi-heterocyclic ring such as (1R,5S)-3-azabicyclo[3.1.0]hexane ring is also included in "5 or 6 membered ring".

The ring A is preferably, cyclopentane, cyclopentene, pyrrolidine, imidazolidine, tetrahydrooxazole, tetrahydrothiazole or (1R,5S)-3-azabicyclo[3.1.0]hexane ring and the like, more preferably cyclopentane or pyrrolidine and the like.

The ring A may have an optional substituent(s). 1 to 5 substituent(s), preferably 1 to 3 one(s), may be substituted at replaceable positions. When the number of substituents is two or more, each substituent may be the same or different. When the number of substituents of ring A is two or more, for example, two substituents of ring A taken together with atom on ring A may form a ring. The formed ring includes C3-7 cycloalkane (such as cyclopropane, cyclobutane, cyclopentane, cyclohexane, cycloheptane etc).

The substituent of the ring A includes, for example, (1) hydrocarbon group which may have a substituent(s), (2) heterocyclic group which may have a substituent(s), (3) amino which may have a protecting group(s), (4) C1-4 alkylsulfonyl such as methylsulfonyl and ethylsulfonyl etc, (5) phenylsulfonyl, (6) halogen atom such as fluorine, chlorine, bromine and iodine, (7) carboxyl, (8) cyano, (9) nitro, (10) oxo, (11) thioxo, (12) hydroxy which may have a protecting group(s), (13) mercapto which may have a protecting group(s), (14) carbamoyl which may have a substituent(s), (15) sulfamoyl which may have a substituent(s), (16) alkoxycarbonyl (e.g., C1-6 alkoxycarbonyl such as methoxycarbonyl, ethoxycarbonyl and tert-butoxycarbonyl etc), (17) sulfo (—SO$_3$H), (18) sulfino, (19) phosphono, (20) amidino, (21) imino, (22) —B(OH)$_2$ or (23) C1-6 acyl such as formyl, acetyl, propionyl and butylyl and the like.

The "hydrocarbon group" in the "(1) hydrocarbon group which may have a substituent(s)" as the substituent of the ring A includes, for example, a straight or a branched aliphatic hydrocarbon group; cyclic hydrocarbon group; C7-16 alalkyl such as benzyl and phenylethyl; (C3-8 cycloalkyl)-(C1-8 aliphatic hydrocarbon) group such as cyclohexylmethyl, cyclohexylethyl, cyclohexylpropyl, 1-methyl-1-cyclohexylmethyl, cyclobutylmethyl, cyclobutylethyl, cyclobutylpropyl, cyclobutylpropenyl, cyclobutylbutenyl, cyclopentylmethyl, cyclopentylethyl, cyclopentylpropyl, cyclopentylpropenyl, cyclopropylmethyl and cyclopropylethyl and the like.

The "straight or branched aliphatic hydrocarbon group" includes, for example, "C1-12 aliphatic hydrocarbon group". The "C1-12 aliphatic hydrocarbon group" includes, for example, C1-12 alkyl such as methyl, ethyl, propyl, isopropyl, butyl, sec-butyl, tert-butyl, pentyl, hexyl, heptyl, octyl, nonyl, decyl, undecyl and dodecyl etc; C2-12 alkenyl such as vinyl, propenyl, butenyl, pentenyl, hexenyl, heptenyl, octenyl, nonenyl, decenyl, undecenyl, dodecenyl, butadienyl, pentadienyl, hexadienyl, heptadienyl, octadienyl, nonadienyl, decadienyl, undecadienyl, dodecadienyl, hexatrienyl, heptatrienyl, octatrienyl, nonatrienyl, decatrienyl, undecatrienyl and dodecatrienyl etc; C2-12 alkynyl such as ethynyl, propynyl, butynyl, pentynyl, hexynyl, heptynyl, octynyl, nonynyl, decynyl, undecynyl, dodecynyl, butadiynyl, pentadiynyl, hexadiynyl, heptadiynyl, octadiynyl, nonadiynyl, decadiynyl, undecadiynyl, dodecadiynyl, hexatriynyl, heptatriynyl, octatriynyl, nonatriynyl, decatriynyl, undecatriynyl or dodecatriynyl and the like.

The "cyclic hydrocarbon" in the "cyclic hydrocarbon group" includes "saturated cyclic hydrocarbon" or "unsaturated cyclic hydrocarbon" and the like. The "saturated cyclic hydrocarbon" includes, for example, "3-15 membered saturated cyclic hydrocarbon". The "3-15 membered saturated cyclic hydrocarbon" includes, for example, 3-15 membered cycloalkane such as cyclopropane, cyclobutane, cyclopentane, cyclohexane, cycloheptane, cyclooctane, cyclononane, cyclodecane, cycloundecane, cyclododecane, cyclotridecane, cyclotetradecane and cyclopentadecane etc; or 3-15 membered saturated polycyclic hydrocarbon such as perhydropentalene, perhydroazulene, perhydroindene, perhydronaphthalene, perhydroheptalene, spiro[4.4]nonane, spiro[4.5]decane, spiro[5.5]undecane, bicyclo[2.2.1]heptane, bicyclo[3.1.1]heptane, bicyclo[2.2.2]octane, adamantane or noradamantane and the like.

The "unsaturated cyclic hydrocarbon" includes, for example, "3-15 membered unsaturated cyclic hydrocarbon". The "3-15 membered unsaturated cyclic hydrocarbon" includes, for example, 3-8 membered cycloalkene such as cyclopentene, cyclohexene, cycloheptene, cyclooctene, cyclopentadiene, cyclohexadiene, cycloheptadiene and cyclooctadiene etc; 3-15 membered aromatic hydrocarbon such as benzene, azulene, naphthalene, phenanthrene and anthracene etc; 3-15 membered unsaturated polycyclic hydrocarbon such as pentalene, indene, indane, dihydronaphthalene, teterahydronaphthalene, heptalene, biphenylene, as-indacene, s-indacene, acenaphthene, acenaphthylene, fluorene, phenalene, bicyclo[2.2.1]hept-2-ene, bicyclo[3.1.1]hept-2-ene or bicyclo[2.2.2]oct-2-ene and the like.

The "substituent" in the "hydrocarbon group which may have a substituent(s)" as the substituent of the ring A includes, for example, (1) hydrocarbon group (here, this "hydrocarbon group" has the same meaning as the "hydrocarbon group" in the "(1) hydrocarbon group which may have a substituent(s)" as the substituent of the ring A described above) which may have a substituent(s) (e.g., amino, sulfo, halogen atom, carboxy, cyano, nitro, oxo, thioxo, hydroxy, C1-8 alkoxy (e.g., methoxy, ethoxy, propoxy, isopropoxy, butoxy, isobutoxy, sec-butoxy, tert-butoxy, cyclohexylmethyloxy, benzyloxy etc), trifluoromethyl, trifluoromethoxy etc), (2) heterocyclic ring (here this "heterocyclic ring" has the same meaning as the "heterocyclic ring" in the "(2) heterocyclic ring which may have a substituent(s)" as the substituent of the ring A described below) which may have a substituent(s) (e.g., hydrocarbon group (here, this "hydrocarbon group" has the same meaning as the "hydrocarbon group" in the "(1) hydrocarbon group which may have a substituent(s)" as the substituent of the ring A described above), amino, sulfo, halogen atom, carboxy, cyano, nitro, oxo, thioxo, hydroxy, methoxy, trifluoromethyl, trifluoromethoxy, acetyl etc), (3) amino, (4) C1-6 acylamino such as acetylamino and propionylamino and the like, (5) primary or secondary amino substituted by hydrocarbon group such as methylamino, ethylamino, propylamino, isopropylamino, butylamino, dimethylamino, diethylamino, cyclohexylamino, 1-carbamoyl-2-cyclohexylethylamino, N-butyl-N-cyclohexylmethylamino, phenylamino and butoxyphenylamino (this "hydrocarbon group" has the same meaning as the "hydrocarbon group" in "(1) hydrocarbon group which may have a substituent(s)" as the substituent of the ring A described above and may be substituted by C1-4 alkoxy (e.g., methoxy, ethoxy, propoxy, isopropoxy, butoxy, isobutoxy, sec-butoxy, tert-butoxy etc), oxo, amino, carbamoyl etc), (6) C1-4 alkylsulfonylamino such as methylsulfonylamino and ethylsulfonylamino and the like, (7) phenylsulfonylamino, (8) C1-4 alkylsulfonyl such as methylsulfonyl and ethylsulfonyl and the like, (9) phenylsulfonyl, (10) halogen atom (fluorine, chlorine, bromine, iodine), (11) carboxy, (12) cyano, (13) nitro, (14) oxo, (15) thioxo, (16) hydroxy, (17) C1-8 alkoxy such as methoxy, ethoxy, propoxy, isopropoxy, butoxy, isobutoxy, sec-butoxy, tert-butoxy, cyclohexylmethyloxy or benzyloxy (here, the alkoxy may be substituted by halogen atom etc), (18) C3-8 cycloalkyloxy such as cyclohexyloxy (the C3-8 cycloalkyloxy may be substituted by halogen atom etc), (19) phenoxy which may be substituted by methyl and halogen atom and the like, (20) mercapto, (21) C1-4 alkylthio such as methylthio, ethylthio, propylthio, isopropylthio, butylthio and tert-butylthio and the like, (22) phenylthio, (23) carbamoyl, (24) aminocarbonyl substituted by hydrocarbon group such as N-butylaminocarbonyl, N-cyclohexylmethylaminocarbonyl, N-butyl-N-cyclohexylmethylaminocarbonyl, N-cyclohexylaminocarbonyl and phenylaminocarbonyl (this "hydrocarbon group" has a same meaning as the "hydrocarbon group" in the "(1) hydrocarbon group which may have a substituent(s)" as the substituent of the ring A described above), (25) sulfamoyl, (26) aminosulfonyl substituted by hydrocarbon group such as methylaminosulfonyl (this "hydrocarbon group" has a same meaning as the "hydrocarbon group" in the "(1) hydrocarbon group which may have a substituent(s)" as the substituent of the ring A described above), (27) aminosulfonyl which is substituted by the hydrocarbon group substituted by amino such as dimethylaminoethylaminosulfonyl and dimethylaminopropylaminosulfonyl (here, this "hydrocarbon group" has a same meaning as the "hydrocarbon group" in the "(1) hydrocarbon group which may have a substituent(s)" as the substituent of the ring A described above), (28) C1-6 alkoxycarbonyl such as methoxycarbonyl, ethoxycarbonyl and tert-butoxycarbonyl and the like, (29) sulfo ($—SO_3H$), (30) sulfino, (31) phosphono, (32) amidino, (33) imino, (34) $—B(OH)_2$, (35) C1-4 alkylsulfinyl such as methylsulfinyl and ethylsulfinyl and the like, (36) C1-6 acyl such as formyl, acetyl, propionyl and butylyl and the like, (37) benzoyl, (38) hydroxyimino, or (39) alkyloxyimino such as methyloxyimino and ethyloxyimino and the like. The "hydrocarbon group which may have a substituent(s)" may have 1 to 5 substituent(s) selected from (1) to (39) described above. When the number of substituents is two or more, each substituent may be the same or different. Moreover, for example, two substituents taken together with carbon on hydrocarbon group may form a ring.

The "heterocyclic ring" in "(2) heterocyclic ring which may have a substituent(s)" as the substituent of the ring A includes, for example, mono-, bi- or tri-heterocyclic ring which may be comprising 1 to 7 hetero atom(s) selected from nitrogen, oxygen and sulfur. The "heterocyclic ring" includes, for example, the "3-15 membered unsaturated mono-, bi- or tri-heterocyclic ring", the "3-15 membered saturated mono-, bi- or tri-heterocyclic ring" and the like.

The "3-15 membered unsaturated mono-, bi- or tri-heterocyclic ring" includes, for example, aromatic mono-heterocyclic ring such as pyrrole, imidazole, triazole, tetrazole, pyrazole, pyridine, pyrazine, pyrimidine, pyridazine, triazine, furan, thiophene, oxazole, isoxazole, thiazole, isothiazole, furazan, oxadiazole and thiadiazole and the like, aromatic fused heterocyclic ring such as indole, isoindole, benzofuran, isobenzofuran, benzothiophene, isobenzothiophene, indazole, quinoline, isoquinoline, purine, phthalazine, pteridine, naphthyridine, quinoxaline, quinazoline, cinnoline, benzoxazole, benzothiazole, benzimidazole, benzofurazan, benzothiadiazole, benztriazole, carbazole, β-carboline, acridine, phenazine, dibenzofuran, dibenzothiophene, phenanthridine, phenanthroline or perimidine and the like, non-aromatic unsaturated heterocyclic ring such as azepine, diazepine, pyran, oxepine, thiopyran, thiepine, oxazine, oxadiazine, oxazepine, oxadiazepine, thiazine, thiadiazine, thiazepine, thiadiazepine, indolizine, dithianaphthalene, quinolizine, chromene, benzoxepine, benzoxazepine, benzoxadiazepine, benzothiepine, benzothiazepin, benzothiadiazepine, benzoazepine, benzodiazepine, xanthene, phenothiazine, phenoxazine, phenoxathiin, thianthrene, pyrroline, imidazoline, triazoline, tetrazoline, pyrazoline, dihydropyridine, tetrahydropyridine, dihydropyrazine, tetrahydropyrazine, dihydropyrimidine, tetrahydropyrimidine, dihydropyridazine, tetrahydropyridazine, tetrahydrotriazine, dihydroazepine, tetrahydroazepine, dihydrodiazepine, tetrahydrodiazepine, dihydrofuran, dihydropyran, dihydrooxepine, tetrahydrooxepine, dihydrothiophene, dihydrothiopyran, dihydrothiepine, tetrahydrothiepine, dihydrooxazole, dihydroisoxazole, dihydrothiazole, dihydroisothiazole, dihydrofurazan, dihydrooxadiazole, dihydrooxazine, dihydrooxadiazine, dihydrooxazepine, tetrahydrooxazepine, dihydrooxadiazepine, tetrahydrooxadiazepine, dihydrothiadiazole, dihydrothiazine, dihydrothiadiazine, dihydrothiazepine, tetrahydrothiazepine, dihydrothiadiazepine, tetrahydrothiadiazepine, indoline, isoindoline, dihydrobenzofuran, dihydroisobenzofuran, dihydrobenzothiophene, dihydroisobenzothiophene, dihydroindazole, dihydroquinoline, tetrahydroquinoline, dihydroisoquinoline, tetrahydroisoquinoline, dihydrophthalazine, tetrahydrophthalazine, dihydronaphthyridine, tetrahydronaphthyridine, dihydroquinoxaline, tetrahydroquinoxaline, dihydroquinazoline, tetrahydroquinazoline, dihydrocinnoline, tetrahydrocinnoline, benzoxathiane, dihydrobenzooxazine, dihydrobenzothiazine, pyrazinomorpholine, dihydrobenzooxazole, dihydrobenzothiazole, dihydro benzimidazole, dihydrobenzoazepine, tetrahydrobenzoazepine, dihydrobenzodiazepine, tetrahydrobenzodiazepine, benzodioxepane, dihydrobenzoxazepine, tetrahydrobenzoxazepine, dihydrocarbazole, tetrahydrocarbozole, dihydro-β-carboline, tetrahydro-β-carboline, dihydroacridine, tetrahydroacridine, dihydrodibenzofuran, dihydrodibenzothiophene, tetrahydro dibenzofuran, tetrahydrodibenzothiophene, dioxaindane, benzodioxane, chromane, benzodithiolane, benzodithiane, 6,7,8,9-tetrahydro-5H-pyrido[4',3':4,5]pyrrolo[2,3-b]pyridine, 2,3,4,5-tetrahydro-1H-pyrido[4,3-b]indole or 6,7,8,9-tetrahydro-5H-pyrido[3',4':4,5]pyrrolo[2,3-b]pyridine and the like. Moreover, the "3-15 membered saturated mono-, bi- or tri-heterocyclic ring" includes, for example, aziridine, azetidine, pyrrolidine, imidazolidine, triazolidine, tetrazolidine, pyrazolidine, piperidine, piperazine, perhydropyrimidine, perhydropyridazine, perhydroazepine, perhydrodiazepine, perhydroazocine, oxirane, oxetane, tetrahydrofuran, tetrahydropyran, perhydrooxepine, thiirane, thietane, tetrahydrothiophene, tetrahydrothiopyran, perhydrothiepine, tetrahydrooxazole (oxazolidine), tetrahydroisoxazole (isooxazolidine), tetrahydrothiazole (thiazolidine), tetrahydroisothiazole (isothiazolidine), tetrahydrofurazan, tetrahydrooxadiazole (oxadiazolidine), tetrahydrooxazine, tetrahydrooxadiazine, perhydrooxazepine, perhydrooxadiazepine, tetrahydrothiadiazole (thiadiazolidine), tetrahydrothiazine, tetrahydrothiadiazine, perhydrothiazepine, perhydrothiadiazepine, morpholine, thiomorpholine, oxathiane, perhydrobenzofuran, perhydroisobenzofuran, perhydrobenzothiophene, perhydroisobenzothiophene, perhydroindazole, perhydroquinoline, perhydroisoquinoline, perhydrophthalazine, perhydronaphthyridine, perhydroquinoxaline, perhydroquinazoline, perhydrocinnoline, perhydrobenzooxazole, perhydrobenzothiazole, perhydrobenzimidazole, perhydrocarbazole, perhydro-β-carboline, perhydroacridine, perhydrodibenzofuran, perhydrodibenzothiophene, dioxolane, dioxane, dithiolane or dithiane and the like.

The "substituent" in the "(2) heterocyclic ring which may have a substituent(s)" as the substituent of the ring A includes, for example, hydrocarbon group (This "hydrocarbon group" has a same meaning as the "hydrocarbon group" in the "(1) hydrocarbon group which may have a substituent(s)" as the substituent of the ring A described above), amino, sulfo, halogen atom, carboxyl, cyano, nitro, oxo, thioxo, hydroxyl, methoxy, trifluoromethyl, trifluoromethoxy or acetyl group and the like. The "(2) heterocyclic ring which may have a substituent(s)" may have 1 to 5 substituent(s) selected from the "substituent" described above. When the number of substituents is two or more, each substituent may be the same or different.

The "protecting group" in the "(3) amino group which may have a protecting group(s)" as the substituent of the ring A includes, for example, hydrocarbon group, sulfo group or sulfonyl group binding with hydrocarbon group which may have a substituent(s) and the like. Here the "hydrocarbon group which may have a substituent(s)" has a same meaning as the "(1) hydrocarbon group which may have a substituent(s)" as the substituent of the ring A described above. The "(3) amino group which may have a protecting group(s)" may have 1 or 2 protecting group(s) selected from the "protecting group" described above. When the number of protecting groups is two, each protecting group may be the same or different.

The "protecting group" in the "(12) hydroxyl group which may have a protecting group(s)" or the "(13) mercapto group which may have a protecting group(s)" as the substituent of the ring A includes, for example, hydrocarbon group which may have a substituent(s) and the like. Here the "hydrocarbon group which may have a substituent(s)" has a same meaning as the "(1) hydrocarbon group which may have a substituent(s)" as the substituent of the ring A described above.

The "substituent" in the "(14) carbamoyl group which may have a substituent(s)" or the "(15) sulfamoyl group which may have a substituent(s)" as the substituent of the ring A includes, for example, hydrocarbon group which may have a substituent(s) and the like. Here the "hydrocarbon group which may have a substituent(s)" has a same meaning as the "(1) hydrocarbon group which may have a substituent(s)" as the substituent of the ring A described above.

The substituent of the ring A includes preferably C1-4 alkyl group such as methyl, ethyl, propyl and butyl, oxo, hydroxyl or halogen atom.

The "5 or 6 membered ring" represented by a ring $A^1$ may comprise 1 to 3 hetero atom(s) selected from nitrogen, oxygen and sulfur in addition to X and Y.

The "5 or 6 membered ring" represented by the ring $A^1$ includes, for example, "5 or 6 membered mono-carbocyclic ring" or "5 or 6 mono-heterocyclic ring" and the like. The "5 or 6 membered mono-carbocyclic ring" includes, for example, cyclopentane, cyclohexane, cyclopentene, cyclohexene, cyclopentadiene or cyclohexadiene and the like. The "5 or 6 mono-heterocyclic ring" includes, for example, pyrroline, imidazoline, triazoline, tetrazoline, pyrazoline, tetrahydropyridine, tetrahydropyrazine, tetrahydropyrimidine, tetrahydropyridazine, tetrahydrotriazine, dihydrofuran, dihydropyran, dihydrothiophene, dihydrothiopyran, dihydroisoxazole, dihydroisothiazole, dihydrooxazine, dihydrooxadiazine, dihydrothiazine, dihydrothiadiazine, pyrrolidine, imidazolidine, triazolidine, tetrazolidine, pyrazolidine, piperidine, piperazine, perhydropyrimidine, perhydropyridazine, tetrahydrofuran, tetrahydropyran, perhydrooxepine, tetrahydrothiophene, tetrahydrothiopyran, tetrahydrooxazole (oxazolidine), tetrahydroisoxazole (isooxazolidine), tetrahydrothiazole (thiazolidine), tetrahydroisothiazole (isothiazolidine), tetrahydrofurazan, tetrahydrooxadiazole (oxadiazolidine), tetrahydrooxazine, tetrahydrooxadiazine, tetrahydrothiadiazole (thiadiazolidine), tetrahydrothiazine, tetrahydrothiadiazine, morpholine, thiomorpholine or oxathiane and the like. Moreover, a 5 or 6 membered bridged bi-heterocyclic ring such as (1R,5S)-3-azabicyclo[3.1.0]hexane is also included in "5 or 6 membered ring".

Moreover, the ring $A^1$ may have 1 to 3 optional substituent(s) in addition to a substituent (e.g., oxo) represented by formula (I-1). This optional substituent may be substituted at the replaceable positions of the ring $A^1$. When the number of substituents is two or more, each substituent may be the same or different. Moreover, when the number of substituents in the ring $A^1$ is two or more, for example, two substituents of ring $A^1$ taken together with atom on the ring $A^1$ may form a ring. The formed ring includes, for example, C3-7 cycloalkyl group (e.g. cyclopropyl, cyclobutyl, cyclopentyl, cyclohexyl, cycloheptyl) and the like. The substituent of the ring $A^1$ includes, for example, the substituent described as the substituent of the ring A described above.

The ring $A^1$ is preferably, for example, cyclopentane, cyclopentene, pyrrolidine, imidazolidine, tetrahydrooxazole, tetrahydrothiazole or (1R,5S)-3-azabicyclo[3.1.0]hexane etc, more preferably, cyclopentane or pyrrolidine and the like.

The substituent aside from the substituent represented by formula (I-1) of the ring $A^1$ is preferably C1-4 alkyl group such as methyl, ethyl, propyl and butyl, hydroxyl or halogen atom.

The "5 or 6 membered ring" represented by ring $A^2$ may comprise 1 to 3 hetero atom(s) selected from nitrogen, oxygen and sulfur.

The "5 or 6 membered ring" represented by ring $A^2$ includes, for example, "5 or 6 membered mono-carbocyclic ring" or "5 or 6 mono-heterocyclic ring" and the like. The "5 or 6 membered mono-carbocyclic ring" includes, for example, cyclopentane, cyclohexane, cyclopentene, cyclohexene, cyclopentadiene or cyclohexadiene and the like. The "5 or 6 mono-heterocyclic ring" includes, for example, pyran, thiopyran, oxazine, thiazine, pyrroline, pyrazoline, dihydropyridine, tetrahydropyridine, dihydropyrimidine, tetrahydropyrimidine, dihydropyridazine, tetrahydropyridazine, tetrahydrotriazine, dihydrofuran, dihydropyran, dihydrothiophene, dihydrothiopyran, dihydroisoxazole, dihydroisothiazole, dihydrooxazine, dihydrothiazine, pyrrolidine, pyrazolidine, piperidine, perhydropyrimidine, perhydropyridazine, tetrahydrofuran, tetrahydropyran, tetrahydrothiophene, tetrahydrothiopyran, tetrahydroisoxazole (isooxazolidine), tetrahydroisothiazole (isothiazolidine), tetrahydrooxazine or tetrahydrothiazine and the like.

Moreover, the ring $A^2$ may have 1 to 3 optional substituent(s) in addition to a substituent (e.g., oxo) represented by formula (I-2). This optional substituent may be substituted at the replaceable positions of the ring $A^2$. When the number of substituents is two or more, each substituent may be the same or different. Moreover, when the number of substituents of the ring $A^2$ is two or more, for example, two substituents of ring $A^2$ taken together with atom on the ring $A^2$ may form a ring. The formed ring includes, for example, C3-7 cycloalkyl group (e.g., cyclopropyl, cyclobutyl, cyclopentyl, cyclohexyl, cycloheptyl) and the like. The substituent aside from the substituent represented by formula (I-2) of the ring $A^2$ includes, for example, the substituent described as the substituent of the ring A described above.

The ring $A^2$ is preferably, for example, cyclopentane or cyclopentene.

The substituent aside from the substituent represented by formula (I-2) of the ring $A^2$ is preferably C1-4 alkyl group such as methyl, ethyl, propyl and butyl, hydroxyl or halogen atom.

The "hydrocarbon group" in the "hydrocarbon group which may have a substituent(s)" represented by D and G includes, for example, a divalent straight or branched aliphatic hydrocarbon group and the like. The "divalent straight or branched aliphatic hydrocarbon group" includes, for example, "C1-8 divalent aliphatic hydrocarbon group" and the like. The "C1-8 divalent aliphatic hydrocarbon group" includes, for example, C1-8 alkylene such as methylene, ethylene, propylene, isopropylene, butylene, sec-butylene, tert-butylene, pentylene, hexylene, heptylene or octylene, C2-8 alkenylene such as vinylene, propenylene, butenylene, pentenylene, hexenylene, heptenylene, octenylene, butadienylene, pentadienylene, hexadienylene, heptadienylene, ocatadienylene, hexatrienylene, heptatrienylene or octatrienylene, C2-8 alkynylene such as ethynylene, propynylene, butynylene, pentynylene, hexynylene, heptynylene, octynylene, butadiynylene, pentadiynylene, hexadiynylene, heptadiynylene, octadiynylene, hexatriynylene, heptatriynylene or octatriynylene and the like. This "hydrocarbon group" may substituted by the "substituent" in the "(1) hydrocarbon group which may have a substituent(s)" as the substituent of the ring A described above.

D is preferably, for example, C1-6 alkylene or C2-6 alkenylene and the like.

The "heterocyclic ring which may have a substituent(s)" represented by G has a same meaning as the "(2) heterocyclic ring which may have a substituent(s)" as the substituent of the ring A described above. The "heterocyclic ring which may have a substituent(s)" represented by G includes preferably, for example, 5 or 6 membered mono-heterocyclic ring (This "5 or 6 membered mono-heterocyclic ring" has a same meaning as the "5 or 6 membered mono-heterocyclic ring" in the ring A described above), and more preferably,

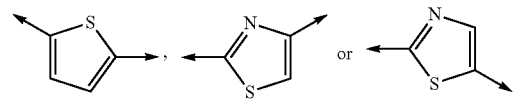

(wherein the arrow is a binding part of E to J) and the like.

The "optionally oxidized sulfur" represented by E, $E^1$ and $E^2$ includes, for example, —S—, —SO— or —SO$_2$—.

E, $E^1$ and $E^2$ are preferably optionally oxidized sulfur, and are more preferably —S— or —SO$_2$—.

The "acidic group" in the "acidic group which may be protected" represented by J means the "acidic group" which may be protected by a "protecting group". Examples of the "acidic group" include carboxy (—COOH), sulfo (—SO$_3$H), sulfino (—SO$_2$H) and sulfonamide (—SO$_2$NH$_2$ or —NR$^{101}$SO$_3$H(R$^{101}$ is hydrogen or hydrocarbon group which may have a substituent(s). Here the "hydrocarbon group which may have a substituent(s)" represents the "(1) hydrocarbon group which may have a substituent(s)" as the substituent of the ring A described above.)), phosphono (—PO(OH)$_2$), phenol (—C$_6$H$_4$OH) or the various types of Brønsted acid such as a nitrogen-containing ring residue having hydrogen from which can be removed as proton. The "Brønsted acid" means a substance which gives hydrogen ion to other substance. Examples of the "nitrogen-containing ring residue having hydrogen from which can be removed as proton" include

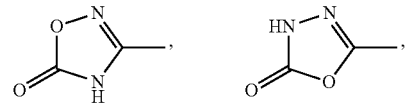

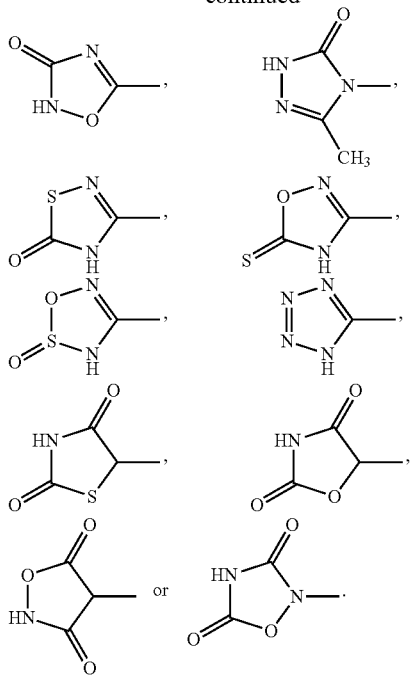

An "acidic group" is preferably, for example, carboxy and the like.

Moreover, the "protecting group" includes hydrocarbon group which may have a substituent(s), amino group which may have a protecting group(s), hydroxyl group which may have a protecting group(s) and the like. Here, the "hydrocarbon group which may have a substituent(s)", the "amino group which may have a protecting group(s)" and the "hydroxyl group which may have a protecting group(s)" have same meanings as the "(1) hydrocarbon group which may have a substituent(s)", the "(3) amino group which may have a protecting group(s)" and the "(12) hydroxyl group which may have a protecting group(s)" as the substituent of the ring A described above respectively. The "protecting group" includes preferably the "hydrocarbon group which may have a substituent(s)", and specifically, for example, methyl, ethyl, propyl, isopropyl, butyl or tert-butyl and the like.

J includes preferably, for example, carboxy group which may have a protecting group(s), more preferably —COOR (wherein R represents hydrogen or C1-8 aliphatic hydrocarbon group) and more preferably —COOH.

The "C1-8 aliphatic hydrocarbon group" represented by R includes C1-8 alkyl group such as methyl, ethyl, propyl, isopropyl, butyl, sec-butyl, tert-butyl, pentyl, hexyl, heptyl or octyl group and the like, C2-8 alkenyl group such as vinyl, propenyl, butenyl, pentenyl, hexenyl, heptenyl, octenyl, butadienyl, pentadienyl, hexadienyl, heptadienyl, octadienyl, hexatrienyl, heptatrienyl or octatrienyl and the like, C2-8 alkynyl group such as ethynyl, propynyl, butynyl, pentynyl, hexynyl, heptynyl, octyny, butadiynyl, pentadiynyl, hexadiynyl, heptadiynyl, octadiynyl, hexatriynyl, heptatriynyl or octatriynyl and the like.

The "hydrocarbon group which may have a substituent(s)" represented by W has a same meaning as the "(1) hydrocarbon group which may have a substituent(s)" as the substituent of the ring A described above.

W is preferably, for example,

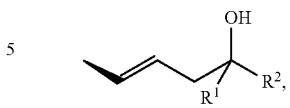

wherein $R^1$ is hydrogen or C1-4 aliphatic hydrocarbon group, $R^2$ is hydrocarbon group which may have a substituent(s), is β-configuration.

The C1-4 aliphatic hydrocarbon group represented by $R^1$ includes, for example, C1-4 alkyl group such as methyl, ethyl, propyl, isopropyl, butyl, sec-butyl or tert-butyl and the like; C2-4 alkenyl group such as vinyl, propenyl, butenyl or butadienyl and the like; C2-4 alkynyl group such as ethynyl, propynyl or butynyl and the like.

$R^1$ is preferably hydrogen or C1-4 aliphatic hydrocarbon group and the like, and is specifically, for example, hydrogen, methyl and ethyl and the like.

The "hydrocarbon group which may have a substituent(s)" represented by $R^2$ has a same meaning as the "(1) hydrocarbon group which may have a substituent(s)" as the substituent of the ring A described above.

$R^2$ includes preferably C1-8 aliphatic hydrocarbon group which may have a substituent(s) (the "C1-8 aliphatic hydrocarbon group" depends in the definition of "C1-12 aliphatic hydrocarbon group" defined as the "hydrocarbon group" in the "(1) hydrocarbon group which may have a substituent(s)" as the substituent of the ring A described above, and the number of carbon can select 1 to 8 one(s)), the 3 to 8 membered saturated cyclic hydrocarbon group which may have a substituent(s) (the "3 to 8 membered saturated cyclic hydrocarbon group" depends in the definition of the "3 to 15 membered saturated cyclic hydrocarbon group" defined as the "hydrocarbon group" in the "(1) hydrocarbon group which may have a substituent(s)" as the substituent of the ring A described above, and the membered number of the ring can select 3 to 8 one(s)), phenyl which may have a substituent(s), or (C3-8 cycloalkyl)-(C1-4 aliphatic hydrocarbon) group which may have a substituent(s) (here, the "C3-8 cycloalkyl" includes cyclopropyl, cyclobutyl, cyclopentyl, cyclohexyl, cycloheptyl or cyclooctyl, the "C1-4 aliphatic hydrocarbon group" includes methyl, ethyl, propyl or butyl), more preferably C1-8 aliphatic hydrocarbon group, or (C3-8 cycloalkyl)-(C1-4 aliphatic hydrocarbon) group which may have a substituent(s). The "substituent" in "hydrocarbon group which may have a substituent(s)" as $R^2$ includes preferably, (1) the cyclic hydrocarbon group which may have a substituent(s) (e.g., C1-4 alkyl group, amino, sulfo, halogen atom, carboxyl, cyano nitro, oxo, thioxo, hydroxyl, methoxy, trifluoromethyl, trifluoromethoxy and acetyl and the like), (2) the heterocyclic group which may have a substituent(s) (e.g., C1-4 alkyl group, amino, sulfo, halogen, carboxyl, cyano, nitro, oxo, thioxo, hydroxyl, methoxy, trifluoromethyl, trifluoromethoxy and acetyl and the like), (10) halogen atom (fluorine, chlorine, bromine, iodine), (11) carboxyl, (14) oxo, (16) hydroxyl, (17) C1-8 alkoxy group such as methoxy, ethoxy, propoxy, isopropoxy, butoxy, isobutoxy, sec-butoxy, tert-butoxy, cyclohexylmethyloxy and benzyloxy, (here, the alkoxy group may be substituted by such as halogen atom), (18) C3-8 cycloalkyloxy group such as cyclohexyloxy (the cycloalkyloxy group may be substituted by such as halogen atom), (19) the phenoxy group which may be substituted by methyl and halogen atom and the like, (28) C1-6 alkoxycarbonyl group such as methoxycarbonyl, ethoxycarbonyl and tert-butoxycarbonyl and the like, (36) C1-6 acyl group such as formyl, acetyl, propionyl and butyryl and the like, or (37) benzoyl.

In the present description, an EP2 agonist which may have an EP3 agonistic effect is a compound which may have an EP3 agonistic effect other than an EP2 agonistic effect, includes an EP2 agonist which does not have an EP3 agonistic effect and an EP2 agonist which has an EP3 agonistic effect, and is preferably an EP2 agonist which has an EP3 agonistic effect.

Moreover, the agent for regeneration and/or protection of nerves comprising an EP2 agonist which may have an EP3 agonistic effect in the present invention (hereinafter, abbreviated as the agent of the present invention) may be used by combining one or more (i) EP2 agonist(s) which may have an EP3 agonistic effect, with one or more agonist(s) selected from (ii) EP2 agonist and (iii) EP3 agonist. The (i) EP2 agonist which may have an EP3 agonistic effect described above is preferably an EP2 agonist which has an EP3 agonistic effect. The (ii) EP2 agonist described above is preferably a compound acting on EP2 selectively, which may or may not have an EP3 agonistic effect. The (iii) EP3 agonist described above is preferably a compound acting on EP3 selectively, which may or may not have an EP2 agonistic effect. For example, one or more (i) EP2 agonist(s) which may have an EP3 agonistic effect, one or more (ii) EP2 agonist(s) and/or one or more (iii) EP3 agonist(s) may be contained within a same pharmaceutical, one or more (i) EP2 agonist(s) which may have an EP3 agonistic effect, one or more (ii) EP2 agonist(s) and/or one or more (iii) EP3 agonist(s) are made a separate pharmaceutical and administered, and in other words may take a configuration of a combined medication. This combined medication includes simultaneous administration, and dosage by temporal difference. The dosage by temporal difference may be administered, for example, the (i) EP2 agonist which may have an EP3 agonistic effect first, and the (ii) EP2 agonist and/or the (iii) EP3 agonist later. It may be administered, the (ii) EP2 agonist and/or the (iii) EP3 agonist first, and the (i) EP2 agonist which may have an EP3 agonistic effect later. Each administered method may be the same or different. Moreover, one or more (i) EP2 agonist(s) which may have an EP3 agonistic effect, one or more (ii) EP2 agonist(s) and/or one or more (iii) EP3 agonist(s) may be contained within a same pharmaceutical.

Moreover, the (i) EP2 agonist which may have an EP3 agonistic effect, the (ii) EP2 agonist and the (iii) EP3 agonist include all a compound which is found newly in future as well as a known compound.

The (ii) EP2 agonist includes, for example, the compounds described in EP860430A1, WO99/33794, EP974580A1, WO95/19964, U.S. Pat. No. 5,698,598, U.S. Pat. No. 6,376,533, WO98/28264, WO99/19300, EP0911321A1, WO98/58911, WO2003/074483, WO2004/078103, WO2005/012232 and ONO-8815Ly, AH-13205, CP-533536, Butaprost, Rioprost, Misoprostol or AY23626 and the like.

The (iii) EP3 agonist includes, for example, the compounds described in WO98/34916, JP07-233145, JP10-168056, JP11-012249, WO99/25358, JP7-215929, JP8-239356, WO97/05091, and TEI-3356, M&B-28767, GR63799X, SC-46275, Enprostil or Sulprostone and the like.

An EP2 agonist which has an EP3 agonistic effect includes, for example, a compound represented by formula (I):

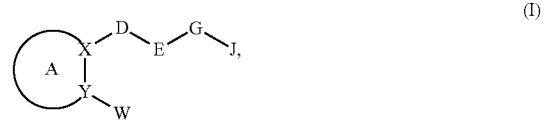

wherein all symbols have the same meanings as described above, a salt thereof, an N-oxide thereof, an S-oxide thereof, a solvate thereof or a prodrug thereof, or a cyclodextrin clathrate thereof.

The compound represented by formula (I) includes preferably the compound represented by formula (I-1):

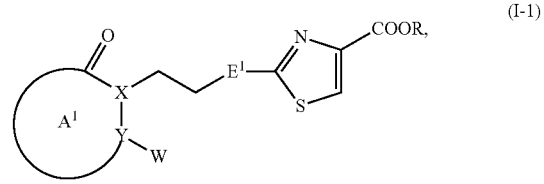

wherein the ring $A^1$ is 5 or 6 membered ring which may comprise 1 to 3 hetero atom(s) selected from nitrogen, oxygen and sulfur in addition to X and Y, and furthermore may have a substituent(s), $E^1$ is oxygen or optionally oxidized sulfur, R is C1-8 aliphatic hydrocarbon group, and the other symbols have the same meanings as those described above, more preferably the compound represented by formula (I-2):

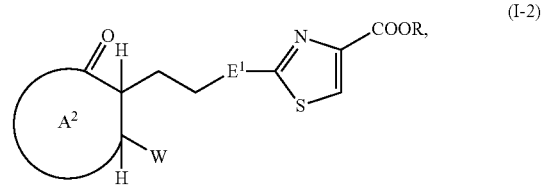

wherein the ring $A^2$ is 5 or 6 membered ring which may comprise 1 to 3 hetero atom(s) selected from nitrogen, oxygen and sulfur, and furthermore may have a substituent(s), and the other symbols have the same meanings as those described above, more preferably the compound represented by formula (I-3):

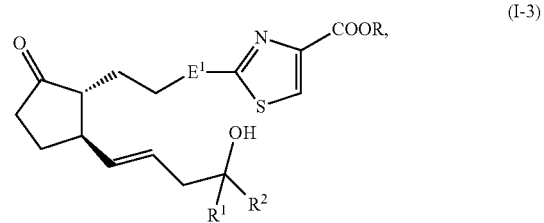

wherein $R^1$ is hydrogen or C1-4 aliphatic hydrocarbon group, $R^2$ is hydrocarbon group which may have a substituent(s), ﹏ is α-configuration, ╱ is β-configuration, and the other symbols have the same meanings as those described above, and the like.

Moreover, the compound represented by formula (I-3) includes more preferably the compound represented by formula (I-4):

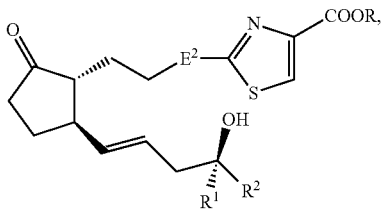

(I-4)

wherein E² is optionally oxidized sulfur, and the other symbols have the same meanings as those described above.

Moreover, formula (I-1) includes preferably the compound represented by formula (I-5):

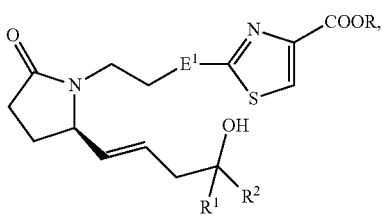

(I-5)

wherein all symbols have the same meanings as those described above.

The compound represented by formula (I) includes preferably the compound described in Examples, a salt thereof, an N-oxide thereof, an S-oxide thereof, a solvate thereof or a prodrug thereof, or a cyclodextrin clathrate thereof and the like, more preferably 2-[2-{(1R,2R)-2-[(1E,4S)-5-cyclohexyl-4-hydroxy-4-methyl-1-penten-1-yl]-5-oxocyclopentyl}ethyl)thio]-1,3-thiazole-4-carboxylic acid (compound 17), 2-[2-{(1R,2R)-2-[(1E,4S)-4-hydroxy-4-methyl-1-nonen-1-yl]-5-oxocyclopentyl}ethyl)thio]-1,3-thiazole-4-carboxylic acid (compound 17-1), 2-[(2-{(1R,5R)-2-oxo-5-[(1E)-8,8,8-trifluoro-4-hydroxy-4-methyl-1-octenyl]cyclopentyl}ethyl)thio]-1,3-thiazole-4-carboxylic acid (compound 18-1), 2-[(2-{(1R,2R)-2-[(1E)-5-cyclopentyl-4-hydroxy-4-methyl-1-pentenyl]-5-oxocyclopentyl}ethyl)thio]-1,3-thiazole-4-carboxylic acid (compound 18-2), 2-[(2-{(1R,2R)-2-[(1E)-8-fluoro-4-hydroxy-4-methyl-1-octen-1-yl]-5-oxocyclopentyl}ethyl)thio]-1,3-thiazole-4-carboxylic acid (compound 18-3), 2-[(2-{(1R,2R)-2-[(1E)-4-hydroxy-4,8-dimethyl-1-nonen-1-yl]-5-oxocyclopentyl}ethyl)thio]-1,3-thiazole-4-carboxylic acid (compound 18-4), 2-[(2-{(1R,2R)-2-[(1E)-4-hydroxy-4,8-dimethyl-1,7-nonadien-1-yl]-5-oxocyclopentyl}ethyl)thio]-1,3-thiazole-4-carboxylic acid (compound 18-5), 2-[(2-{(1R,2R)-2-[(1E)-4-hydroxy-4,7-dimethyl-1,7-octadien-1-yl]-5-oxocyclopentyl}ethyl)thio]-1,3-thiazole-4-carboxylic acid (compound 18-6), 2-[(2-{(1R,2R)-2-[(1E)-4-hydroxy-7-methoxy-4-methyl-1-hepten-1-yl]-5-oxocyclopentyl}ethyl)thio]-1,3-thiazole-4-carboxylic acid (compound 18-10), 2-[(2-{(1R,2R)-2-[(1E)-9-fluoro-4-hydroxy-4-methyl-1-nonen-1-yl]-5-oxocyclopentyl}ethyl)thio]-1,3-thiazole-4-carboxylic acid (compound 18-12), 2-[(2-{(2R)-2-[(1E)-5-cyclohexyl-4-hydroxy-4-methyl-1-pentenyl]-5-oxo-1-pyrrolidinyl}ethyl)thio]-1,3-thiazole-4-carboxylic acid (compound 24-1), 2-[(2-{(2R)-2-[(1E)-4-hydroxy-4,7-dimethyl-1-octen-1-yl]-5-oxo-1-pyrrolidinyl}ethyl)thio]-1,3-thiazole-4-carboxylic acid (compound 24-2), 2-[(2-{(1R,2R)-2-[(1E)-4-hydroxy-4-methyl-1,7-octadien-1-yl]-5-oxocyclopentyl}ethyl)thio]-1,3-thiazole-4-carboxylic acid (compound 32), 2-[(2-{(1R,2R)-2-[(1E,4R)-4-hydroxy-4,8-dimethyl-1-nonen-5-yn-1-yl]-5-oxocyclopentyl}ethyl)thio]-1,3-thiazole-4-carboxylic acid (compound 25-2a), 2-[(2-{(1R,2R)-2-[(1E,4S)-4-hydroxy-4,7-dimethyl-1-octen-1-yl]-5-oxocyclopentyl}ethyl)thio]-1,3-thiazole-4-carboxylic acid (compound 25-3a), 2-[(2-{(1R,2R)-2-[(1E,4S)-6-cyclobutyl-4-hydroxy-4-methyl-1-hexen-1-yl]-5-oxocyclopentyl}ethyl)thio]-1,3-thiazole-4-carboxylic acid (compound 25-4a), 2-[(2-{(1R,2R)-2-[(1E,4R)-4-hydroxy-4-methyl-1-decen-5-yn-1-yl]-5-oxocyclopentyl}ethyl)thio]-1,3-thiazole-4-carboxylic acid (compound 25-5a), 2-[(2-{(1R,2R)-2-[(1E,4S)-4-hydroxy-7-methyl-1,7-octadien-1-yl]-5-oxocyclopentyl}ethyl)thio]-1,3-thiazole-4-carboxylic acid (compound 31a), or 2-[(2-{(1R,2R)-2-[(1E,4S)-6-cyclobutyl-4-hydroxy-1-hexen-1-yl]-5-oxocyclopentyl}ethyl)thio]-1,3-thiazole-4-carboxylic acid (compound 31-1) and the like, particularly preferably 2-[(2-{(1R,2R)-2-[(1E,4S)-5-cyclohexyl-4-hydroxy-4-methyl-1-penten-1-yl]-5-oxocyclopentyl}ethyl)thio]-1,3-thiazole-4-carboxylic acid (compound 17), 2-[(2-{(1R,2R)-2-[(1E)-4-hydroxy-4,8-dimethyl-1,7-nonadien-1-yl]-5-oxocyclopentyl}ethyl)thio]-1,3-thiazole-4-carboxylic acid (compound 18-5), 2-[(2-{(1R,2R)-2-[(1E)-4-hydroxy-4,7-dimethyl-1,7-octadien-1-yl]-5-oxocyclopentyl}ethyl)thio]-1,3-thiazole-4-carboxylic acid (compound 18-6), 2-[(2-{(1R,2R)-2-[(1E,4S)-4-hydroxy-4-methyl-1-nonen-1-yl]-5-oxocyclopentyl}ethyl)thio]-1,3-thiazole-4-carboxylic acid (compound 17-1), 2-[(2-{(1R,2R)-2-[(1E)-4-hydroxy-4-methyl-1,7-octadien-1-yl]-5-oxocyclopentyl}ethyl)thio]-1,3-thiazole-4-carboxylic acid (compound 32), 2-[(2-{(1R,2R)-2-[(1E,4R)-4-hydroxy-4,8-dimethyl-1-nonen-5-yn-1-yl]-5-oxocyclopentyl}ethyl)thio]-1,3-thiazole-4-carboxylic acid (compound 25-2a), 2-[(2-{(1R,2R)-2-[(1E,4R)-4-hydroxy-4,7-dimethyl-1-octen-1-yl]-5-oxocyclopentyl}ethyl)thio]-1,3-thiazole-4-carboxylic acid (compound 25-3a), 2-[(2-{(1R,2R)-2-[(1E,4S)-6-cyclobutyl-4-hydroxy-4-methyl-1-hexen-1-yl]-5-oxocyclopentyl}ethyl)thio]-1,3-thiazole-4-carboxylic acid (compound 25-4a), 2-[(2-{(1R,2R)-2-[(1E,4R)-4-hydroxy-4-methyl-1-decen-5-yn-1-yl]-5-oxocyclopentyl}ethyl)thio]-1,3-thiazole-4-carboxylic acid (compound 25-5a), 2-[(2-{(1R,2R)-2-[(1E,4R)-4-hydroxy-7-methyl-1,7-octadien-1-yl]-5-oxocyclopentyl}ethyl)thio]-1,3-thiazole-4-carboxylic acid (compound 31a) or 2-[(2-{(1R,2R)-2-[(1E,4S)-6-cyclobutyl-4-hydroxy-1-hexen-1-yl]-5-oxocyclopentyl}ethyl)thio]-1,3-thiazole-4-carboxylic acid (compound 31-1) and the like.

Moreover, the compound represented by formula (I) includes preferably 2-{[2-((4S)-4-{(1E,3R)-3-[1-(4-fluorobutyl)cyclobutyl]-3-hydroxy-1-propenyl}-2-oxo-1,3-oxazolidin-3-yl)ethyl]sulfanyl}-1,3-thiazole-4-carboxylic acid (hereinafter, abbreviated as compound A), 2-[(2-{(4S)-4-[(1E,3R)-8-fluoro-3-hydroxy-4,4-dimethyl-1-octenyl]-2-oxo-1,3-oxazolidin-3-yl}ethyl)thio]-1,3-thiazole-4-carboxylic acid, (2E)-7-{(1R,2R)-2-[(1E,3S,5S)-3-hydroxy-5-methyl-1-nonenyl]-5-oxocyclopentyl}-2-heptenoic acid, 2-{[2-((4S)-4-{(1E,3R)-3-hydroxy-3-[1-(3-methoxypropyl)cyclobutyl]-1-propenyl}-2-oxo-1,3-oxazolidin-3-yl)ethyl]sulfanyl}-1,3-thiazole-4-carboxylic acid, 2-{[2-((4S)-4-{(1E,3R)-3-[1-(2-cyclohexylethyl)cyclobutyl]-3-hydroxy-1-propenyl}-2-oxo-1,3-oxazolidin-3-yl)ethyl]sulfanyl}-1,3-thiazole-4-carboxylic acid, 2-{[2-((4S,5S)-4-{(1E)-3-hydroxy-3-[1-(3-methoxypropyl)cyclobutyl]-1-propenyl}-5-methyl-2-oxo-1,3-oxazolidin-3-yl)ethyl]sulfanyl}-1,3-thiazole-4-carboxylic acid, 2-[(2-{(4S,5S)-4-[(1E)-4-hydroxy-4-methyl-1-nonenyl]-5-methyl-2-oxo-1,3-oxazolidin-3-yl}ethyl)sulfanyl]-1,3-thiazole-4-carboxylic acid or 2-[(2-{(1R,2R)-2-[(1E)-5-cyclohexyl-4-hydroxy-4- methyl-1-pentenyl]-5-oxocyclopentyl}ethyl)sulfanyl]-1,3-thiazole-4-carboxylic acid and the like.

According to the present invention, unless otherwise indicated and as is apparent for those skilled in the art, symbol ⋯ indicates that it is bound to the opposite side of the sheet (namely α-configuration), ◢ indicates that it is bound to the front side of the sheet (namely β-configuration), ╱ indicates that it is a α-configuration, β-configuration or an optional mixture thereof.

For example, in formula (I), a bind of X-D or a bind of Y—W may be a α-configuration, β-configuration or an optional mixture thereof.

Unless otherwise specifically mentioned, all isomers are included in the present invention. For example, alkyl, alkenyl, alkynyl, alkoxy, alkylthio, alkylene, alkenylene and alkynylene include straight chain and branched ones. Moreover, all of isomers due to double bond, ring and fused ring (E-, Z-, cis- and trans-forms), isomers due to presence of asymmetric carbon(s) (R-, S-, α- and β-configuration, enantiomer and diastereomer) and the like, optically active compounds having optical rotation (D-, L-, d- and l-forms), polar compound by chromatographic separation (more polar compound and less polar compound), equilibrium compounds, rotational isomers, an optional mixture thereof and a racemic mixture are included in the present invention.

The salt is preferably a pharmacologically acceptable salt, and water-soluble. The suitable salt includes salt with alkaline metal (e.g., potassium, sodium and the like), salt with alkaline earth metal (e.g., calcium, magnesium and the like), ammonium salt, salt with pharmaceutically acceptable organic amine (e.g., tetramethylammonium, triethylamine, methylamine, dimethylamine, cyclopentylamine, benzylamine, phenethylamine, piperidine, monoethanolamine, diethanolamine, tris(hydroxymethyl)aminomethane, lysine, arginine, N-methyl-D-glucamine and the like) or acid addition salt and the like.

The acid addition salt is preferably water-soluble. The suitable acid addition salt includes, for example, inorganic acid salt such as hydrochloride, hydrobromide, hydroiodide, sulfate, phosphate and nitrate and the like, or organic acid salt such as acetate, lactate, tartrate, benzoate, citrate, methanesulfonate, ethanesulfonate, benzenesulfonate, toluenesulfonate, isothionate, glucuronate and gluconate and the like.

The compound of the present invention and the salt thereof may be converted to a solvate.

The solvate is preferably non-toxic and water-soluble. The suitable solvate includes, for example, solvate of hydrate or alcoholate (e.g., ethanolate and the like).

The compound of the present invention and the pharmaceutically acceptable salt thereof are all preferable. The compound described in Examples and the pharmacologically acceptable salt thereof and the like, include specifically. Moreover, the salt includes a quaternary ammonium salt. The quaternary ammonium salt is the compound where nitrogen of the compound of the present invention is quarternalized by $R^0$ and the like.

$R^0$ is C1-8 alkyl and C1-8 alkyl substituted by phenyl.

The compound of the present invention can be converted into an N-oxide by optional methods. The N-oxide is the compound in which nitrogen of the compound of the present invention is oxidized and the like.

The compound of the present invention can be converted into an S-oxide by optional methods. The S-oxide is the compound in which sulfur of the compound of the present invention is oxidized and the like.

The compound of the present invention can be converted into a cyclodextrin clathrate thereof by the method described in JP50-3362, JP52-31404 or JP61-52146 using α-, β- or γ-cyclodextrin, or a mixture thereof. Converting into the corresponding cyclodextrin clathrates serves to increase the stability and solubility in water of the compounds, and therefore it is useful in the use for pharmaceuticals.

A prodrug of the compound of the present invention includes a compound which is converted to the compound of the present invention by a reaction with an enzyme, gastric acid or the like in the living body. For example, with regard to a prodrug of the compound of the present invention, when the compound of the present invention has an amino group, the compounds in which the amino group was, for example, acylated, alkylated or phosphorylated (e.g., compounds in which is the amino group of the compound of the present invention was eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, acetoxymethylated, tert-butylated, and the like); when the compound of the present invention has a hydroxyl group, the compounds in which the hydroxyl group was, for example, acylated, alkylated, phosphorylated or borated (e.g., compounds in which the hydroxyl group of the compound of the present invention was acetylated, palmitoylated, propanoylated, pivaloylated, succinylated, fumarylated, alanylated or dimethylaminomethylcarbonylated); and when the compound of the present invention has a carboxyl group, the compounds in which the carboxyl group was, for example, esterified or amidated (e.g., compounds in which the carboxyl group of the compound of the present invention was made into ethyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl)methyl ester, cyclohexyloxycarbonylethyl ester or methylamide). These compounds may be produced by a known method per se. The prodrug of the compound of the present invention may be either a hydrate or a non-hydrate. The prodrug of the compound of the present invention may also be a compound which is converted to the compound of the present invention under a physiologic condition as described in "*Iyakuhin no kaihatsu*, Vol. 7 (Bunshi-sekkei), pp. 163~198 (Hirokawa-Shoten), 1990". And the compound of the present invention may also be labeled by a radio isotope (such as $^3H$, $^{14}C$, $^{35}S$, $^{125}I$, and the like).

Processes for the Preparation of the Compound of the Present Invention

The compound represented by formula (I) can be prepared by the methods which were properly improved and combined known methods such as a method described in JP52-27753, JP55-100360, WO03/074483, WO05/053707, Synlett 2002, No. 1, 239-242 or Comprehensive Organic Transformations: A Guide to Functional Group Preparations, 2nd Edition (Richard C. Larock, John Wiley & Sons Inc, 1999), a method described below, or a method described in Examples.

Among the compounds represented by formula (I), a compound wherein —W is

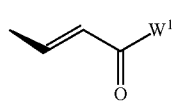

(wherein $W^1$ is hydrocarbon which may have a substituent(s).), i.e., a compound represented by formula (Ia):

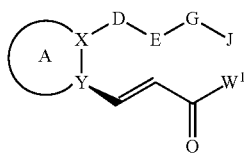

(Ia)

(wherein all symbols have the same meanings as described above.), can be prepared by the following reaction using a compound represented by formula (II):

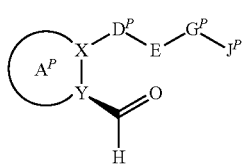

(II)

(wherein ring $A^P$, $D^P$, $G^P$ and $J^P$ have the same meanings as ring A, D, G and J respectively. With proviso that, carboxy, hydroxy, amino or thiol in ring $A^P$, $D^P$, $G^P$ and $J^P$ may be protected, if necessary. Other symbols have the same meanings as described above.), and a compound represented by formula (III):

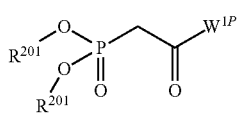

(III)

(wherein $R^{201}$ is C1-4 alkyl, $W^{1P}$ has the same meaning as $W^1$. With proviso that, carboxy, hydroxy, amino or thiol in $W^{1P}$ may be protected, if necessary.), if necessary, followed by removal of the protecting group.

This reaction is well known, and, for example, it is carried out at −15 to 30° C. in the presence of sodium hydride in an organic solvent (e.g., anhydrous tetrahydrofuran, dimethylformamide, dioxane and the like).

A deprotection reaction of the protecting group is well known, and can be carried out by the method described below.

The protecting group of carboxy includes, for example, methyl, ethyl, allyl, tert-butyl, trichloroethyl, benzyl (Bn) and phenacyl and the like.

The protecting group of hydroxy includes, for example, methyl, trityl, methoxymethyl (MOM), 1-ethoxyethyl (EE), methoxyethoxymethyl (MEM), 2-tetrahydropyranyl (THP), trimethylsilyl (TMS), triethylsilyl (TES), tert-butyldimethylsilyl(TBDMS), tert-butyldiphenylsilyl (TBDPS), acetyl (Ac), pivaloyl, benzoyl, benzyl (Bn), p-methoxybenzyl, allyloxycarbonyl (Alloc), or 2,2,2-trichloroethoxycarbonyl (Troc) and the like.

The protecting group of amino includes, for example, benzyloxycarbonyl, tert-butoxycarbonyl, allyloxycarbonyl (Alloc), 1-methyl-1-(4-biphenyl)ethoxycarbonyl (Bpoc), trifluoroacetyl, 9-fluorenylmethoxycarbonyl, benzyl (Bn), p-methoxybenzyl, benzyloxymethyl (BOM) or 2-(trimethylsilyl)ethoxymethyl (SEM) and the like.

The protective group of thiol includes, for example, benzyl, methoxybenzyl, methoxymethyl (MOM), 2-tetrahydropyranyl (THP), diphenylmethyl or acetyl (Ac) and the like.

With regard to the protective group for carboxyl, hydroxyl, amino or thiol, there is no particular limitation to the above ones so far as it is a group which is able to be easily and selectively detached. For example, a deprotection reaction may be carried out by a method mentioned in "T. W. Greene, *Protective Groups in Organic Synthesis*, Wiley, New York, 1999".

The reaction for removing the protective group for carboxyl, hydroxyl, amino or thiol is well known and its examples are as follows:

(1) a hydrolyzing reaction with an alkali,
(2) a deprotection reaction under an acidic condition,
(3) a deprotection reaction by hydrogenolysis,
(4) a deprotection reaction of silyl,
(5) a deprotection reaction using a metal, and
(6) a deprotection reaction using a metal complex.

These methods will be specifically illustrated as follows:

(1) A deprotection reaction by a hydrolyzing reaction with an alkali is carried out, for example, about 0 to 40° C. using a hydroxide of alkaline metal (e.g., sodium hydroxide, potassium hydroxide and lithium hydroxide and the like), a hydroxide of alkaline earth metal (e.g., barium hydroxide and calcium hydroxide and the like) or a carbonate (e.g., sodium carbonate and potassium carbonate and the like) or an aqueous solution thereof or a mixture thereof in an organic solvent (e.g., methanol, tetrahydrofuran and dioxane and the like);

(2) A deprotection reaction under an acidic condition is carried out, for example, about 0 to 100° C. in an organic acid (e.g., acetic acid, trifluoroacetic acid, methanesulfonic acid and p-tosylate and the like), or an inorganic acid (e.g., hydrochloric acid and sulfuric acid and the like) or a mixture thereof (e.g., hydrogen bromide/acetic acid and the like) in an organic solvent (e.g., dichloromethane, chloroform, dioxane, ethyl acetate and anisole and the like);

(3) A deprotection reaction by hydrogenolysis is carried out, for example, about 0 to 200° C., under hydrogen atmosphere of ordinary pressure or high pressure, or by the using ammonium formate, in the presence of a catalyst (e.g., palladium-carbon, palladium black, palladium hydroxide, platinum oxide and Raney nickel and the like) in a solvent (such as an ether type (e.g., tetrahydrofuran, dioxane, dimethoxyethane and diethyl ether and the like), an alcohol type (such as methanol and ethanol and the like), a benzene type (such as benzene and toluene and the like), a ketone type (such as acetone and methyl ethyl ketone and the like), a nitrile type (such as acetonitrile and the like), an amide type (such as dimethylformamide and the like), water, ethyl acetate, acetic acid or a mixed solvent comprising two or more thereof and the like);

(4) A deprotection reaction of silyl is carried out, for example, about 0 to 40° C. using tetrabutylammonium fluoride in an organic solvent miscible with water (e.g., tetrahydrofuran and acetonitrile and the like);

(5) A deprotection reaction using metal is carried out, for example, about 0 to 40° C. with or without ultrasonic wave in the presence of powdery zinc in an acidic solvent (e.g., acetic acid, a buffer of pH 4.2 to 7.2 or a mixed solution of the solution with an organic solvent such as tetrahydrofuran);

(6) A deprotection reaction using a metal complex is carried out, for example, about 0 to 40° C. using a metal complex (e.g., tetrakistriphenylphosphine palladium (0), bis(triphenylphosphine) palladium (II) dichloride, palladium (II) acetate and tris(triphenylphosphine) rhodium (I) chloride and the like) in the presence or absence of a phosphine agent (e.g., triphenyl phosphine and the like) in the presence of a trap reagent (e.g., tributyltin hydride, triethylsilane, dimedone, morpholine, diethylamine and pyrrolidine and the like), an organic acid (e.g., acetic acid, formic acid and 2-ethylhexanoic acid and the like) and/or an organic acid salt (e.g., sodium 2-ethylhexanoate and potassium 2-ethylhexanoate) in an organic solvent (e.g., dichloromethane, dimethylformamide, tetrahydrofuran, ethyl acetate, acetonitrile, dioxane and ethanol and the like), water or a mixed solvent thereof.

Apart from the above, the deprotection reaction may also be carried out, for example, according to the methods described in T. W. Greene, Protective Groups in Organic Synthesis, Wiley, New York, 1999.

As persons skilled in the art can easily understand that the aimed compound of the present invention is able to be easily produced by using appropriate ones among these deprotection reactions.

Among the compounds represented by formula (I), a compound wherein —W is

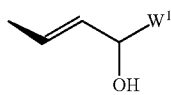

(wherein all symbols have the same meanings as described above), i.e., a compound represented by formula (Ia-1):

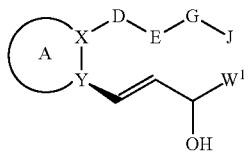
(Ia-1)

(wherein all symbols have the same meanings as described above) can be prepared by a reduction of a compound represented by formula (IV):

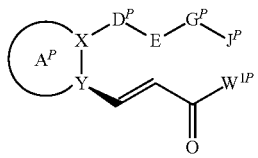
(IV)

(wherein all symbols have the same meanings as described above), if necessary, followed by removal of the protecting group.

This reaction is well known, and, for example, it is carried out about −78 to 30° C. using a reducing agent (e.g., sodium borohydride, borane-tetrahydrofuran complex and borane-dimethyl sulfide complex and the like) in the presence or absence of (R)-2-methyl-CBS-oxazaborolidin or (S)-2-methyl-CBS-oxazaborolidin, in the presence or absence of cerium chloride in an organic solvent (e.g., anhydrous tetrahydrofuran, methanol and dichloromethane and the like).

A deprotection reaction of the protecting group can be carried out by the same method as described above.

Among the compounds represented by formula (I), a compound wherein —W is

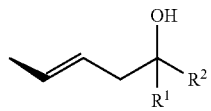

(wherein all symbols have the same meanings as described above), i.e., a compound represented by formula (Ib):

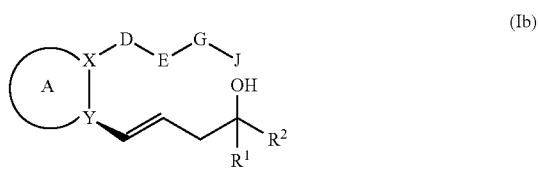
(Ib)

(wherein all symbols have the same meanings as described above) can be prepared by the following reaction using a compound represented by formula (II) and a compound represented by formula (V):

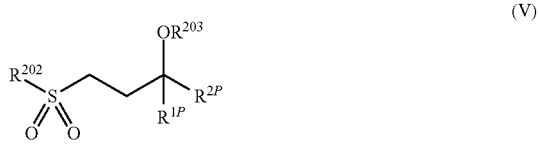
(V)

(wherein $R^{202}$ is aryl (e.g., 1-phenyl-1H-tetrazolyl and phenyl and the like), $R^{203}$ is a protecting group (e.g., trimethylsilyl and tert-butyldimethylsilyl and the like), and $R^{1P}$ and $R^{2P}$ have the same meanings as $R^1$ and $R^2$ respectively. With proviso that, carboxy, hydroxy, amino or thiol in $R^{1P}$ and $R^{2P}$ may be protected, if necessary.), if necessary, followed by removal of the protecting group.

This reaction is well known, and, for example, it is carried out about −100 to −20° C. in the presence of a base (e.g, potassium, hexamethyldisilazide, lithium diisopropylamide and butyllithium and the like) in an organic solvent (e.g., anhydrous tetrahydrofuran, dimethoxyethane, toluene and dimethylformamide and the like).

A deprotection reaction of the protecting group can be carried out by the same method as described above.

Moreover, the compounds represented by formula (Ib) can be prepared by the following reaction using a compound represented by formula (II) and a compound represented by formula (VI):

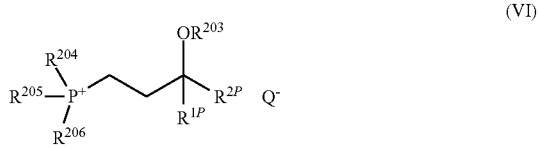
(VI)

(wherein $R^{204}$, $R^{205}$ and $R^{206}$ are, each independently aryl (e.g., phenyl and the like), $Q^−$ is halogen ion and the other symbols have the same meanings as described above), if necessary, followed by removal of the protecting group.

This reaction is well known, and, for example, it is carried out about −100 to −20° C. in the presence of a base (e.g, lithium diisopropylamide, butyllithium and sodium hydride and the like) in an organic solvent (e.g, anhydrous tetrahydrofuran, dimethoxyethane, toluene and dimethylformamide and the like).

Among the compounds represented by formula (I), a compound wherein —W is

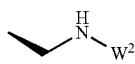

(wherein W² is hydrocarbon group which may have a substituent(s)), i.e., a compound represented by formula (Ic):

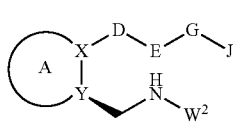

(wherein all symbols have the same meanings as described above.) can be prepared by a reductive amination of a compound represented by formula (II) and a compound represented by formula (VII):

(wherein $W^{2p}$ has the same meaning as $W^2$. With proviso that, carboxy, hydroxy, amino or thiol in $W^{2p}$ may be protected, if necessary.), if necessary, followed by removal of the protecting group.

This reductive amination is well known, and, for example, it is carried out about 0 to 100° C. in the presence of a reducing agent (e.g., sodium cyanoborohydride, sodium borohydride, sodium triacetoxyborohydride and pyridineborane and the like) in an organic solvent (e.g., methanol, ethanol, dichloromethane, tetrahydrofuran, dimethoxyethane and diethyl ether and the like).

A deprotection reaction of the protecting group can be carried out by the same method as described above.

Among the compounds of the present invention, the other compounds than the above-described can be prepared easily by combination of the known methods such as the methods described in JP52-27753, JP55-100360, WO2003/74483, WO05/053707, Synlett 2002, No. 1, 239-242 or *Comprehensive Organic Transformations: A Guide to Functional Group Preparations*, 2$^{nd}$ Edition (Richard C. Larock, John Willey & Sons Inc, 1999) or the methods modified partially thereof.

The other starting compounds or the compounds used as reagent are the known compounds, and can be prepared easily by combination of the known methods such as the methods described in JP52-27753, JP55-100360, WO2003/074483, WO05/053707, Synlett 2002, No. 1, 239-242 or *Comprehensive Organic Transformations: A Guide to Functional Group Preparations*, 2$^{nd}$ Edition (Richard C. Larock, John Willey & Sons Inc, 1999) or Elmer J. Rauckman et. al., J. Org. Chem., vol. 41, No. 3, 1976, p 564-565 and the like. Moreover, the starting compounds may be used as salts thereof. As the salts, ones described as the salts of the compounds of the present invention described above are used.

In each reaction of the present description, the reactions with heating, as will be apparent to those skilled in the art, it may be carried with water bath, oil bath, sand bath and microwave and the like.

In each reaction of the present description, it may be used a solid phase reagent which was supported by polymer (e.g., polystyrene, polyacrylamide, polypropylene or polyethyleneglycol and the like).

In each reaction of the present description, the obtained products may be purified by conventional techniques. For example, the purification may be carried out by distillation under atmosphere of ordinary pressure or vacuum, by high performance liquid chromatography with silica gel or magnesium silicate, by thin layer chromatography, by ion-exchange resin, by scavenger resin, by column chromatography, by washing or by recrystallization. The purification may be done each reaction or after several reactions.

Toxicity

The toxicity of the compounds of the present invention is very low and therefore the compounds may be considered safe for pharmaceutical use.

Application to Pharmaceuticals

An EP2 agonist which may have an EP3 agonistic effect has an effect of regenerating and/or protecting nerves, and is therefore useful for a prevention and/or a treatment of a disease of the peripheral nervous system, such as lower and upper motor neuron diseases (e.g., amyotrophic lateral sclerosis, paraneoplastic syndrome, progressive bulbar paralysis, progressive muscular atrophy, primary lateral sclerosis, progressive pseudobulbar paralysis, post poliomyelitis syndrome, genetic spinal muscular atrophy (type I spinal muscular atrophy) (Werdnig-Hoffman disease), type II (intermediate) spinal muscular atrophy, type III spinal muscular atrophy (Wohlfart-Kugelberg-Welander disease), (type IV spinal muscular atrophy) and the like); nerve root diseases (e.g., hernia of intervertebral disk, spinal canal stenosis, cervical spondylosis and the like); plexus diseases (e.g., acute brachial plexitis and the like); thoracic outlet compression syndrome; peripheral nerve disorders (e.g., mononeuropathy, multiple mononeuropathy, multiple neuropathy, Guillain-Barre syndrome, genetic neuropathy (e.g., peroneal muscular atrophy (Chalcot-Marie-Tooth disease), hypertrophic interstitial neuropathy (Dejerine-Sottas disease), diabetic peripheral nerve disorders, neurofibromatosis (e.g., peripheral neurofibroma (Recklinghausen disease), central nervefibroma and the like), *Proteus* syndrome and the like), neuromuscular transmission diseases (e.g., myasthenia gravis, amyotonia congenita syndrome, Eaton-Lambert syndrome, botulism, systemic tetany syndrome, Isaacs syndrome and the like) and the like.

Moreover, an EP2 agonist having an EP3 agonistic effect has little influence on the blood pressure and the ventricular rate, and a small probability of grave side effect to circulatory system.

Furthermore, the medicaments of the present invention have also an effect of increasing cauda equina blood flow, and are useful for a prevention and/or a treatment of such as lumbago, lower limb pain, lower limb numbness, intermittent claudication, urocystic disorder, rectum disorder or sexual dysfunction, and can be used an agent as a prevention and/or a therapy for such as spinal canal stenosis and/or cervical vertebra symptom.

In the present description, the nervous protective effect includes an effect of prevention for nervous function which deteriorates and nervous necrosis.

The medicaments of the present invention may be administered as a combined preparation by combining with other medicaments for the purpose of 1) supplementing and/or enhancing of a prevention and/or a treatment effect of the compound, 2) improvement in pharmacokinetics and absorption of the compound, and reduction of dose of the compound, and/or 3) reduction of side effect of the compound.

The combined preparation of the medicaments of the present invention with other medicaments may be administered in a form of a compounded agent in which both components are compounded in a preparation or may be in a form in which they are administered by means of separate preparations. The case of administration by means of separate preparations includes a simultaneous administration and administrations with time difference. In the case of administrations with time difference, the medicament of the present invention may be firstly administered followed by administering the other medicament or the other medicament may be administered firstly followed by administering the medicament of the present invention. Methods for each of the administration are the same or different.

Diseases prevented and/or treated by the concomitant medication are especially no limited. Any disease supplementing and/or enhancing of a prevention and/or a treatment effect of the medicaments of the present invention is included.

The other medicaments for the purpose of supplementing and/or enhancing of a prevention and/or a treatment effect for spinal canal stenosis of the medicaments of the present invention include, for example, prostaglandins, prostaglandin derivatives, nonsteroidal anti-inflammatory drugs (NSAID), vitamins, muscle relaxants, antidepressants, nitric oxide synthase inhibitors, aldose reductase inhibitors, poly ADP-ribose polymerase (PARP) inhibitors, excitatory amino acid receptor antagonists (e.g., NMDA receptor antagonists and AMPA receptor antagonists etc), radical scavengers, astrocyte modulators, phosphodiesterase (PDE) inhibitors and immunosuppressive drugs (e.g., cyclosporine and FK506) and the like.

Examples of prostaglandins (hereinafter, abbreviated as PG) include PG receptor agonists and the like. Examples of PG receptors include PGE receptors (EP1, EP2, EP3 and EP4), PGD receptors (DP and CRTH2), PGF receptors (FP), PGI receptors (IP), TX receptors (TP) and the like. In addition, examples of prostaglandin derivatives include limaprost, limaprost alfadex, beraprost and the like.

Examples of nonsteroidal anti-inflammatory drugs (NSAID) include sasapyrine, sodium salicylate, aspirin, aspirin dialuminate, diflunisal, indometacin, suprofen, ufenamate, dimethyl isopropylazulene, bufexamac, felbinac, diclofenac, tolmetin sodium, clinoril, fenbufen, nabumetone, proglumetacin, indometacin farnesil, acemetacin, proglumetacin maleate, amfenac sodium, mofezolac, etodolac, ibuprofen, ibuprofen piconol, naproxen, flurbiprofen, flurbiprofenaxetil, ketoprofen, fenoprofen calcium, tiaprofenic acid, oxaprozin, pranoprofen, loxoprofen sodium, alminoprofen, zaltoprofen, mefenamic acid, mefenamic acid aluminium, tolfenamic acid, floctafenine, ketophenylbutazone, oxyphenbutazone, piroxicam, tenoxicam, ampiroxicam, napageln ointment, epirizole, tiaramide hydrochloride, tinoridine hydrochloride, emorfazone, sulpyrine, migrenin, Saridon, Sedes G, amipylo-N, solvon, pyrine compounding cold medicine, acetaminophen, phenacetin, dimetotiazine mesilate, cimetoride-combined drug, non-pyrine compounding cold medicine and the like.

Examples of muscle relaxants include tolperisone hydrochloride, chlorzoxazone, chlormezanone, methocarbamol, phenprobamate, pridinol mesilate, chlorphenesin carbamate, baclofen, eperisone hydrochloride, afloqualone, tizanidine hydrochloride, alcuronium chloride, suxamethonium chloride, tubocurarine chloride, dantrolene sodium, pancuronium bromide, vecuronium bromide and the like.

Antidepressants include tricyclic antidepressants or tetracyclic antidepressants. Examples of tricyclic antidepressants include imipramine hydrochloride, desipramine hydrochloride, clomipramine hydrochloride, trimipramine maleate, amitriptyline hydrochloride, nortriptyline hydrochloride, lofepramine hydrochloride, amoxapine, dosulepin hydrochloride and the like. Examples of tetracyclic antidepressants include maprotiline, mianserin and the like.

Phosphodiesterase (PDE) inhibitors include, for example, PDE3 inhibitors, PDE4 inhibitors or PDE5 inhibitors and the like. Examples of PDE4 inhibitors include Cilomilast (brand name: Ariflo), Roflumilast (BY-217), Arofylline, OPC-6535, ONO-6126, IC-485, AWD-12-281, CC-10004, CC-1088, KW-4490, lirimilast, ZK-117137, YM-976, BY-61-9987, CC-7085, CDC-998, MEM-1414, ND-1251, Bay19-8004, D-4396, PD-168787, Atizoram (CP-80633), Cipamfylline (BRL-61063), Rolipram, NIK-616, SCH-351591 or V-11294A and the like. Examples of PDE5 inhibitors include Sildenafil, Sildenafil citrate and the like. Examples of the other PDE inhibitors include NT-702 and the like.

Examples of nitric oxide synthase inhibitors include $N^{\omega}$-monomethyl-L-arginine (L-NMMA), $N^{\omega}$-nitro-L-arginine (L-NNA), $N^{\omega}$-nitro-L-arginine methylester (L-NAME), $N^{\omega}$-amino-L-arginine (L-NAA), $N^{\omega}$-cyclopropyl-L-arginine (L-CPA), $N^{\omega}$-allyl-L-arginine (L-ALA), $N^{\omega}$-nitro-L-arginine-p-nitroanilide, $N^{\omega},N^{\omega}$-dimethylarginine, 2-iminobiotin, S-methyl-L-thiocitrulline, S-ethyl-L-thiocitrulline, L-thiocitrulline, L-homothiocitrulline, 2-iminopiperidine, 2-iminohomopiperidine, S-methylisothiourea, S-ethylisothiourea (EIT), S-isopropylisothiourea, S,S'-(1,3-phenylenebis(1,2-ethanediyl))bisisothiourea, 2-aminothiazoline, 2-aminothiazole, N-(3-(aminomethyl)benzyl)-acetamigine, $N^{\delta}$-(4,5-dihydrothiazol-2-yl)ornithine, $N^{\omega}$-iminoethyl-ornithine (L-NIO), L-$N^{6}$-(1-iminoethyl)-lysin, 2-amino-5,6-dihydro-6-methyl-4H-1,3-thiazine (AMT), or (+)-trans-3-imino-5-methyl-7-chloro-2-azabicyclo[4.1.0]heptane and the like.

Examples of aldose reductase inhibitors include Tolrestat, Epalrestat, 3,4-dihydro-2,8-diisopropyl-3-thioxo-2H-1,4-benzoxazine-4-acetic acid, Imirestat, Zenarestat and the like.

Examples of poly ADP-ribose polymerase (PARP) inhibitors include 1,5-dihydroxyisoquinoline and the like.

A weight ratio of the medicaments of the present invention and the other medicaments is not limited in particular.

The other medicaments may be administrated with an optional combination of two or more kinds which are same or different.

Moreover, examples of the other medicaments for supplementing and/or enhancing the preventive and/or treatment effect of the medicaments of the present invention include not only the known compounds but also a new compound on the basis of the mechanism described above.

In order to use the medicaments of the present invention, these are normally administered to the entire or local part of human body orally or parenterally.

At the same time to be different by the medicament used in the present invention, the doses to be administered are determined depending upon, for example, age, body weight, symptom, the desired therapeutic effect, the route of administration, and the duration of the treatment. In the human adult, the doses per person are generally from 1 ng to 100 mg, by oral administration, up to several times per day, and from 0.1 ng to 10 mg, by parenteral administration, up to several times per day, or continuous administration from 1 to 24 hours per day from vein.

As mentioned above, the doses depend upon various conditions. Therefore, there are cases in which doses lower than or greater than the ranges described above may be used.

The medicaments of the present invention, or the concomitant medications combined the medicaments of the present invention with the other medicaments may be administered in solid preparations for internal use and liquid preparations for internal use each for oral administration, and injections, external use, suppositories, eye drops or inhalant each for parenteral administration and the like.

Examples of the solid preparations for internal use for oral administration include tablets, pills, capsules, powders and granules and the like. The capsules include hard capsules and soft capsules.

In such solid preparations for internal use, such as one or more of the active substance(s) may be admixed with vehicles (e.g., lactose, mannitol, glucose, microcrystalline cellulose or starch and the like), binders (e.g., hydroxypropyl cellulose, polyvinylpyrrolidone or magnesium metasilicate aluminate and the like), disintegrants (e.g., cellulose calcium glycolate and the like), lubricants (e.g., magnesium stearate and the like), stabilizing agents, and solution adjuvants (e.g., glutamic acid or aspartic acid and the like) and prepared according to methods well known in normal pharmaceutical practice. The solid preparations for internal use may, if desired, be coated with coating agents (e.g., sugar, gelatin, hydroxypropyl cellulose or hydroxypropylmethyl cellulose phthalate and the like), or be coated with two or more films. And further, coating may include containment within capsules of absorbable materials such as gelatin.

Liquid preparations for internal use for oral administration include pharmaceutically acceptable solutions, suspensions and emulsions, syrups and elixirs. In such liquid preparations, one or more of the active substance(s) may be dissolved, suspended or emulsified into diluent(s) commonly used in the art (e.g., purified water, ethanol or a mixture thereof and the like). Besides such liquid preparations may also comprise some additives, such as wetting agents, suspending agents, emulsifying agents, sweetening agents, flavor agents, aroma, preservative agents or buffering agents.

The dosage forms of the external preparation for parenteral administration include, for example, ointment, gel, cream, poultice, patch, liniment, propellant, inhalation, spray, eye drops and nasal spray and the like. These products include one or more of the active substance(s) and are prepared by a known method or a usual method.

Ointments are prepared by a known method or a usual method. For example, it is prepared by triturating or dissolving one or more active substance(s) in a base. The substrate of ointment is selected from known or usual one. For example, those selected from higher fatty acid or higher fatty acid ester (e.g., adipic acid, myristic acid, palmitic acid, stearic acid, oleic acid, adipic acid ester, myristic acid ester, palmitic acid ester, stearic acid ester, oleic acid ester, and the like), wax (e.g., beeswax, whale wax, ceresin, and the like), surfactant (e.g., polyoxyethylene alkyl ether phosphoric acid ester, and the like), higher alcohol (e.g., cetanol, stearyl alcohol, cetostearyl alcohol, and the like), silicon oil (e.g., dimethyl polysiloxane, and the like), hydrocarbon (e.g., hydrophilic petrolatum, white petrolatum, purified lanolin, liquid paraffin, and the like), glycol (e.g., ethylene glycol, diethylene glycol, propylene glycol, polyethylene glycol, macrogol, and the like), vegetable oil (e.g., castor oil, olive oil, sesame oil, turpentine oil, and the like), animal oil (e.g., mink oil, egg yolk oil, squalane, squalene, and the like), water, absorption accelerators, agents for preventing contact dermatitis are used alone or in combination. Moreover, humectants, preservative agents, stabilizers, antioxidative agents, flavoring agents, and the like, may be contained.

A gel is prepared by a known method or a usual method. For example, it is prepared by dissolving one or more active substance(s) in a base. The substrate of gel is selected from known or usual one. For example, those selected from lower alcohol (e.g., ethanol, isopropylalcohol, and the like), gelling agent (e.g., carboxymethyl cellulose, hydroxyethyl cellulose, hydroxypropyl cellulose, ethyl cellulose, and the like), neutralizing agent (e.g., triethanolamine, diisopropanolamine, and the like), surfactant (e.g., polyethylene glycol monostearate, and the like), gum, water, absorption accelerator, and agent for preventing contact dermatitis are used alone or in combination. Moreover, preservative agents, antioxidative agents, flavoring agents, and the like, may be contained.

A cream is prepared by a known method or a usual method. For example, it is prepared by dissolving or emulsifying one or more active substance(s) in a base. The substrate of cream is selected from known or usual one. For example, those selected from higher fatty acid ester, lower alcohol, hydrocarbon, polyalcohol (e.g., propylene glycol, 1,3-butylene glycol, and the like), higher alcohol (e.g., 2-hexyldecanol, cetanol, and the like), emulsifying agent (e.g., polyoxyethylene alkyl ether, fatty acid ester, and the like), water, absorption accelerator, and agent for preventing contact dermatitis are used alone or in combination. Moreover, preservative agents, antioxidative agents, flavoring agents, and the like, may be contained.

A fomentation is prepared by a known method or a usual method. For example, it is prepared by dissolving one or more active substance(s) in a base to obtain a kneaded mixture and spreading the kneaded mixture over a substrate. The substrate of fomentation is selected from known or usual one. For example, those selected from thickener (e.g., polyacrylic acid, polyvinylpyrrolidone, gum acacia, starch, gelatin, methyl cellulose, and the like), humectant (e.g., urea, glycerin, propylene glycol, and the like), filler (e.g., kaolin, zinc oxide, talc, calcium, magnesium, and the like), water, solubilizing agents, tackifiers, and agents for preventing contact dermatitis are used alone or in combination. Moreover, preservative agents, antioxidative agents, flavoring agents, and the like, may be contained.

A patch is prepared by a known method or a usual method. For example, it is prepared by dissolving one or more active substance(s) in a base, and spreading the solution over a substrate. The substrate of patch is selected from known or usual one. For example, those selected from polymer bases, fats and oils, higher fatty acids, tackifiers, and agents for preventing contact dermatitis are used alone or in combination. Moreover, preservative agents, antioxidative agents, flavoring agents, and the like, may be contained.

A liniment is prepared by a known method or a usual method. For example, it is prepared by dissolving, suspending or emulsifying one or more active substance(s) in one or more kind(s) selected from water, alcohol (e.g., ethanol, polyethylene glycol, and the like), higher fatty acids, glycerin, soap, emulsifiers, and suspending agents. Moreover, preservative agents, antioxidative agents, flavoring agents, and the like, may be contained.

A propellant, an inhalation and a spray may comprise in addition to a diluent used commonly, a stabilizer such as sodium bisulfite and an isotonization buffer such as sodium chloride, sodium citrate or citric acid.

Injections for parenteral administration include solutions, suspensions, emulsions and solid forms which are dissolved or suspended into solvent(s) for injection immediately before use. The injection is used after dissolving, suspending, or emulsifying one or more active substance(s) in a solvent. As the solvent, for example, distilled water for injection, physiological saline, vegetable oil, and alcohols such as propylene glycol, polyethylene glycol or ethanol are used alone or in combination. Injections may comprise stabilizing agents, solution adjuvants (e.g., glutamic acid, aspartic acid or POLYSORBATE80 (registered trade mark), and the like), suspending agents, emulsifying agents, soothing agent, buffering agents, preservative. These injections may be sterilized at a final step, or may be prepared by an aseptic manipulation. Also, these injections may also be manufactured in the form of sterile solid forms, for example, freeze-dried products, which may be dissolved in sterile water or some other sterile diluent(s) for injection immediately before use.

Eye drops for parenteral administration include ophthalmic solution, ophthalmic suspension, ophthalmic emulsion, ophthalmic solution soluble when used, and eye ointment.

These eye drops are prepared according to a known method. For example, one or more active substance(s) are dissolved, suspended or emulsified in a solvent before use. As the solvent for eye drops, for example, sterilized purified water, physiological saline, and other aqueous solvent or non-aqueous agent for injection (e.g., vegetable oil, and the like) are used alone or in combination. If necessary, the eye drops may contain appropriately selected isotonizing agents (e.g., sodium chloride, concentrated glycerin, and the like), buffering agents (e.g., sodium phosphoate, sodium acetate, and the like), surfactants (e.g., polysolvate 80 (trade name), polyoxyl 40 stearate, polyoxyethylene hardened castor oil, and the like), stabilizers (e.g., sodium citrate, sodium edetate, and the like), and antiseptics (e.g., benzalkonium chloride, paraben, and the like). These eye drops are prepared by sterilizing in the final process, or prepared by an aseptic treatment. Also, a sterile solid, for example, a freeze-dried product can be prepared and used after dissolving in sterilized distilled water or sterilized purified water for sterile injection, or the other solvent before use.

The dosage forms of inhalations for parenreral administration include aerosol, powders for inhalation or liquids for inhalation. The liquids for inhalation may be dissolved or suspended in water or the other appropriate solvent as needed.

These inhalations are prepared according to a known method.

For example, a liquid for inhalation is prepared by selecting proper additives from antiseptics (e.g., benzalkonium chloride or paraben, and the like), coloring agents, buffering agents (e.g., sodium phosphate or sodium acetate, and the like), isotonizing agents (e.g., sodium chloride or concentrated glycerin, and the like), thickening agents (e.g., carboxyvinylpolymer, and the like), or absorption accelerators, and the like, if necessary.

A powder for inhalation is prepared by selecting proper additives from lubricant agents (e.g., stearin acid and the salt thereof, and the like), binding agents, (e.g., starch, dextrin, and the like), diluting agents (e.g., lactose, cellulose, and the like), coloring agents, antiseptics (e.g., benzalkonium chloride or p-aminobenzonic acid, and the like), absorption accelerators, and the like, if necessary.

In case of administration of liquid for inhalation, spray (e.g., atomizer, nebulizer, and the like) is usually used and in case of administration of powder for inhalation, inhalation administration apparatus for powder agents is usually used.

The other compositions for parenteral administration include suppositories for intrarectal administration and pessaries for vaginal administration which comprise one or more of the active substance(s) and may be prepared by methods known per se.

The medicaments of the present invention can apply to human and mammalian (e.g., monkey, cattle, horse, pig, sheep, dog, cat, rat, mouse, and the like) aside from human.

The Effect of the Invention

The medicaments of the present invention are useful for an origin therapy of peripheral nervous system diseases in nervous regenerative and/or protective action being provided.

BEST MODE FOR CARRYING OUT THE INVENTION

The present invention is explained below in detail based on Examples, but the present invention is not limited thereto.

In chromatographic separations and TLC, the solvents in parenthesis show the eluting and developing solvents and the ratios of the solvents used are by volume.

Unless otherwise specified, NMR data is $^1$H-NMR data. The solvents in parenthesis in NMR show the solvents used for measurement. All the compounds described in the present description were named using computer program which names generally on the basis of IUPAC, using ACD/Name Batch (registered trademark) or according to IUPAC nomenclature system. For example, a compound represented by

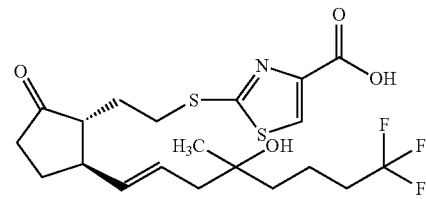 [SMILES: CC(O)(C/C=C/[C@H]1CCC(=O)[C@@H]1CCSc1nc(C(=O)O)cs1)CCCC(F)(F)F]

was named 2-[(2-{(1R,5R)-2-oxo-5-[(1E)-8,8,8-trifluoro-4-hydroxy-4-methyl-1-octenyl]cyclopentyl}ethyl)thio]-1,3-thiazole-4-carboxylic acid.

Example 1

Ethyl 4-cyclohexyl-3-hydroxy-3-methylbutanoate (compound 1)

To a solution of 1-cyclohexylacetone (10 g) in 1,4-dioxane (70 mL) were added ethyl bromoacetate (11 mL), zinc (9.1 g) and iodine (1.7 g) at room temperature, and the mixture was handled by ultrasonic wave for 2 hours. To the reaction solution was added dropwise 1N hydrochloric acid, and the reaction solution was extracted with ethyl acetate. The organic layer was washed with water and brine, dried over anhydrous magnesium sulfate and concentrated. The obtained residue was purified by column chromatography on silica gel (n-hexane:ethyl acetate=15:1) to give the title compound (15.8 g) having the following physical data.
TLC: Rf 0.15 (n-hexane:ethyl acetate=10:1);
NMR (CDCl$_3$): δ 0.84-1.92, 2.37-2.58, 4.18.

Example 2

4-cyclohexyl-3-methyl-1,3-butanediol (compound 2)

To a suspended solution of lithium aluminium hydride (3.68 g) in tetrahydrofuran (70 mL) was added dropwise the solution of compound 1 (15.8 g) in tetrahydrofuran (30 mL) at 0° C., and the mixture was stirred for 35 minutes. To the reaction solution was added ethyl acetate at 0° C. till foaming disappears, and added dropwise 5N hydrochloric acid (10 mL). The reaction solution was risen to room temperature, stirred overnight. The reaction solution was dried over anhydrous magnesium sulfate and concentrated. The obtained residue was purified by column chromatography on silica gel (n-hexane:ethyl acetate=1:1) to give the title compound (9.0 g) having the following physical data.

TLC: Rf 0.24 (n-hexane:ethyl acetate=2:1);
NMR (CDCl$_3$): δ 0.84-2.13, 3.77-3.98.

Example 3

1-cyclohexyl-2-methyl-4-[(1-phenyl-1H-tetrazol-5-yl)thio]-2-butanol (compound 3)

To a solution of compound 2 (5.95 g) in toluene (60 mL) were added tetrabutylammonium bromide (1.1 g) and 5N sodium hydroxide (27 mL) at 0° C., and added dropwise a suspended solution of tosyl chloride (6.7 g) in toluene (20 mL). The reaction solution was stirred for an hour at room temperature. To the reaction solution was added 1-phenyl-1H-tetrazole-5-thiol (6.8 g), and the reaction solution was stirred for 3.5 hours at 60° C. The reaction solution was extracted with tert-butoxymethyl. The organic layer was washed with brine, dried over anhydrous magnesium sulfate and concentrated. The obtained residue was purified by column chromatography on silica gel (n-hexane:ethyl acetate=17:3) to give the title compound (9.56 g) having the following physical data.

TLC: Rf 0.45 (toluene: ethyl acetate=4:1);
NMR (CDCl$_3$): δ 0.84-1.87, 1.92-2.11, 3.40-3.56, 7.45-7.67.

Example 4

1-cyclohexyl-2-methyl-4-[(1-phenyl-1H-tetrazol-5-yl)sulfonyl]-2-butanol (compound 4)

To a solution of compound 3 (9.56 g) in methylene chloride (138 mL) was added m-chloroperbenzoic acid (16.7 g) at 0° C. The reaction solution was stirred at room temperature overnight. To the reaction solution was added an aqueous saturated solution of sodium hydrogen carbonate. The reaction solution was concentrated, and extracted with ethyl acetate. The organic layer was washed with an aqueous saturated solution of sodium hydrogen carbonate and brine, dried over anhydrous magnesium sulfate, and concentrated to give the title compound (10.4 g) having the following physical data.

TLC: Rf 0.50 (n-hexane:ethyl acetate=2:1);
NMR (CDCl$_3$): δ 0.88-1.89, 1.96-2.20, 3.82-3.95, 7.55-7.74.

Example 5

5-({4-cyclohexyl-3-methyl-3-[(trimethylsilyl)oxy] butyl}sulfonyl)-1-phenyl-1H-tetrazole (compound 5)

To a solution of compound 4 (10.4 g) in methylene chloride (28 mL) were added imidazole (3.8 g) and trimethylsilyl chloride (5.3 mL) at 0° C. and the mixture was stirred for an hour. To the reaction solution was added water and the reaction solution was extracted with ethyl acetate. The organic layer was washed with brine, dried over anhydrous magnesium sulfate and concentrated. The obtained residue was purified by column chromatography on silica gel (n-hexane:ethyl acetate=9:1) to give the title compound (10.2 g) having the following physical data.

TLC: Rf 0.67 (n-hexane:ethyl acetate=4:1);
NMR (CDCl$_3$): δ 0.13, 0.84-1.81, 1.90-2.15, 3.72-3.88, 7.54-7.76.

Example 6

Ethyl 2-({2-[(1R,2S,5S)-2-({[tert-butyl(diphenyl) silyl]oxy}methyl)-5-hydroxycyclopentyl]ethyl}thio)-1,3-thiazole-4-carboxylate (compound 6)

To a solution of (3aR,4S,6aS)-4-({[tert-butyl(diphenyl)silyl]oxy}methyl)hexahydro-2H-cyclopenta[b]furan-2-one (1.00 g) in anhydrous tetrahydrofuran (9.00 mL) was added lithium aluminium hydride (97.0 mg) at 0° C. and the mixture was stirred for 20 minutes. To the reaction solution was added water at 0° C. and the mixture was extracted with ethyl acetate. The reaction solution was washed with an aqueous saturated solution of sodium tartrate and brine, dried over anhydrous sodium sulfate, and concentrated. To a solution of methanesulfonyl chloride (0.23 mL) in anhydrous tetrahydrofuran (5.00 mL) were added the obtained residue and a solution of diisopropylethylamine (1.29 mL) in anhydrous tetrahydrofuran (9.00 mL) at −5° C. and the mixture was stirred for 20 minutes. To the reaction solution was added anhydrous methanol (43.0 μL) at −5° C. and the mixture was stirred for 15 minutes. To the reaction solution was added trimethylsilyl chloride (0.49 mL) at −5° C. and the mixture was stirred for 10 minutes at room temperature. To the reaction solution were added potassium carbonate (1.10 g), potassium thioacetate (578 mg) and anhydrous dimethylformamide (20.0 mL), and the mixture was stirred for 5 hours at 50° C. The reaction solution was poured into iced water, extracted with tert-butyl methyl ether, washed with water and brine, dried over anhydrous sodium sulfate and concentrated. To a solution of the obtained residue in ethanol (13.0 mL) were added tri-n-butylphosphine (0.07 mL), ethyl 2-bromo-1,3-thiazole-4-carboxylate (657 mg) and potassium carbonate (770 mg) and the mixture was stirred for an hour at room temperature. Furthermore, the reaction solution was stirred at 50° C. overnight. The reaction solution was diluted in ethyl acetate, and washed with an aqueous saturated solution of ammonium chloride, water and brine. The reaction solution was dried over anhydrous sodium sulfate and concentrated. The obtained residue was dissolved in tetrahydrofuran (8.60 mL). 1N hydrochloric acid (1.86 mL) was added thereto at 0° C., and the mixture was stirred for 30 minutes at room temperature. The reaction solution was diluted in ethyl acetate, washed with water and brine, dried over anhydrous sodium sulfate and concentrated. The obtained residue was purified by column chromatography on silica gel (n-hexane:ethyl acetate=4:1) to give the title compound (624 mg) having the following physical data.

TLC: Rf 0.36 (n-hexane:ethyl acetate=2:1);
NMR (CDCl$_3$): δ 1.05, 1.38, 1.77, 2.82, 3.20, 3.58, 4.41, 7.41, 7.65, 7.96.

Example 7

Ethyl 2-({2-[(1R,2S,5S)-2-(acetyloxy)-5-(hydroxymethyl)cyclopentyl]ethyl}thio)-1,3-thiazole-4-carboxylate (compound 7)

To a solution of compound 6 (42.2 g) in pyridine (75 mL) was added acetic anhydride (13 mL) at 0° C., moreover added 4-N,N-dimethylaminopyridine (453 mg) and the mixture was stirred for 2 hours at room temperature. The reaction solution was diluted in ethyl acetate, and washed with 1N hydrochloric acid and brine, dried over anhydrous sodium sulfate and concentrated. To a solution of the obtained residue in tetrahydrofuran (140 mL) was added a solution of 1M tetrabutylammonium fluoride in tetrahydrofuran (110 mL) at 0° C., and the mixture was stirred for an hour at room temperature. To the reaction solution was added water and the mixture was extracted with ethyl acetate. The organic layer was washed with water and brine, dried over anhydrous magnesium sulfate, and concentrated. The obtained residue was purified by column chromatography on silica gel (n-hexane:ethyl acetate=7:3) to give the title compound (20.2 g) having the following physical data.

TLC: Rf 0.48 (n-hexane:ethyl acetate=1:1);

NMR (CDCl$_3$): δ 1.39, 1.44-2.16, 3.16-3.37, 3.53-3.75, 4.40, 5.23-5.35, 8.02.

Example 8

Ethyl 2-({2-[(1R,2S,5S)-2-(acetyloxy)-5-formylcyclopentyl]ethyl}thio)-1,3-thiazole-4-carboxylate (compound 8)

To a solution of compound 7 (2.95 g) in dimethyl sulfoxide (20 mL)/ethyl acetate (30 mL) were added triethylamine (7.8 mL) and sulfur trioxide-pyridine complex (4.5 g) at 10° C., and the mixture was stirred for an hour at room temperature. To the reaction solution was added 1N hydrochloric acid and the mixture was extracted with ethyl acetate. The organic layer was washed with water and brine, dried over anhydrous sodium sulfate, and concentrated to give the title compound (2.93 g) having the following physical data.

TLC: Rf 0.27 (n-hexane:ethyl acetate=2:1);

NMR (CDCl$_3$): δ 1.32-1.49, 1.78-2.15, 2.35-2.51, 2.69-2.84, 3.10-3.31, 4.32-4.48, 5.29-5.37, 8.02, 9.67.

Example 9

Ethyl 2-{[2-((1R,2S,5S)-2-(acetyloxy)-5-{(1E)-5-cyclohexyl-4-methyl-4-[(trimethylsilyl)oxy]-1-pentenyl}cyclopentyl)ethyl]thio}-1,3-thiazole-4-carboxylate (compound 9)

To a solution of compound 5 (7.20 g) in dimethoxyethane (40.0 mL) was added dropwise potassium bis(trimethylsilyl)amide (0.5M toluene solution, 32.0 mL) slowly, and the mixture was stirred for 60 minutes at −78° C. To the reaction solution was added dropwise a solution of compound 8 (2.93 g) in dimethoxyethane (40.0 mL) slowly, and the mixture was stirred for 25 minutes at −78° C. The reaction temperature was risen to 0° C., and the reaction solution was stirred for 50 minutes. To the reaction solution was added an aqueous saturated solution of sodium bicarbonate and the mixture was extracted with ethyl acetate. The organic layer was washed with an aqueous saturated solution of sodium bicarbonate and brine, dried over anhydrous magnesium sulfate, and concentrated. The obtained residue was purified by column chromatography on silica gel (n-hexane:ethyl acetate=9:1) to give the title compound (2.23 g) having the following physical data.

TLC: Rf 0.63 (n-hexane:ethyl acetate=2:1);

NMR (CDCl$_3$): δ 0.08-0.11, 0.79-2.24, 2.30-2.45, 3.11-3.37, 4.40, 5.16-5.32, 5.35-5.53, 8.02.

Example 10

Ethyl 2-[(2-{(1R,2S,5R)-2-(acetyloxy)-5-[(1E)-5-cyclohexyl-4-hydroxy-4-methyl-1-pentenyl]cyclopentyl}ethyl)thio]-1,3-thiazole-4-carboxylate (compound 10)

To a solution of compound 9 (2.23 g) in ethyl acetate (10 mL) was added dropwise 4N hydrogen chloride/ethyl acetate solution (9.4 mL) slowly at 0° C., and the mixture was stirred for 10 minutes. To the reaction solution was added an aqueous saturated solution of sodium bicarbonate slowly and the mixture was extracted with ethyl acetate. The organic layer was washed with an aqueous saturated solution of sodium bicarbonate and brine, dried over anhydrous magnesium sulfate, and concentrated. The obtained residue was purified by column chromatography on silica gel (n-hexane:ethyl acetate=3:1) to give the title compound (1.41 g) having the following physical data.

TLC: Rf 0.33 (n-hexane:ethyl acetate=2:1);

NMR (CDCl$_3$): δ 0.81-2.23, 2.31-2.50, 3.16-3.35, 4.40, 5.19-5.40, 5.42-5.62, 8.02.

Example 11

2-[(2-{(1R,2R,5S)-2-[(1E)-5-cyclohexyl-4-hydroxy-4-methyl-1-pentenyl]-5-hydroxycyclopentyl}ethyl)thio]-1,3-thiazole-4-carboxylic acid (compound 11)

To a solution of compound 10 (1.32 g) in methanol (25 mL) was added dropwise 2N aqueous solution of sodium hydroxide (6.4 mL) at 0° C. The reaction solution was stirred for 45 minutes at room temperature. After cooling to 0° C., to the reaction solution was added 2N hydrochloric acid and the mixture was extracted with ethyl acetate. The organic layer was washed with water and brine, dried over anhydrous magnesium sulfate, and concentrated to give the title compound (1.14 g) having the following physical data.

TLC: Rf 0.39 (ethyl acetate:methanol:acetic acid=15:1:1);

NMR (CDCl$_3$): δ 0.84-2.25, 2.33-2.53, 2.77-3.92, 4.48-4.57, 5.28-5.40, 5.42-5.57, 8.08.

Example 12

2-[(2-{(1R,2S,5R)-2-(acetyloxy)-5-[(1E)-5-cyclohexyl-4-hydroxy-4-methyl-1-pentenyl]cyclopentyl}ethyl)thio]-1,3-thiazole-4-carboxylic acid (compound 12)

Compound 11 (486 mg) was dissolved in pyridine (6.00 mL) and thereto was added acetic anhydride (0.21 mL) at 0° C. The mixture was stirred at room temperature overnight. The reaction solution was diluted in ethyl acetate, washed with 1N hydrochloric acid and brine, dried over anhydrous sodium sulfate, and concentrated to give the title compound (540 mg) having the following physical data.

TLC: Rf 0.72 (ethyl acetate:methanol:acetic acid=15:1:1);

NMR (CDCl$_3$): δ 0.83-2.28, 2.31-2.51, 3.06-3.53, 5.27-5.44, 5.45-5.62, 8.09.

Example 13

(10S,12E,13aR,16S,16aR)-10-(cyclohexylmethyl)-10-methyl-8-oxo-1,10,11,13a,14,15,16,16a-octahydro-2H,8H-7,4-(azeno)cyclopenta[j][1,5,7]oxadithiacyclopentadecin-16-yl acetate (compound 13)

To a solution of compound 12 (531 mg) in anhydrous tetrahydrofuran (11 mL) were added triethylamine (0.18 mL) and 2,4,6-trichlorobenzoyl chloride (0.19 mL) at 0° C., and the mixture was stirred for 30 minutes at room temperature after having stirred for an hour. To the reaction solution was added anhydrous toluene (90 mL), and the mixture was filtered. The obtained filtrate was added to a solution of 4-(dimethylamino)pyridine (654 mg) in anhydrous toluene (100 mL) at 100° C. and the mixture was allowed to return to room temperature. The reaction solution was added to 1N hydrochloric acid, and the mixture was extracted with ethyl acetate. The organic layer was washed with water and brine, dried over anhydrous sodium sulfate, and concentrated. The obtained residue was purified by column chromatography on silica gel (n-hexane:ethyl acetate=19:1) to give the title compound (225 mg) having the following physical data.

TLC: Rf 0.48 (n-hexane:ethyl acetate=4:1);

NMR (CDCl₃): δ 0.84-2.30, 2.38, 2.59-2.99, 3.25-3.42, 5.24-5.37, 5.37-5.53, 5.54-5.73, 7.92.

Example 14

2-[(2-{(1R,2R,5S)-2-[(1E,4S)-5-cyclohexyl-4-hydroxy-4-methyl-1-pentenyl]-5-hydroxycyclopentyl}ethyl)thio]-1,3-thiazole-4-carboxylic acid (compound 14)

To a solution of compound 13 (225 mg) in a mixed solution of methanol and tetrahydrofuran (8.0 mL) was added 2N aqueous solution of sodium hydroxide (0.71 mL) at 0° C., and the mixture was stirred for an hour at room temperature. To the reaction solution was added 2N hydrochloric acid (2.0 mL). The mixture was extracted with ethyl acetate, and washed with water and brine. The reaction solution was dried over anhydrous sodium sulfate and concentrated to give the title compound (214 mg) having the following physical data.

TLC: Rf 0.39 (ethyl acetate:methanol:acetic acid=15:1:1);

NMR (CDCl₃): δ 0.85-2.26, 2.34-2.56, 2.83-3.01, 3.18-3.69, 4.49-4.56, 5.34, 5.40-5.56, 8.07.

Example 15

Ethyl 2-[(2-{(1R,2R,5S)-2-[(1E,4S)-5-cyclohexyl-4-hydroxy-4-methyl-1-pentenyl]-5-hydroxycyclopentyl}ethyl)thio]-1,3-thiazole-4-carboxylate (compound 15)

To a solution of compound 14 (214 mg) in N,N-dimethylformamide (3.0 mL) were added potassium carbonate (261 mg) and iodoethane (0.08 mL) at 0° C., and the mixture was stirred for 3 hours at room temperature. To the reaction solution was added an aqueous saturated solution of sodium chloride, and the mixture was extracted with ethyl acetate. The organic layer was washed with water and brine, dried over anhydrous sodium sulfate, and concentrated. The obtained residue was purified by column chromatography on silica gel (n-hexane:ethyl acetate=3:2) to give the title compound (225 mg) having the following physical data.

TLC: Rf 0.18 (n-hexane:ethyl acetate=2:1);

NMR (CDCl₃): δ 0.83-2.12, 2.16, 2.30-2.46, 2.82-2.95, 3.52-3.67, 4.39, 4.44-4.51, 5.24-5.52, 7.97.

Example 16

Ethyl 2-[(2-{(1R,2R)-2-[(1E,4S)-5-cyclohexyl-4-hydroxy-4-methyl-1-pentenyl]-5-oxocyclopentyl}ethyl)thio]-1,3-thiazole-4-carboxylate (compound 16)

To a solution of compound 15 (225 mg) in dimethyl sulfoxide (2.0 mL)/ethyl acetate (4.0 mL) solution was added diisopropylethylamine (0.65 mL) and sulfur trioxide-pyridine complex (298 mg) at 10° C., and the mixture was stirred for 30 minutes. To the reaction solution was added water, and the mixture was extracted with ethyl acetate. The organic layer was washed with 1N hydrochloric acid, water and brine, dried over anhydrous sodium sulfate, and concentrated. The obtained residue was purified by column chromatography on silica gel (n-hexane:ethyl acetate=7:3) to give the title compound (188 mg) having the following physical data.

TLC: Rf 0.26 (n-hexane:ethyl acetate=2:1);

NMR (CDCl₃): δ 0.81-2.28, 2.31-2.61, 3.37-3.47, 4.41, 5.47, 5.60-5.76, 8.01.

Example 17

2-[(2-{(1R,2R)-2-[(1E,4S)-5-cyclohexyl-4-hydroxy-4-methyl-1-penten-1-yl]-5-oxocyclopentyl}ethyl)thio]-1,3-thiazole-4-carboxylic acid (compound 17): hereinafter, abbreviated as compound 17

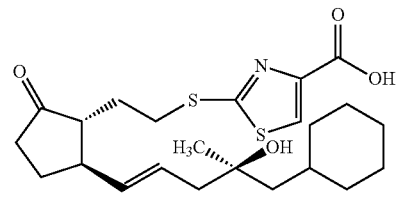 [SMILES: C[C@@](O)(C/C=C/[C@H]1CCC(=O)[C@@H]1CCSc1nc(C(=O)O)cs1)CC1CCCCC1]

To a solution of compound 16 (188 mg) in dimethyl sulfoxide (20 mL)/phosphate-buffered solution (20 mL) was added porcine liver esterase (1.1 mL), and the mixture was stirred at room temperature overnight. The reaction solution was diluted in ethyl acetate, and washed with an aqueous saturated solution of ammonium sulfate, 1N hydrochloric acid, water and brine. The reaction solution was dried over anhydrous sodium sulfate, and concentrated. The obtained residue was purified by column chromatography on silica gel (ethyl acetate) to give the title compound (156 mg) having the following physical data.

TLC: Rf 0.61 (ethyl acetate:methanol:acetic acid=15:1:1);

NMR (CDCl₃): δ 0.85-1.87, 1.90-2.30, 2.32-2.58, 3.36, 5.52, 5.62-5.77, 8.11.

Example 17 (1)

2-[(2-{(1R,2R)-2-[(1E,4S)-4-hydroxy-4-methyl-1-nonen-1-yl]-5-oxocyclopentyl}ethyl)thio]-1,3-thiazole-4-carboxylic acid (compound 17)

By the same procedure as described in Example 9→Example 10→Example 11→Example 12→Example 13→Example 14→Example 15→Example 16→Example 17 using 5-({3-methyl-3-[(trimethylsilyl)oxy]octyl}sulfonyl)-1-phenyl-1H-tetrazole instead of compound 5, the title compound having the following physical data was obtained.

TLC: Rf 0.60 (ethyl acetate:methanol:acetic acid=15:1:1);

NMR (CDCl₃): δ 0.84-0.95, 1.09-1.79, 1.86-2.62, 3.36, 5.52, 5.62-5.77, 8.11.

Example 18 (1)~(19)

By the same procedure as described in Example 9→Example 10→Example 11→Example 15→Example 16→Example 17 using the corresponding compound instead of compound 5, the following compounds were obtained.

Example 18 (1)

2-[(2-{(1R,5R)-2-oxo-5-[(1E)-8,8,8-trifluoro-4-hydroxy-4-methyl-1-octenyl]cyclopentyl}ethyl)thio]-1,3-thiazole-4-carboxylic acid (compound 18-1)

TLC: Rf 0.66 (ethyl acetate:methanol:acetic acid=15:1:1);
NMR (CDCl$_3$): δ 1.19, 1.43-1.76, 1.85-2.61, 3.10, 3.30-3.45, 5.53, 5.61-5.79, 8.11.

Example 18 (2)

2-[(2-{(1R,2R)-2-[(1E)-5-cyclopentyl-4-hydroxy-4-methyl-1-pentenyl]-5-oxocyclopentyl}ethyl)thio]-1,3-thiazole-4-carboxylic acid (compound 18-2)

TLC: Rf 0.55 (ethyl acetate:methanol:acetic acid=15:1:1);
NMR (CDCl$_3$): δ 0.99-2.62, 3.36, 5.51, 5.60-5.78, 8.10.

Example 18 (3)

2-[(2-{(1R,2R)-2-[(1E)-8-fluoro-4-hydroxy-4-methyl-1-octen-1-yl]-5-oxocyclopentyl}ethyl)thio]-1,3-thiazole-4-carboxylic acid (compound 18-3)

TLC: Rf 0.42 (ethyl acetate:methanol:water=40:10:1);
NMR (CDCl$_3$): δ 1.18, 1.39-2.33, 2.33-2.58, 3.36, 4.34-4.40, 4.47-4.60, 5.46-5.60, 5.60-5.76, 8.10.

Example 18 (4)

2-[(2-{(1R,2R)-2-[(1E)-4-hydroxy-4,8-dimethyl-1-nonen-1-yl]-5-oxocyclopentyl}ethyl)thio]-1,3-thiazole-4-carboxylic acid (compound 18-4)

TLC: Rf 0.63 (ethyl acetate:methanol:acetic acid=15:1:1);
NMR (CDCl$_3$): δ 0.73-0.96, 0.99-1.77, 1.83-2.62, 2.62-3.62, 3.19-3.48, 5.45-5.60, 5.61-5.78, 8.11.

Example 18 (5)

2-[(2-{(1R,2R)-2-[(1E)-4-hydroxy-4,8-dimethyl-1,7-nonadien-1-yl]-5-oxocyclopentyl}ethyl)thio]-1,3-thiazole-4-carboxylic acid (compound 18-5)

TLC: Rf 0.50 (ethyl acetate:methanol:acetic acid=15:1:1);
NMR (CDCl$_3$): δ 1.17-1.21, 1.44-1.56, 1.62, 1.68, 1.91-2.32, 2.36-2.53, 3.36, 5.03-5.15, 5.53, 5.62-5.77, 8.11.

Example 18 (6)

2-[(2-{(1R,2R)-2-[(1E)-4-hydroxy-4,7-dimethyl-1,7-octadien-1-yl]-5-oxocyclopentyl}ethyl)thio]-1,3-thiazole-4-carboxylic acid (compound 18-6)

TLC: Rf 0.53 (ethyl acetate:methanol:acetic acid=15:1:1);
NMR (CDCl$_3$): δ 1.18-1.22, 1.54-1.70, 1.73-1.75, 1.92-2.31, 2.35-2.58, 3.36, 4.66-4.75, 5.53, 5.63-5.78, 8.11.

Example 18 (7)

2-[(2-{(1R,2R)-2-[(1E)-6-cyclobutyl-4-hydroxy-4-methyl-1-hexen-1-yl]-5-oxocyclopentyl}ethyl)thio]-1,3-thiazole-4-carboxylic acid (compound 18-7)

TLC: Rf 0.49 (ethyl acetate:methanol:acetic acid=15:1:1);
NMR (CDCl$_3$): δ 1.12-1.21, 1.22-2.83, 3.26-3.45, 5.44-5.60, 5.60-5.77, 8.11.

Example 18 (8)

2-[(2-{(1R,2R)-2-[(1E)-4-hydroxy-4,7-dimethyl-1-octen-1-yl]-5-oxocyclopentyl}ethyl)thio]-1,3-thiazole-4-carboxylic acid (compound 18-8)

TLC: Rf 0.47 (ethyl acetate:methanol:acetic acid=15:1:1);
NMR (CDCl$_3$): δ 0.83-0.93, 1.11-1.31, 1.39-1.57, 1.57-1.78, 1.90-2.30, 2.34-2.59, 3.36, 5.52, 5.59-5.78, 8.10.

Example 18 (9)

2-[(2-{(1R,2R)-2-[(1E)-6-cyclopropyl-4-hydroxy-4-methyl-1-hexen-1-yl]-5-oxocyclopentyl}ethyl)thio]-1,3-thiazole-4-carboxylic acid (compound 18-9)

TLC: Rf 0.30 (ethyl acetate:methanol:acetic acid=15:1:1);
NMR (CDCl$_3$): δ −0.21-0.15, 0.30-0.54, 0.52-0.73, 0.80-4.57, 1.02-1.39, 1.46-1.77, 1.85-2.34, 2.33-2.59, 3.21-3.47, 5.43-5.58, 5.59-5.79, 8.10.

Example 18 (10)

2-[(2-{(1R,2R)-2-[(1E)-4-hydroxy-7-methoxy-4-methyl-1-hepten-1-yl]-5-oxocyclopentyl}ethyl)thio]-1,3-thiazole-4-carboxylic acid (compound 18-10)

TLC: Rf 0.33 (methylene chloride:methanol=4:1);
NMR (CDCl$_3$): δ 1.16, 1.46-2.61, 3.26-3.56, 5.43-5.57, 5.60-5.80, 8.07.

Example 18 (11)

2-[(2-{(1R,2R)-2-[(1E)-4-hydroxy-4-methyl-1-octen-5-yn-1-yl]-5-oxocyclopentyl}ethyl)thio]-1,3-thiazole-4-carboxylic acid (compound 18-11)

TLC: Rf 0.40 (ethyl acetate:methanol:acetic acid=15:1:1);
NMR (CDCl$_3$): δ 1.02-1.18, 1.40-1.53, 1.58-1.79, 1.89-2.61, 3.28-3.45, 5.57, 5.68-5.85, 8.11.

Example 18 (12)

2-[(2-{(1R,2R)-2-[(1E)-9-fluoro-4-hydroxy-4-methyl-1-nonen-1-yl]-5-oxocyclopentyl}ethyl)thio]-1,3-thiazole-4-carboxylic acid (compound 18-12)

TLC: Rf 0.59 (ethyl acetate:methanol:water=40:10:1);
NMR (CDCl$_3$): δ 1.17, 1.32-2.63, 3.37, 4.36, 4.52, 5.46-5.59, 5.61-5.80, 8.11.

Example 18 (13)

2-[(2-{(1R,2R)-2-[(1E)-4-hydroxy-4-methyl-1-nonen-7-yn-1-yl]-5-oxocyclopentyl}ethyl)thio]-1,3-thiazole-4-carboxylic acid (compound 18-13)

TLC: Rf 0.35 (ethyl acetate:methanol:acetic acid=15:1:1);
NMR (CDCl$_3$): δ 1.18, 1.56-1.74, 1.77, 1.88-2.60, 3.36, 3.70-4.00, 5.51, 5.68, 8.10.

Example 18 (14)

2-[(2-{(1R,2R)-2-[(1E)-10-fluoro-4-hydroxy-4-methyl-1-decen-1-yl]-5-oxocyclo pentyl}ethyl)thio]-1,3-thiazole-4-carboxylic acid (compound 18-14)

TLC: Rf 0.50 (ethyl acetate:methanol:water=40:10:1);
NMR (CDCl$_3$): δ 1.18, 1.22-2.61, 3.26-3.46, 4.35, 4.51, 5.43-5.60, 5.59-5.78, 8.10.

Example 18 (15)

2-[(2-{(1R,2R)-2-[(1E)-4-hydroxy-4-methyl-1-octen-1-yl]-5-oxocyclopentyl}ethyl)thio]-1,3-thiazole-4-carboxylic acid (compound 18-15)

TLC: Rf 0.38 (ethyl acetate:methanol:acetic acid=15:1:1);
NMR (CDCl$_3$): δ 0.78-1.00, 1.15-1.20, 1.22-1.54, 1.57-1.80, 1.84-2.35, 2.34-2.61, 2.68-4.99, 3.17-3.52, 5.44-5.60, 5.61-5.79, 8.11.

Example 18 (16)

2-[(2-{(1R,2R)-2-[(1E)-5-cyclobutyl-4-hydroxy-4-methyl-1-penten-1-yl]-5-oxocyclopentyl}ethyl)thio]-1,3-thiazole-4-carboxylic acid (compound 18-16)

TLC: Rf 0.55 (methylene chloride:methanol=4:1);
NMR (CDCl$_3$): δ 1.09, 1.49-2.60, 3.22-3.48, 5.50, 5.59-5.79, 8.10.

Example 18 (17)

2-[(2-{(1R,2R)-2-[(1E,5E)-4-hydroxy-4-methyl-1,5-nonadien-1-yl]-5-oxocyclopentyl}ethyl)thio]-1,3-thiazole-4-carboxylic acid (compound 18-17)

TLC: Rf 0.62 (ethyl acetate:methanol:acetic acid=15:1:1);
NMR (CDCl$_3$): δ 0.81-0.96, 1.19-1.45, 1.57-1.75, 1.86-2.59, 3.28-3.45, 5.42-5.68, 8.08-8.14.

Example 18 (18)

2-[(2-{(1R,2R)-2-[(1E)-4-hydroxy-4-methyl-1-decen-1-yl]-5-oxocyclopentyl}ethyl)thio]-1,3-thiazole-4-carboxylic acid (compound 18-18)

TLC: Rf 0.53 (ethyl acetate:methanol:acetic acid=15:1:1);
NMR (CDCl$_3$): δ 0.23-4.53, 0.74-1.00, 1.03-1.55, 1.55-1.78, 1.84-2.64, 3.15-3.54, 5.43-5.59, 5.60-5.77, 8.09.

Example 18 (19)

2-[(2-{(1R,2R)-2-[(1E,6E)-4-hydroxy-4-methyl-1,6-nonadien-1-yl]-5-oxocyclopentyl}ethyl)thio]-1,3-thiazole-4-carboxylic acid (compound 18-19)

TLC: Rf 0.48 (ethyl acetate:methanol:water=40:10:1);
NMR (CDCl$_3$): δ 0.99, 1.12-1.19, 1.56-1.77, 1.89-2.61, 3.36, 5.23-5.90, 8.09.

Example 19

Ethyl 2-({2-[(1R,2R)-2-((1E,5E)-4-{[tert-butyl(dimethyl)silyl]oxy}-1,5-nonadiene-1-yl)-5-oxocyclopentyl]ethyl}thio)-1,3-thiazole-4-carboxylate (compound 19)

By the same procedure as described in Example 9→Example 11→Example 15→Example 16 using 1-phenyl-5-({(4E)-3-[(trimethylsilyl)oxy]-4-octen-1-yl}sulfonyl)-1H-tetrazole instead of compound 5, the title compound (210 mg) having the following physical data was obtained.

TLC: Rf 0.50 (n-hexane:ethyl acetate=2:1);
NMR (CDCl$_3$): δ −0.03-0.08, 0.83-0.96, 1.33-1.46, 1.56-1.70, 1.82-2.54, 3.21-3.54, 3.96-4.41, 4.40, 5.23-5.69, 8.02.

Example 20

2-[(2-{(1R,2R)-2-[(1E,5E)-4-hydroxy-1,5-nonadien-1-yl]-5-oxocyclopentyl}ethyl)thio]-1,3-thiazole-4-carboxylic acid (compound 20)

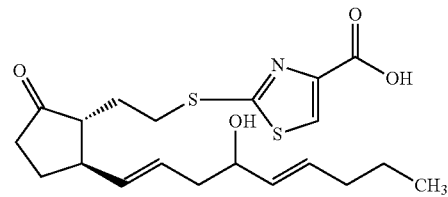 [SMILES: CCC/C=C/C(O)C/C=C/[C@H]1CCC(=O)[C@@H]1CCSc1nc(C(=O)O)cs1]

A solution of compound 19 (119 mg) and p-toluenesulfonic acid monohydrate (97 mg) in methanol (4.0 mL) was stirred for 30 minutes at room temperature. After the reaction solution was diluted in ethyl acetate, it was washed with water and brine, dried over anhydrous sodium sulfate, and concentrated. The obtained residue was purified by column chromatography on silica gel (ethyl acetate:n-hexane=1:2→1:1). By the same procedure as described in Example 17 using the obtained compound instead of compound 16, the title compound having the following physical data was obtained.

TLC: Rf 0.58 (methylene chloride:methanol=4:1);
NMR (CDCl$_3$): δ 0.89, 1.30-1.48, 1.54-1.77, 1.88-2.58, 3.21-3.55, 3.98-4.29, 5.26-5.86, 8.10.

Example 20 (1)~Example 20 (3)

By the same procedure as described in Example 9→Example 11→Example 15→Example 16→Example 20 using the corresponding compound instead of compound 5, the following compounds were obtained.

Example 20 (1)

2-[(2-{(1R,2R)-2-[(1E)-6-cyclobutyl-4-hydroxy-1-hexen-1-yl]-5-oxocyclopentyl}ethyl)thio]-1,3-thiazole-4-carboxylic acid (compound 20-1)

TLC: Rf 0.51 (ethyl acetate:methanol:acetic acid=15:1:1);
NMR (CDCl$_3$): δ 1.30-2.34, 2.36-2.55, 3.27-3.42, 3.59-3.71, 5.54, 5.59-5.71, 8.08-8.14.

Example 20 (2)

2-[(2-{(1R,2R)-2-[(1E,5E)-4-hydroxy-5-methyl-1,5-nonadien-1-yl]-5-oxocyclopentyl}ethyl)thio]-1,3-thiazole-4-carboxylic acid (compound 20-2)

TLC: Rf 0.55 (methylene chloride:methanol=4:1);
NMR (CDCl$_3$): δ 0.89, 1.30-1.43, 1.53-1.74, 1.86-2.60, 3.22-3.49, 3.99-4.09, 5.37, 5.43-5.64, 8.09.

Example 20 (3)

2-[(2-{(1R,2R)-2-[(1E)-4-hydroxy-1-nonen-5-yn-1-yl]-5-oxocyclopentyl}ethyl)thio]-1,3-thiazole-4-carboxylic acid (compound 20-3)

TLC: Rf 0.26 (ethyl acetate:methanol:acetic acid=15:1:1);
NMR (CDCl$_3$): δ 0.90-1.06, 1.41-1.59, 1.60-2.27, 2.34-2.60, 3.14-3.51, 4.28-4.55, 5.57, 5.63-5.80, 8.09-8.12.

Example 21

(5R)-5-({[tert-butyl(dimethyl)silyl]oxy}methyl)-1-(2-hydroxyethyl)-2-pyrrolidinone (compound 21)

To a solution of (5R)-5-(hydroxymethyl)-2-pyrrolidinone (50 g) in dimethylformamide (434 mL) were added imidazole (35 g) and tert-butyldimethylsilyl chloride (68.7 g) on ice bath, and the mixture was stirred for 1.5 hours at room temperature. The reaction solution was poured into cold water, and extracted with ethyl acetate. The obtained organic layer was washed with water and brine, dried over anhydrous magnesium sulfate, and concentrated. To a solution of the obtained residue in anhydrous tetrahydrofuran (869 mL) was added potassium tert-butoxide (53.6 g) on ice bath, and the mixture was stirred for 10 minutes. To the reaction solution was added dropwise ethyl bromoacetate (53 mL), and the mixture was stirred for an hour at room temperature. The reaction solution was poured into an aqueous saturated solution of ammonium chloride which was cooled to 0° C., and extracted with ethyl acetate. The obtained organic layer was washed with brine, dried over anhydrous magnesium sulfate, and concentrated. To a solution of the obtained residue in a solution (869 mL) of tetrahydrofuran/ethanol (7:1) was added sodium borohydride (49 g) and methanol (30 mL) on ice bath, and stirred for 2 hours. The reaction solution was poured into an aqueous saturated solution of ammonium chloride which was cooled to 0° C., and extracted with ethyl acetate. The obtained organic layer was washed with water and brine, dried over anhydrous sodium sulfate, and concentrated to give the title compound (118.8 g) having the following physical data. This compound was used for the next reaction without being purified.
TLC: Rf 0.15 (ethyl acetate);
NMR (CDCl$_3$): δ 0.07, 0.89, 1.60, 1.75-1.94, 2.06-2.24, 2.24-2.58, 3.21-4.07.

Example 22

S-{2-[(2R)-2-({[tert-butyl(dimethyl)silyl]oxy}methyl)-5-oxo-1-pyrrolidinyl]ethyl}ethanethioate (compound 22)

To a solution of compound 21 (118.8 g) and triethylamine (72.6 mL) in tetrahydrofuran (869 mL) was added dropwise methanesulfonyl chloride (37 mL) on ice bath, and the mixture was stirred for 5 minutes at 0° C. To the reaction solution were added dimethylformamide (1.2 L), potassium carbonate (90 g) and thioacetic acid potassium (99 g), and the mixture was stirred for 50 minutes at 50° C. The reaction solution was poured into cold water, and extracted with ethyl acetate. The obtained organic layer was washed with brine, dried over anhydrous magnesium sulfate, and concentrated to give the title compound (143.99 g) having the following physical data. This compound was used for the next reaction without being purified.
TLC: Rf 0.66 (ethyl acetate);
NMR (CDCl$_3$): δ 0.05, 0.06, 0.88, 1.77-1.94, 1.99-2.19, 2.19-2.57, 2.93-3.14, 3.14-3.32, 3.40-3.96.

Example 23

Butyl 2-({2-[(2R)-2-(hydroxymethyl)-5-oxo-1-pyrrolidinyl]ethyl}thio)-1,3-thiazole-4-carboxylate (compound 23)

To a solution of compound 22 (143.99 g) in n-butanol (869 mL) were added ethyl-2-bromo-1,3-thiazole-4-carboxylate (102.53 g), tributylphosphine (10.7 mL) and potassium carbonate (96 g) on ice bath, and the mixture was stirred at 80° C. overnight. The reaction solution was poured into cold water, and extracted with ethyl acetate. The obtained organic layer was washed with brine, dried over anhydrous magnesium sulfate, and concentrated. To a solution of the obtained residue (205.75 g) in ethyl acetate (489 mL) were added a solution (244 mL) of 4N hydrochloric acid/ethyl acetate and n-butanol (400 mL), and the mixture was stirred for an hour at 45° C. To the reaction solution was added toluene, and the mixture was concentrated. The obtained residue which was divided by half into twice was purified by column chromatography on silica gel (ethyl acetate:methanol=9:1) to give the title compound (143 g) having the following physical data.
TLC: Rf 0.58 (ethyl acetate:methanol=9:1);
NMR (CDCl$_3$): δ 0.35-4.75, 0.97, 1.35-1.54, 1.65-1.81, 1.82-1.98, 2.06-2.23, 2.23-2.57, 3.30-3.96, 4.33, 7.99.

Example 24 (1)~Example 24 (3)

By the same procedure as described in Example 8→Example 9→Example 10→Example 11 using compound 5, or 5-({3,6-dimethyl-3-[(trimethylsilyl)oxy]heptyl}sulfonyl)-1-phenyl-1H-tetrazole or 5-({3-methyl-3-[(trimethylsilyl)oxy]-4-nonyn-1-yl}sulfonyl)-1-phenyl-1H-tetrazole instead of compound 5, and compound 23 instead of compound 7, the following compounds were obtained.

Example 24 (1)

2-[(2-{(2R)-2-[(1E)-5-cyclohexyl-4-hydroxy-4-methyl-1-pentenyl]-5-oxo-1-pyrrolidinyl}ethyl)thio]-1,3-thiazole-4-carboxylic acid (compound 24-1)

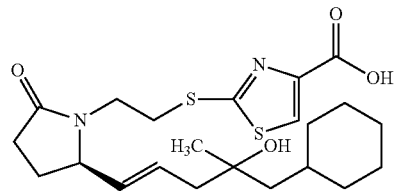 [SMILES: CC(O)(C/C=C/[C@H]1CCC(=O)N1CCSc1nc(C(=O)O)cs1)CC1CCCCC1]

TLC: Rf 0.30 (ethyl acetate:methanol:acetic acid=15:1:1);
NMR (CDCl₃): δ 0.81-1.89, 2.11-2.60, 3.23-3.44, 3.44-3.62, 3.72-3.90, 4.04-4.22, 5.36, 5.71-5.97, 8.09.

Example 24 (2)

2-[(2-{(2R)-2-[(1E)-4-hydroxy-4,7-dimethyl-1-octen-1-yl]-5-oxo-1-pyrrolidinyl}ethyl)thio]-1,3-thiazole-4-carboxylic acid (compound 24-2)

TLC: Rf 0.28 (ethyl acetate:methanol:acetic acid=8:1:1);
NMR (CDCl₃): δ 0.67-1.01, 1.03-1.32, 1.34-1.58, 1.62-1.88, 2.10-2.59, 3.00-4.95, 3.18-3.43, 3.43-3.59, 3.71-3.90, 4.05-4.22, 5.19-5.48, 5.70-5.97, 8.09.

Example 24 (3)

2-[(2-{(2R)-2-[(1E)-4-hydroxy-4-methyl-1-decen-5-yn-1-yl]-5-oxo-1-pyrrolidinyl}ethyl)thio]-1,3-thiazole-4-carboxylic acid (compound 24-3)

TLC: Rf 0.50 (ethyl acetate:methanol:acetic acid=8:1:1);
NMR (CDCl₃): δ 0.78-0.99, 1.28-1.57, 1.65-1.89, 2.08-2.61, 2.75-4.84, 3.19-3.46, 3.44-3.67, 3.68-3.94, 4.01-4.25, 5.20-5.58, 5.71-6.06, 8.08.

Example 25

2-[(2-{(1R,2R)-2-[(1E,4R)-5-cyclohexyl-4-hydroxy-4-methyl-1-penten-1-yl]-5-oxocyclopentyl}ethyl)thio]-1,3-thiazole-4-carboxylic acid (compound 25)

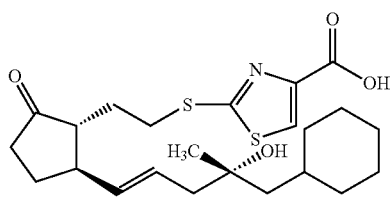 [SMILES: C[C@](O)(C/C=C/[C@H]1CCC(=O)[C@@H]1CCSc1nc(C(=O)O)cs1)CC1CCCCC1]

By the same procedure as described in Example 14→Example 15→Example 16→Example 17 using (10R, 12E,13aR,16S,16aR)-10-(cyclohexylmethyl)-10-methyl-8-oxo-1,10,11,13a,14,15,16,16a-octahydro-2H,8H-7,4-(azeno)cyclopenta[j][1,5,7]oxadithiacyclopentadecin-16-yl acetate (more polar) which was obtained by the same procedure as described in Example 13 instead of compound 13, the title compound having the following physical data was obtained.

TLC: Rf 0.61 (ethyl acetate:methanol:acetic acid=15:1:1);
NMR (CDCl₃): δ 0.77-1.87 (m, 18H), 1.86-2.59 (m, 8H), 3.24-3.47 (m, 4H), 5.52 (dd, J=15.40, 7.70 Hz, 1H), 5.61-5.76 (m, 1H), 8.11 (s, 1H).

Example 25 (1)~Example 25 (9)

By the same procedure as described in Example 9→Example 10→Example 11→Example 12→Example 13→Example 14→Example 15→Example 16→Example 17 using the corresponding compounds instead of compound 5, the following compounds were obtained.

Example 25 (1)

2-[(2-{(1R,2R)-2-[(1E,4R)-4-hydroxy-4-methyl-1-nonen-1-yl]-5-oxocyclopentyl}ethyl)thio]-1,3-thiazole-4-carboxylic acid (compound 25-1)

TLC: Rf 0.60 (ethyl acetate:methanol:acetic acid=15:1:1);
NMR (CDCl₃): δ 0.89 (t, J=6.68 Hz, 3H), 1.11-1.78 (m, 12H), 1.86-2.61 (m, 9H), 3.24-3.47 (m, 4H), 5.53 (dd, J=15.00, 8.25 Hz, 1H), 5.62-5.77 (m, 1H), 8.11 (s, 1H).

Example 25 (2)

Less polar: 2-[(2-{(1R,2R)-2-[(1E,4R)-4-hydroxy-4,8-dimethyl-1-nonen-5-yn-1-yl]-5-oxocyclopentyl}ethyl)thio]-1,3-thiazole-4-carboxylic acid (compound 25-2a)
TLC: Rf 0.64 (ethyl acetate:methanol:acetic acid=15:1:1);
NMR (CDCl₃): δ 0.95 (d, J=6.60 Hz, 6H), 1.46 (s, 3H), 1.58-1.88 (m, 2H), 1.91-2.26 (m, 7H), 2.27-2.57 (m, 4H), 3.20-3.53 (m, 2H), 4.49-6.26 (m, 2H), 5.56 (dd, J=15.21, 7.88 Hz, 1H), 5.65-5.83 (m, 1H), 8.10 (s, 1H).
More polar: 2-[(2-{(1R,2R)-2-[(1E,4S)-4-hydroxy-4,8-dimethyl-1-nonen-5-yn-1-yl]-5-oxocyclopentyl}ethyl)thio]-1,3-thiazole-4-carboxylic acid (compound 25-2b)
TLC: Rf 0.61 (ethyl acetate:methanol:acetic acid=15:1:1);
NMR (CDCl₃): δ 0.93 (d, J=6.97 Hz, 6H), 1.48 (s, 3H), 1.57-1.84 (m, 2H), 1.87-2.26 (m, 7H), 2.26-2.62 (m, 4H), 3.23-3.54 (m, 2H), 3.63-5.17 (m, 2H), 5.56 (dd, J=15.21, 8.25 Hz, 1H), 5.67-5.88 (m, 1H), 8.09 (s, 1H).

Example 25 (3)

Less polar: 2-[(2-{(1R,2R)-2-[(1E,4S)-4-hydroxy-4,7-dimethyl-1-octen-1-yl]-5-oxocyclopentyl}ethyl)thio]-1,3-thiazole-4-carboxylic acid (compound 25-3a)
TLC: Rf 0.53 (ethyl acetate:methanol:acetic acid=15:1:1);
NMR (CDCl₃): δ 0.89 (d, J=6.59 Hz, 6H), 1.11-1.32 (m, 5H), 1.39-1.56 (m, 3H), 1.56-1.76 (m, 1H), 1.88-2.28 (m, 7H), 2.35-2.57 (m, 2H), 3.36 (t, J=7.32 Hz, 2H), 5.52 (dd, J=15.57, 7.68 Hz, 1H), 5.61-5.78 (m, 1H), 8.10 (s, 1H).
More polar: 2-[(2-{(1R,2R)-2-[(1E,4R)-4-hydroxy-4,7-dimethyl-1-octen-1-yl]-5-oxocyclopentyl}ethyl)thio]-1,3-thiazole-4-carboxylic acid (compound 25-3b)
TLC: Rf 0.53 (ethyl acetate:methanol:acetic acid=15:1:1);
NMR (CDCl₃): δ 0.88 (d, J=6.59 Hz, 6H), 1.09-1.33 (m, 5H), 1.36-1.56 (m, 3H), 1.56-1.75 (m, 1H), 1.90-2.32 (m, 7H), 2.32-2.56 (m, 2H), 3.35 (t, J=7.68 Hz, 2H), 5.51 (dd, J=15.21, 7.89 Hz, 1H), 5.62-5.75 (m, 1H), 8.09 (s, 1H).

Example 25 (4)

Less polar: 2-[(2-{(1R,2R)-2-[(1E,4S)-6-cyclobutyl-4-hydroxy-4-methyl-1-hexen-1-yl]-5-oxocyclopentyl}ethyl)thio]-1,3-thiazole-4-carboxylic acid (compound 25-4a)
TLC: Rf 0.64 (ethyl acetate:methanol:acetic acid=15:1:1);
NMR (CDCl₃): δ 1.16 (s, 3H), 1.29-2.30 (m, 19H), 2.33-2.58 (m, 2H), 3.36 (t, J=7.50 Hz, 2H), 5.52 (dd, J=16.08, 8.04 Hz, 1H), 5.61-5.80 (m, 1H), 8.11 (s, 1H).
More polar: 2-[(2-{(1R,2R)-2-[(1E,4R)-6-cyclobutyl-4-hydroxy-4-methyl-1-hexen-1-yl]-5-oxocyclopentyl}ethyl)thio]-1,3-thiazole-4-carboxylic acid (compound 25-4b)
TLC: Rf 0.64 (ethyl acetate:methanol:acetic acid=15:1:1);

NMR (CDCl$_3$): δ 1.17 (s, 3H), 1.25-2.32 (m, 19H), 2.34-2.60 (m, 2H), 3.36 (t, J=7.14 Hz, 2H), 5.53 (dd, J=15.36, 7.86 Hz, 1H), 5.60-5.77 (m, 1H), 8.11 (s, 1H).

Example 25 (5)

Less polar: 2-[(2-{(1R,2R)-2-[(1E,4R)-4-hydroxy-4-methyl-1-decen-5-yn-1-yl]-5-oxocyclopentyl}ethyl)thio]-1,3-thiazole-4-carboxylic acid (compound 25-5a)

TLC: Rf 0.63 (ethyl acetate:methanol:acetic acid=15:1:1);
NMR (CDCl$_3$): δ 0.38-3.85 (m, 2H), 0.90 (t, J=7.14 Hz, 3H), 1.27-1.54 (m, 7H), 1.55-1.78 (m, 1H), 1.93-2.62 (m, 11H), 3.10-3.60 (m, 2H), 5.47-5.65 (m, 1H), 5.66-5.86 (m, 1H), 8.11 (s, 1H).

More polar: 2-[(2-{(1R,2R)-2-[(1E,4S)-4-hydroxy-4-methyl-1-decen-5-yn-1-yl]-5-oxocyclopentyl}ethyl)thio]-1,3-thiazole-4-carboxylic acid (compound 25-5b)

TLC: Rf 0.63 (ethyl acetate:methanol:acetic acid=15:1:1);
NMR (CDCl$_3$): δ 0.35-3.01 (m, 2H), 0.89 (t, J=7.14 Hz, 3H), 1.17-1.54 (m, 7H), 1.54-1.76 (m, 1H), 1.89-2.65 (m, 11H), 3.20-3.53 (m, 2H), 5.50-5.64 (m, 1H), 5.68-5.88 (m, 1H), 8.11 (s, 1H).

Example 25 (6)

2-[(2-{(1R,2R)-2-[(1E,4S)-6-cyclopentyl-4-hydroxy-4-methyl-1-hexen-1-yl]-5-oxocyclopentyl}ethyl)thio]-1,3-thiazole-4-carboxylic acid (compound 25-6)

TLC: Rf 0.47 (ethyl acetate:methanol:acetic acid=15:1:1);
NMR (CDCl$_3$): δ 0.95-1.73 (m, 17H), 1.76-2.34 (m, 8H), 2.37-2.63 (m, 2H), 3.35 (t, J=7.68 Hz, 1H), 3.52-3.66 (m, 2H), 5.53 (dd, J=15.18, 7.86 Hz, 1H), 5.63-5.80 (m, 1H), 8.11 (s, 1H).

Example 25 (7)

2-[(2-{(1R,5R)-2-oxo-5-[(1E,4S)-9,9,9-trifluoro-4-hydroxy-4-methyl-1-nonen-1-yl]cyclopentyl}ethyl)thio]-1,3-thiazole-4-carboxylic acid (compound 25-7)

TLC: Rf 0.43 (ethyl acetate:methanol:acetic acid=15:1:1);
NMR (CDCl$_3$): δ 1.17 (s, 3H), 1.32-1.79 (m, 7H), 1.87-2.26 (m, 9H), 2.34-2.58 (m, 2H), 3.28-3.45 (m, 2H), 5.51 (dd, J=15.00, 8.04 Hz, 1H), 5.60-5.77 (m, 1H), 8.09 (s, 1H).

Example 25 (8)

2-[(2-{(1R,2R)-2-[(1E,4S,7S)-4-hydroxy-4,7-dimethyl-1-nonen-1-yl]-5-oxocyclopentyl}ethyl)thio]-1,3-thiazole-4-carboxylic acid (compound 25-8)

TLC: Rf 0.61 (ethyl acetate:methanol:acetic acid=15:1:1);
NMR (CDCl$_3$): δ 0.76-0.96 (m, 6H), 1.04-1.80 (m, 11H), 1.91-2.31 (m, 7H), 2.33-2.58 (m, 2H), 3.36 (t, J=7.32 Hz, 2H), 5.52 (dd, J=15.36, 8.04 Hz, 1H), 5.62-5.76 (m, 1H), 8.11 (s, 1H).

Example 25 (9)

2-[(2-{(1R,5R)-2-oxo-5-[(1E,4S)-7,7,7-trifluoro-4-hydroxy-4-methyl-1-hepten-1-yl]cyclopentyl}ethyl)thio]-1,3-thiazole-4-carboxylic acid (compound 25-9)

TLC: Rf 0.55 (ethyl acetate:methanol:acetic acid=15:1:1);
NMR (CDCl$_3$): δ 1.19 (s, 3H), 1.55-1.81 (m, 3H), 1.88-2.31 (m, 9H), 2.35-2.57 (m, 2H), 3.37 (t, J=6.77 Hz, 2H), 5.53 (dd, J=15.18, 7.68 Hz, 1H), 5.60-5.75 (m, 1H), 8.10 (s, 1H).

Example 26

Ethyl 2-({2-[(1R,2S,5R)-2-(acetoxy)-5-((1E)-4-{[(1,1-dimethylethyl)(dimethyl)silyl]oxy}-7-methyl-1,7-octadien-1-yl)cyclopentyl]ethyl}thio)-1,3-thiazole-4-carboxylate (compound 26)

By the same procedure as described in Example 9 using 5-[(3-{(1,1-dimethylethyl)(dimethyl)silyl]oxy}-6-methyl-6-heptan-1-yl)sulfonyl]-1-phenyl-1H-tetrazole instead of compound 5, the title compound (389 mg) having the following physical data was obtained.

TLC: Rf 0.51 (n-hexane:ethyl acetate=3:1);
NMR (CDCl$_3$): δ 0.01-0.12 (m, 6H), 0.80-0.97 (m, 9H), 1.30-2.23 (m, 22H), 2.24-2.48 (m, 1H), 3.07-3.37 (m, 2H), 3.57-3.73 (m, 1H), 4.39 (q, J=7.14 Hz, 2H), 4.57-4.74 (m, 2H), 5.13-5.34 (m, 2H), 5.36-5.55 (m, 1H), 8.00 (s, 1H).

Example 27

2-({2-[(1R,2R,5S)-2-((1E)-4-{[(1,1-dimethylethyl)(dimethyl)silyl]oxy}-7-methyl-1,7-octadien-1-yl)-5-hydroxycyclopentyl]ethyl}thio)-1,3-thiazole-4-carboxylic acid (compound 27)

To a solution of compound 26 (389 mg) in ethanol (3 mL) was added 2N aqueous solution of sodium hydroxide, and the mixture was stirred for 90 minutes at room temperature. The reaction solution was cooled on ice bath, adjusted with pH 5 by the addition of 5% aqueous solution of citric acid, and extracted with ethyl acetate. The organic layer was washed with water and brine, dried over anhydrous magnesium sulfate, and concentrated to give the title compound (314 mg) having the following physical data.

TLC: Rf 0.38 (methylene chloride:methanol=4:1);
NMR (CDCl$_3$): δ 0.04 (s, 6H), 0.88 (s, 9H), 1.30-2.24 (m, 15H), 2.27-2.50 (m, 1H), 2.74-2.97 (m, 1H), 3.47-3.78 (m, 3H), 4.47-4.59 (m, 1H), 4.60-4.75 (m, 2H), 5.14-5.32 (m, 1H), 5.32-5.54 (m, 1H), 8.06 (s, 1H).

Example 28

Ethyl 2-({2-[(1R,2R,5S)-2-((1E)-4-{[(1,1-dimethylethyl)(dimethyl)silyl]oxy}-7-methyl-1,7-octadien-1-yl)-5-hydroxycyclopentyl]ethyl}thio)-1,3-thiazole-4-carboxylate (compound 28)

To a solution of compound 27 (314 mg) in N,N-dimethylformamide (3 mL) were added potassium carbonate (334 mg) and iodoethane (964), and the mixture was stirred for 5 hours at room temperature. The reaction solution was diluted in ethyl acetate, washed with water and brine, dried over anhydrous magnesium sulfate, and concentrated to give the title compound (315 mg) having the following physical data.

TLC: Rf 0.39 (n-hexane:ethyl acetate=2:1);
NMR (CDCl$_3$): δ 0.04 (s, 6H), 0.88 (s, 9H), 1.26-2.10 (m, 16H), 2.16 (t, J=6.50 Hz, 2H), 2.23-2.45 (m, 1H), 2.76-2.98 (m, 1H), 3.48-3.74 (m, 3H), 4.38 (q, J=7.14 Hz, 2H), 4.42-4.51 (m, 1H), 4.58-4.73 (m, 2H), 5.15-5.30 (m, 1H), 5.30-5.50 (m, 1H), 7.95 (s, 1H).

Example 29

Ethyl 2-({2-[(1R,2R)-2-((1E)-4-{[(1,1-dimethyl-ethyl)(dimethyl)silyl]oxy}-7-methyl-1,7-octadien-1-yl)-5-oxocyclopentyl]ethyl}thio)-1,3-thiazole-4-carboxylate (compound 29)

To a solution of compound 28 (315 mg) in ethyl acetate (1.5 mL) were added dimethyl sulfoxide (1.5 mL), diisopropyl-ethylamine (0.84 mL) and sulfur trioxide-pyridine complex (387 mg) under a water bath, and the mixture was stirred for an hour. To the reaction solution was added 5% aqueous solution of citric acid, and the mixture was stirred intensely. The reaction solution was extracted with ethyl acetate. The organic layer was washed with water and brine, dried over anhydrous magnesium sulfate, and concentrated. The obtained residue was purified by column chromatography on silica gel (n-hexane:ethyl acetate=90:10→67:33) to give the title compound (279 mg) having the following physical data.

TLC: Rf 0.51 (n-hexane:ethyl acetate=2:1);

NMR (CDCl$_3$): δ 0.01-0.12 (m, 6H), 0.88 (s, 9H), 1.39 (t, J=7.14 Hz, 3H), 1.46-1.68 (m, 3H), 1.70 (s, 3H), 1.81-2.53 (m, 11H), 3.24-3.55 (m, 2H), 3.59-3.76 (m, 1H), 4.39 (q, J=7.14 Hz, 2H), 4.58-4.74 (m, 2H), 5.32-5.50 (m, 1H), 5.50-5.71 (m, 1H), 8.02 (s, 1H).

Example 30

Less polar: Ethyl 2-[(2-{(1R,2R)-2-[(1E,4S)-4-hydroxy-7-methyl-1,7-octadien-1-yl]-5-oxocyclopentyl}ethyl)thio]-1,3-thiazole-4-carboxylate (compound 30a)

More polar: Ethyl 2-[(2-{(1R,2R)-2-[(1E,4R)-4-hydroxy-7-methyl-1,7-octadien-1-yl]-5-oxocyclopentyl}ethyl)thio]-1,3-thiazole-4-carboxylate (compound 30b)

A solution of compound 29 (279 mg) in methanol (5 mL) was cooled on ice bath and thereto was added p-toluene-sulfonic acid (17.6 mg). The mixture was stirred for 6 hours at room temperature. To the reaction solution was added ice water. The mixture was stirred intensely, and extracted with ethyl acetate. The obtained organic layer was washed with water and brine, dried over anhydrous magnesium sulfate, and concentrated. The obtained residue was purified by column chromatography on silica gel (n-hexane:ethyl acetate=75:25→55:45) to give the title compounds (compound 30a: 57 mg, compound 30b: 66 mg) having the following physical data.

Compound 30a:

TLC: Rf 0.50 (n-hexane:ethyl acetate=1:1);

NMR (CDCl$_3$): δ 1.39 (t, J=7.14 Hz, 3H), 1.48-1.69 (m, 3H), 1.72 (s, 3H), 1.79-1.96 (m, 1H), 1.96-2.58 (m, 10H), 3.25-3.43 (m, 1H), 3.43-3.58 (m, 1H), 3.58-3.75 (m, 1H), 4.38 (q, J=7.14 Hz, 2H), 4.60-4.76 (m, 2H), 5.51 (dd, J=15.20, 8.00 Hz, 1H), 5.68 (ddd, J=15.20, 7.50, 6.40 Hz, 1H), 7.99 (s, 1H).

Compound 30b:

TLC: Rf 0.46 (n-hexane:ethyl acetate=1:1);

NMR (CDCl$_3$): δ 1.39 (t, J=7.14 Hz, 3H), 1.48-1.70 (m, 3H), 1.72 (s, 3H), 1.79-2.60 (m, 11H), 3.42 (t, J=7.32 Hz, 2H), 3.52-3.71 (m, 1H), 4.38 (q, J=7.14 Hz, 2H), 4.62-4.76 (m, 2H), 5.51 (dd, J=15.30, 8.00 Hz, 1H), 5.68 (dt, J=15.30, 6.80 Hz, 1H), 8.00 (s, 1H).

Example 31

Less polar origin: 2-[(2-{(1R,2R)-2-[(1E,4S)-4-hydroxy-7-methyl-1,7-octadien-1-yl]-5-oxocyclopentyl}ethyl)thio]-1,3-thiazole-4-carboxylic acid (compound 31a)

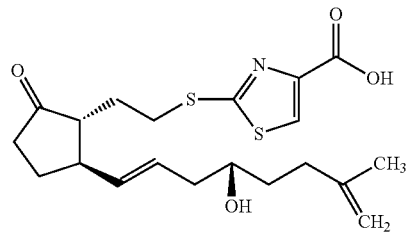 [SMILES: C=C(C)CC[C@H](O)C/C=C/[C@H]1CCC(=O)[C@@H]1CCSc1nc(C(=O)O)cs1]

More polar origin: 2-[(2-{(1R,2R)-2-[(1E,4R)-4-hydroxy-7-methyl-1,7-octadien-1-yl]-5-oxocyclopentyl}ethyl)thio]-1,3-thiazole-4-carboxylic acid (compound 31b)

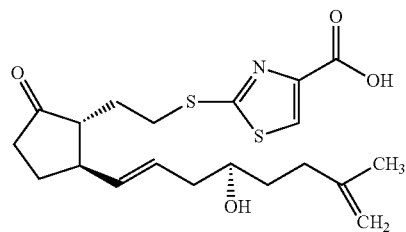 [SMILES: C=C(C)CC[C@@H](O)C/C=C/[C@H]1CCC(=O)[C@@H]1CCSc1nc(C(=O)O)cs1]

To a solution of compound 30a (57 mg) in ethanol (2 mL) were added phosphate-buffered solution (10 mL) and porcine liver esterase (0.70 mL), and the mixture was stirred for 2 days at room temperature. To the reaction solution was added an aqueous solution of ammonium sulfate, and the mixture was stirred intensely. To the reaction solution was added an aqueous solution of citric acid, and the mixture was extracted with ethyl acetate. The organic layer was washed with water and brine, dried over anhydrous magnesium sulfate, and concentrated. The obtained residue was purified by column chromatography on silica gel (methylene chloride:methanol=9:1) to give compound 31a (52 mg).

By the same procedure as described above using compound 30b (66 mg) instead of compound 30a, compound 31b (38 mg) was obtained.

Compound 31a:

TLC: Rf 0.40 (methylene chloride:methanol=4:1);

NMR (CDCl$_3$): δ 1.51-1.71 (m, 3H), 1.73 (s, 3H), 1.84-2.60 (m, 11H), 3.22-3.49 (m, 2H), 3.59-3.79 (m, 1H), 4.64-4.76 (m, 2H), 5.53 (dd, J=15.20, 7.80 Hz, 1H), 5.66 (ddd, J=15.20, 7.80, 6.00 Hz, 1H), 8.10 (s, 1H).

Compound 31b:

TLC: Rf 0.40 (methylene chloride:methanol=4:1);

NMR (CDCl$_3$): δ 1.50-1.82 (m, 6H), 1.86-2.59 (m, 11H), 3.26-3.47 (m, 2H), 3.58-3.78 (m, 1H), 4.71 (d, J=5.12 Hz, 2H), 5.53 (dd, J=15.23, 7.80 Hz, 1H), 5.67 (dt, J=15.23, 6.72, 6.59 Hz, 1H), 8.10 (s, 1H).

Example 31 (1)~Example 31 (5)

By the same procedure as described in Example 26→Example 27→Example 28→Example 29→Example 30→Example 31 using the corresponding compounds instead of compound 5, the following compounds were obtained.

Example 31 (1)

2-[(2-{(1R,2R)-2-[(1E,4S)-6-cyclobutyl-4-hydroxy-1-hexen-1-yl]-5-oxocyclopentyl}ethyl)thio]-1,3-thiazole-4-carboxylic acid (compound 31-1)

TLC: Rf 0.46 (ethyl acetate:methanol:acetic acid=15:1:1);
NMR (CDCl$_3$): δ 1.30-2.59 (m, 21H), 3.24-3.45 (m, 2H), 3.56-3.75 (m, 1H), 5.54 (dd, J=15.00, 7.50 Hz, 1H), 5.59-5.74 (m, 1H), 8.11 (s, 1H).

Example 31 (2)

2-[(2-{(1R,2R)-2-[(1E,4S)-4-hydroxy-8-methyl-1,8-nonadien-1-yl]-5-oxocyclopentyl}ethyl)thio]-1,3-thiazole-4-carboxylic acid (compound 31-2)

TLC: Rf 0.56 (ethyl acetate:methanol:acetic acid=15:1:1);
NMR (CDCl$_3$): δ 1.38-1.55 (m, 4H), 1.54-2.35 (m, 13H), 2.36-2.62 (m, 2H), 3.23-3.51 (m, 2H), 3.56-3.88 (m, 3H), 4.69 (dd, J=10.06, 0.73 Hz, 2H), 5.54 (dd, J=15.18, 7.86 Hz, 1H), 5.60-5.78 (m, 1H), 8.10 (s, 1H).

Example 31 (3)

2-[(2-{(1R,5R)-2-oxo-5-[(1E,4S)-7,7,7-trifluoro-4-hydroxy-1-hepten-1-yl]cyclopentyl}ethyl)thio]-1,3-thiazole-4-carboxylic acid (compound 31-3)

TLC: Rf 0.46 (ethyl acetate:methanol:acetic acid=15:1:1);
NMR (CDCl$_3$): δ 1.53-1.85 (m, 3H), 1.84-2.60 (m, 11H), 2.61-3.85 (m, 2H), 3.22-3.50 (m, 2H), 3.63-3.81 (m, 1H), 5.32-5.80 (m, 2H), 8.10 (s, 1H).

Example 31 (4)

2-[(2-{(1R,2R)-2-[(1E,4S,7S)-4-hydroxy-7-methyl-1-nonen-1-yl]-5-oxocyclopentyl}ethyl)thio]-1,3-thiazole-4-carboxylic acid (compound 31-4)

TLC: Rf 0.46 (ethyl acetate:methanol:acetic acid=15:1:1);
NMR (CDCl$_3$): δ 0.79-0.94 (m, 6H), 1.01-1.76 (m, 8H), 1.83-2.61 (m, 9H), 3.22-3.45 (m, 2H), 3.57-3.72 (m, 1H), 5.54 (dd, J=15.00, 7.68 Hz, 1H), 5.60-5.76 (m, 1H), 8.11 (s, 1H).

Example 31 (5)

2-[(2-{(1R,2R)-2-[(1E,4S)-4-hydroxy-7-methyl-1,7-octadien-1-yl]-5-oxocyclopentyl}ethyl)sulfonyl]-1,3-thiazole-4-carboxylic acid (compound 31-5)

TLC: Rf 0.44 (ethyl acetate:methanol:acetic acid=15:1:1);
NMR (CDCl$_3$): δ 1.55-1.72 (m, 3H), 1.74 (s, 3H), 1.88-2.50 (m, 11H), 3.52-3.89 (m, 3H), 4.72 (d, J=5.49 Hz, 2H), 5.52 (dd, J=14.82, 8.04 Hz, 1H), 5.59-5.74 (m, 1H), 8.58 (s, 1H).

Example 32

2-[(2-{(1R,2R)-2-[(1E)-4-hydroxy-4-methyl-1,7-octadien-1-yl]-5-oxocyclopentyl}ethyl)thio]-1,3-thiazole-4-carboxylic acid (compound 32)

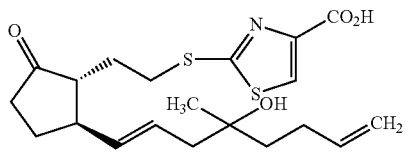 [SMILES: C=CCCC(C)(O)C/C=C/[C@H]1CCC(=O)[C@@H]1CCSc1nc(C(=O)O)cs1]

By the same procedure as described in Example 9→Example 10→Example 11→Example 15→Example 16→Example 17 using 5-({3-methyl-3-[(trimethylsilyl)oxy]-6-heptan-1-yl}sulfonyl)-1-phenyl-1H-tetrazole instead of compound 5, the title compound having the following physical data was obtained.

TLC: Rf 0.60 (ethyl acetate:methanol:acetic acid=15:1:1);
NMR (CDCl$_3$): δ 1.18 (s, 3H), 1.46-1.73 (m, 3H), 1.84-2.29 (m, 9H), 2.30-2.58 (m, 2H), 3.35 (t, J=7.50 Hz, 2H), 4.89-5.09 (m, 2H), 5.51 (dd, J=15.75, 6.96 Hz, 1H), 5.59-5.92 (m, 2H), 8.09 (s, 1H).

Example 33

(10R,12E,13aR)-10-(1-hexyn-1-yl)-10-methyl-1,2,11,13a,14,15-hexahydro-8H-7,4-(azeno)pyrrolo[1,2-j][1,5,7,10]oxadithiazacyclopentadecine-8,16(10H)-dione (compound 33)

To a solution of compound 24-3 (50 mg) and 4-(dimethylamino)pyridine (70 mg) in toluene (11.5 mL) was added dropwise 2,4,6-trichlorobenzoyl chloride (0.036 mL) under a reflux condition. An hour later, the reaction solution was cooled to room temperature, and thereto was added 1N hydrochloric acid. The organic layer was washed with an aqueous saturated solution of sodium bicarbonate and brine, and dried over anhydrous magnesium sulfate. The reaction solution was filtered through Celite (trade name), and concentrated. The obtained residue was purified by column chromatography on silica gel (n-hexane:ethyl acetate=60:40→45:55) to give the title compound (18.6 mg) having the following physical data.

TLC: Rf 0.36 (n-hexane:ethyl acetate=2:3);
NMR (CDCl$_3$): δ 0.90 (t, J=7.14 Hz, 3H), 1.31-1.59 (m, 4H), 1.62-1.79 (m, 1H), 1.81-1.87 (m, 3H), 2.09-2.58 (m, 6H), 2.92 (dd, J=14.27, 11.16 Hz, 1H), 3.17-3.33 (m, 1H), 3.32-3.48 (m, 1H), 3.60-3.87 (m, 2H), 4.04-4.18 (m, 1H), 5.58 (ddd, J=14.91, 8.87, 1.65 Hz, 1H), 5.81 (ddd, J=14.91, 11.16, 3.29 Hz, 1H), 7.97 (s, 1H).

Example 34

2-[(2-{(2R)-2-[(1E,4R)-4-hydroxy-4-methyl-1-decen-5-yn-1-yl]-5-oxo-1-pyrrolidinyl}ethyl)thio]-1,3-thiazole-4-carboxylic acid (compound 34)

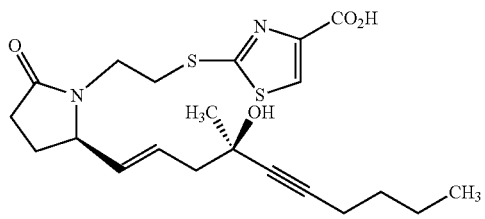 [SMILES: CCCCC#C[C@](C)(O)C/C=C/[C@H]1CCC(=O)N1CCSc1nc(C(=O)O)cs1]

To a solution of compound 33 (18.6 mg) in a solution of ethanol (0.44 mL)/dimethoxyethane (0.44 mL) was added dropwise 2N sodium hydroxide (0.067 mL), and the mixture was stirred overnight. To the reaction solution was added 1N hydrochloric acid (1.0 mL), and the mixture was extracted with ethyl acetate. The organic layer was washed with water and brine, dried over anhydrous magnesium sulfate, and concentrated to give the title compound (19.4 mg) having the following physical data was obtained.

TLC: Rf 0.45 (ethyl acetate:methanol:acetic acid=8:1:1);

NMR (CDCl$_3$): δ 0.90 (t, J=7.14 Hz, 3H), 1.12-1.57 (m, 7H), 1.64-1.88 (m, 1H), 2.01-2.65 (m, 7H), 3.00-4.93 (m, 2H), 3.23-3.44 (m, 2H), 3.44-3.60 (m, 1H), 3.74-3.96 (m, 1H), 4.05-4.23 (m, 1H), 5.42 (dd, J=15.19, 8.78 Hz, 1H), 5.64-6.10 (m, 1H), 8.08 (s, 1H).

Example 34 (1), Example 34 (2)

By the same procedure as described in Example 33→Example 34 using compound 24-2 or 2-[(2-{(2R)-2-[(1E)-4-hydroxy-4,7-dimethyl-1,7-octadien-1-yl]-5-oxo-1-pyrrolidinyl}ethyl)thio]-1,3-thiazole-4-carboxylic acid instead of compound 24-3, the following compounds were obtained.

Example 34 (1)

2-[(2-{(2R)-2-[(1E,4S)-4-hydroxy-4,7-dimethyl-1-octen-1-yl]-5-oxo-1-pyrrolidinyl}ethyl)thio]-1,3-thiazole-4-carboxylic acid (compound 34-1)

TLC: Rf 0.28 (ethyl acetate:methanol:acetic acid=8:1:1);

NMR (CDCl$_3$): δ 0.87 (t, J=6.59 Hz, 6H), 1.06-1.31 (m, 5H), 1.33-1.55 (m, 3H), 1.65-1.88 (m, 1H), 2.13-2.59 (m, 5H), 3.15-3.61 (m, 3H), 3.71-3.95 (m, 1H), 4.02-4.26 (m, 1H), 4.32-6.22 (m, 2H), 5.37 (dd, J=15.19, 8.97 Hz, 1H), 5.71-6.01 (m, 1H), 8.09 (s, 1H).

Example 34 (2)

2-[(2-{(2R)-2-[(1E,4S)-4-hydroxy-4,7-dimethyl-1,7-octadien-1-yl]-5-oxo-1-pyrrolidinyl}ethyl)thio]-1,3-thiazole-4-carboxylic acid (compound 34-2)

TLC: Rf 0.44 (ethyl acetate:methanol:acetic acid=5:1:1);

NMR (CDCl$_3$): δ 1.20 (s, 3H), 1.52-1.68 (m, 2H), 1.67-1.87 (m, 4H), 1.98-2.16 (m, 2H), 2.15-2.57 (m, 5H), 2.66-4.90 (m, 2H), 3.18-3.43 (m, 2H), 3.42-3.59 (m, 1H), 3.72-3.91 (m, 1H), 4.02-4.25 (m, 1H), 4.51-4.89 (m, 2H), 5.38 (dd, J=15.28, 9.06 Hz, 1H), 5.87 (dt, J=15.28, 7.50, 7.32 Hz, 1H), 8.09.

Biological Example

It was proved for example by the following experiments that an EP2 agonist which may have an EP3 agonistic effect has a nerve regenerative and/or protective activity.

The whole operation was carried out by using conventionally used methods based on the fundamental biological techniques. Additionally, for the purpose of evaluating the compounds of the present invention, improvement of measuring accuracy and/or improvement of measuring sensitivity was added to in the following manner. The following shows the experimental methods in detail.

(1) Measurement of EP2 Agonist and EP3 Agonist Activities
(1-1) Measurement of EP2 Agonist Activity (Measurement of Intracellular Cyclic AMP (cAMP) Concentration (cAMP Assay))

Cell Culture

A rat EP2 receptor forced expression cell (rEP2-CHO cell) was incubated in an incubator (5% CO$_2$) of 37° C. using Minimum Essential Medium Eagle (Sigma, M4526) to which 10% fetal bovine serum (FBS, JRH) and 1/100 total volume of Penicillin Streptomycin Glutamine (GIBCO, 10378-016) had been added. The cells which reached confluent were exfoliated using trypsin and suspended in a medium (MEM medium containing 10% FBS) to a density of 2.0×10$^5$ cells per ml. The thus prepared suspension was seeded into a 24 well plate to be 1.0×10$^5$ cells per well portions and incubated for 48 hours.

Compound Treatment

After the culturing, each well of the plate was washed with Minimum Essential Medium Alpha Medium (α-MEM medium; GIBCO, 41061-029 (500 μL)) and incubated for 10 minutes in an incubator (5% CO$_2$) of 37° C. by adding the α-MEM medium (500 μL) supplemented with diclofenac sodium (2 μmol/L). Thereafter, the medium was discarded. Assay buffer (1% bovine serum albumin (BSA)-containing α-MEM medium supplemented with diclofenac sodium (2 μmol/L) and isobutyl methyl xanthine (IBMX, 1 mmol/L)) was added to each well in the plate in 450 μL/well portions, and the culturing was again carried out for 10 minutes. The compound treatment was carried out by adding 50 μL of a compound solution (5% DMSO) which was prepared using the assay buffer to a 10 times concentration of its final concentration to each well of the plate and carrying out the culturing in an incubator (5% CO$_2$) at 37° C. for 10 minutes. After the compound treatment, the reaction was stopped by adding 10% trichloroacetic acid (500 μL) to each well, and the sample was frozen at −80° C.

Measurement of cAMP Concentration

The frozen sample was thawed and transferred to a micro centrifugation tube to be centrifuged (15,000 rpm, 4° C., 3 minutes). Then the supernatant (500 μL) was collected. To the supernatant, 500 μL of an extraction solution (chloroform solution containing tri-n-octylamine (0.5 mol/L)) was added and again centrifuged (15,000 rpm, 4° C., 3 minutes). Then the upper layer (100 μL) was collected. Using the upper layer as a sample, cAMP concentration was measured by a cAMP EIA system (cAMP Enzyme Immunoassay System, Amersham Biosciences).

Data Analysis

Activity strengths of respective compounds were compared by calculating their EC$_{50}$ values. The EC$_{50}$ value was calculated by regarding changed amount of the cAMP concentration when $PGE_2$ (1 μmol/l) was added instead of each compound as the maximum changed amount, and defining the value which gives half of the changed amount as the concentration of each compound.

(1-2) Measurement of EP3 Agonist Activity (Intracellular Calcium Concentration Real Time Imaging ($Ca^{2+}$ Assay))

Cell Culture

A rat EP3 receptor forced expression cell (rEP3-CHO cell) was incubated in an incubator (5% $CO_2$) of 37° C. using Minimum Essential Medium Eagle (Sigma, M4526) to which 10% fetal bovine serum (FBS, JRH) and 1/100 of total volume of Penicillin Streptomycin Glutamine (GIBCO, 10378-016) had been added. The cells which reached confluent were exfoliated using trypsin and suspended in a medium (MEM medium containing 10% FBS) to a density of $1.0 \times 10^5$ cells per ml. The thus prepared suspension was seeded into a FDSS-3000 (Hamamatsu Photonics)-corresponding 96 well plate in 100 μL per well portions and incubated for 48 hours.

Measurement of Intracellular Calcium Concentration

After the incubation, the culture fluid was removed from each well of the plate and a Fura2 loading buffer (10% FBS-containing MEM medium supplemented with Fura2-AM (5 μmol/L), HEPES (10 mmol/L), probenecid (2.5 mmol/L) and indometacin (20 μmol/L)) was added thereto, followed by incubating in an incubator (5% $CO_2$) of 37° C. Thereafter, the Fura2 loading buffer was removed. Each well was washed twice (100 μL×2) using a wash buffer (0.1% BSA-containing Hanks-HEPES buffer supplemented with probenecid (2.5 mmol/l) and indometacin (2 μmol/L)), 120 μL of an assay buffer (1% BSA-containing Hanks-HEPES buffer supplemented with probenecid (2.5 mmol/l) and indometacin (2 μmol/L)), and then it was incubated in an incubator (5% $CO_2$) of 37° C. for 30 minutes. The plate was further allowed to stand still for 15 minutes at room temperature in a dark and subjected to an intracellular calcium concentration real time imaging using FDSS-3000. Compound solution (5% DMSO) prepared to a 5 times concentration of its final concentration. After pre-incubation of the plate for 5.5 minutes, 30 μL thereof was directly added to each well. Measurement of the fluorescence intensity was continuously carried out for 3 minutes after addition of the compound.

Data Analysis

Activity intensity of each compound was compared by calculating their $EC_{50}$ values. The $EC_{50}$ value was calculated by regarding mean of the changed amount of calcium concentration when $PGE_2$ (100 nmol/L) was added instead of each compound as the maximum changed amount, and defining the value which gives half of the changed amount as the concentration of each compound. In this connection, the changed amount of calcium concentration was calculated by subtracting a ratio of "fluorescence intensity at 500 nm by an excitation light of 380 nm" to "fluorescence intensity at 500 nm by an excitation light of 340 nm" (Ex340/Ex380) during 10 to 20 seconds before the addition of the compound or medium from the peak value of Ex340/Ex380 during 3 minutes after the addition of the compound or medium.

Results

EP2 agonist and EP 3 agonist activities of compounds represented by the formula (I) were measured using the above method. For example, $EC_{50}$ values of the EP2 agonist and EP 3 agonist of the compound A were 0.016 μM and 0.099 μM, respectively, while $EC_{50}$ values of the EP2 agonist and EP 3 agonist of the compound 17 were 0.011 μM and 0.031 μM, respectively.

(2) Measurement of Cauda Equina Nerve Repair Acceleration Activity

A rat cauda equina nerve compression gait disturbance model was prepared by the method of Takenobu et al. (*J. Neurosci. Methods*, 104 (2), 191-198, 2002). Namely, a rat was anesthetized with pentobarbital sodium and, after shaving its dorsal region, fixed at abdominal position. After disinfection of the dorsal region with chlorhexidine gluconate (5% hibitane liquid; Sumitomo Pharmaceuticals), the waist was median-incised to expose the spinal column. After excision of the fifth lumbar gemmule, a silicon rubber of 1×4× 1.25 mm (height×length×width) was inserted into the fourth lumbar and sixth lumbar spinal canals from a small hole on the vertebral arch bored by a mini drill. For the purpose of avoiding infections, benzylpenicillin potassium (Crystalline Penicillin G Potassium Meiji; Meiji Seika Kaisha, Ltd.) was added dropwise to the incised part and intramuscularly injected into the thigh parts. The muscle and skin of the incised part were stitched with a surgical suture, and Iodine Tincture was applied to the stitched part. Animals of the sham operation group were prepared in accordance with the aforementioned method, but the insertion of silicon rubber was not carried out. After the operation, the compound A as a compound represented by the formula (I) and physiological saline were subjected to intravenous continuous administration (2 hours×twice/day, 2 weeks). A rat spinal cord specimen after completion of the administration of a substance to be tested was subjected to decalcification by an ion exchange resin method, and the cauda equina nerve of the fifth lumbar part was extracted to prepare a paraffin section of about 4 μm in thickness to carry out pathologic and histological inspection after staining with hematoxylin & eosin. Nerve fascicles in the section were classified in accordance with the following condition classification to calculate appearance rate of regeneration nerve fascicles.

| Condition | Description |
| --- | --- |
| Regeneration | Fascicles at the stage of Schwann tube formation. |
| Phagocytosis and elimination | Fascicles at the stage of phagocytosis and elimination of debris by Schwann cells and macrophages |
| Degeneration | Fascicles at the stage of axonal degeneration |
| Normal | Normal fascicles |

As a result, the compound A administration group showed significantly high appearance rate of regeneration nerve fascicles in comparison with the physiological saline administration group. Based on the above, it was suggested that the agent of the present invention has a nerve tissue regeneration activity.

(3) The Measurement of the Cauda Equina Blood Flow and the Blood Pressure 1.5 g/kg of urethane was administered intraperitoneally to the rat to be anesthetized, and the catheter (for measurement of blood pressure and ventricular rate) was placed in left carotid artery in supine position. The rat was reversed to prone position and the lumbar part was incised in the median line. The laminectomy was given to the fifth lumbar vertebra and the spinal cord (cauda equina) was exposed. The cauda equina blood flow was measured by the laser-Doppler flowmetry (OMEGAFLD FLO-NI and ADVANCE LASER FLOWMETER ALF21N, OMEGA WAVE Inc.) through a noncontact probe (ST-N type, OMEGA WAVE Inc.) and recorded with LINEARCORDER (Graphtech). The systemic blood pressure and the ventricular rate were measured from a left carotid artery with amplifier for the pressure measurement (GOULD) through a pressure transducer and recorded with LINEARCORDER (Graphtech). After confirming each parameter of blood pressure, ventricular rate and blood flow was stabilized, the test compound was administrated by continuous infusion through the winged needle placed in caudal vein for 30 minutes. It observed until 30 minutes after the administration and the increase rate of the cauda equina blood flow was calculated.

The increase rate of the cauda equina blood flow (%)=(B−A)/A×100

A: the cauda equina blood flow before the administration of the test compound

B: the cauda equina blood flow after the administration of the test compound

As a result, the compounds which are represented by formula (I) increased the cauda equina blood flow although they had weak blood pressure-lowering effect. For instance, Compound 17 of the compounds which are represented by formula (I) increased 33% of the cauda equina blood flow, while it decreased only 5 mmHg of the blood pressure.

FORMULATION EXAMPLE

Formulation Example 1

Compound 17 (5.0 g), carboxymethyl cellulose calcium (20 g), magnesium stearate (10 g) and microcrystalline cellulose (920 g) were admixed in a conventional method and punched out to obtain 10,000 tablets each containing 0.5 mg of the active ingredient.

Formulation Example 2

Compound 17 (2.0 g), mannitol (500 g) and distilled water (10 L) were admixed in a conventional method, and the solution was sterilized in a conventional method, placed at 1 mL into vials and freeze-dried in a conventional method to thereby obtain 10,000 vials each containing 0.2 mg of the active ingredient.

INDUSTRIAL APPLICABILITY

An EP2 agonist which may have an EP3 agonistic effect has an effect of regenerating and/or protecting nerves, and is therefore useful as a therapy such as a disease of the peripheral nervous system. An EP2 agonist having an EP3 agonistic effect is useful as a safe and effective agent for the regeneration and/or protection of nerves which has little influence on the circulatory system.

The invention claimed is:

1. A compound represented by formula (I-3):

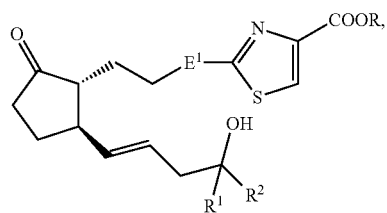

(I-3)

wherein $E^1$ is oxygen or optionally oxidized sulfur, R is hydrogen or C1-8 aliphatic hydrocarbon group, ⋯ is α-configuration, ∕ is β-configuration, $R^1$ is hydrogen or C1-4 aliphatic hydrocarbon group, $R^2$ is hydrocarbon group which may have a substituent(s), with the proviso that $R^2$ is not C2-8 alkenyl which may have 1 to 5 halogen atom(s), excluding 2-[(2-{(1R,2R)-2-[(1E,3S,5S)-3-hydroxy-5-methyl-1-nonenyl]-5-oxocyclopentyl}ethyl)sulfanyl]-1,3-thiazole-4-carboxylic acid, 2-[(2-{(1R,2R)-2-[(1E,3R)-3-hydroxy-4,4-dimethyl-1-octenyl]-5-oxocyclopentyl}ethyl)sulfanyl]-1,3-thiazole-4-carboxylic acid, 2-[(2-{(1R,2R)-2-[(1E)-4-hydroxy-4-methyl-1-nonenyl]-5-oxocyclopentyl}ethyl)sulfanyl]-1,3-thiazole-4-carboxylic acid, 2-[(2-{(1R,2R)-2-[(1E)-5-cyclohexyl-4-hydroxy-4-methyl-1-pentenyl]-5-oxocyclopentyl}ethyl)sulfanyl]-1,3-thiazole-4-carboxylic acid and 2-[(2-{(1R,2R)-2-[(1E)-5-cyclohexyl-4-hydroxy-4-methyl-1-pentenyl]-5-oxocyclopentyl}ethyl)sulfonyl]-1,3-thiazole-4-carboxylic acid, a salt thereof, an N-oxide thereof, an S-oxide thereof, or a cyclodextrin clathrate thereof.

2. The compound according to claim 1, wherein $R^1$ is hydrogen or C1-4 alkyl group, $R^2$ is C1-8 aliphatic hydrocarbon group which may have a substituent(s), or (C3-8 cycloalkyl)-(C1-4 aliphatic hydrocarbon) group which may have a substituent(s).

3. The compound according to claim 1, which is selected from the group consisting of Ethyl 2-[(2-{(1R,2R)-2-[(1E,4S)-5-cyclohexyl-4-hydroxy-4-methyl-1-pentenyl]-5-oxocyclopentyl}ethyl)thio]-1,3-thiazole-4-carboxylate, 2-[(2-{(1R,2R)-2-[(1E,4S)-5-cyclohexyl-4-hydroxy-4-methyl-1-penten-1-yl]-5-oxocyclopentyl}ethyl)thio]-1,3-thiazole-4-carboxylic acid, 2-[(2-{(1R,2R)-2-[(1E,4S)-4-hydroxy-4-methyl-1-nonen-1-yl]-5-oxocyclopentyl}ethyl)thio]-1,3-thiazole-4-carboxylic acid, 2-[(2-{(1R,5R)-2-oxo-5-[(1E)-8,8,8-trifluoro-4-hydroxy-4-methyl-1-octenyl]cyclopentyl}ethyl)thio]-1,3-thiazole-4-carboxylic acid, 2-[(2-{(1R,2R)-2-[(1E)-5-cyclopentyl-4-hydroxy-4-methyl-1-pentenyl]-5-oxocyclopentyl}ethyl)thio]-1,3-thiazole-4-carboxylic acid, 2-[(2-{(1R,2R)-2-[(1E)-8-fluoro-4-hydroxy-4-methyl-1-octen-1-yl]-5-oxocyclopentyl}ethyl)thio]-1,3-thiazole-4-carboxylic acid, 2-[(2-{(1R,2R)-2-[(1E)-4-hydroxy-4,8-dimethyl-1-nonen-1-yl]-5-oxocyclopentyl}ethyl)thio]-1,3-thiazole-4-carboxylic acid, 2-[(2-{(1R,2R)-2-[(1E)-6-cyclobutyl-4-hydroxy-4-methyl-1-hexen-1-yl]-5-oxocyclo pentyl}ethyl)thio]-1,3-thiazole-4-carboxylic acid, 2-[(2-{(1R,2R)-2-[(1E)-4-hydroxy-4,7-dimethyl-1-octen-1-yl]-5-oxocyclopentyl}ethyl)thio]-1,3-thiazole-4-carboxylic acid, 2-[(2-{(1R,2R)-2-[(1E)-6-cyclopropyl-4-hydroxy-4-methyl-1-hexen-1-yl]-5-oxo cyclopentyl}ethyl)thio]-1,3-thiazole-4-carboxylic acid, 2-[(2-{(1R,2R)-2-[(1E)-4-hydroxy-7-methoxy-4-methyl-1-hepten-1-yl]-5-oxocyclo pentyl}ethyl)thio]-1,3-thiazole-4-carboxylic acid, 2-[(2-{(1R,2R)-2-[(1E)-4-hydroxy-4-methyl-1-octen-5-yn-1-yl]-5-oxocyclopentyl}ethyl)thio]-1,3-thiazole-4-carboxylic acid, 2-[(2-{(1R,2R)-2-[(1E)-9-fluoro-4-hydroxy-4-methyl-1-nonen-1-yl]-5-oxocyclopentyl}ethyl)thio]-1,3-thiazole-4-carboxylic acid, 2-[(2-{(1R,2R)-2-[(1E)-4-hydroxy-4-methyl-1-nonen-7-yn-1-yl]-5-oxocyclopentyl}ethyl)thio]-1,3-thiazole-4-carboxylic acid, 2-[(2-{(1R,2R)-2-[(1E)-10-fluoro-4-hydroxy-4-methyl-1-decen-1-yl]-5-oxocyclo pentyl}ethyl)thio]-1,3-thiazole-4-carboxylic acid, 2-[(2-{(1R,2R)-2-[(1E)-4-hydroxy-4-methyl-1-octen-1-yl]-5-oxocyclopentyl}ethyl)thio]-1,3-thiazole-4-carboxylic acid, 2-[(2-{(1R,2R)-2-[(1E)-5-cyclobutyl-4-hydroxy-4-methyl-1-penten-1-yl]-5-oxocyclopentyl}ethyl)thio]-1,3-thiazole-4-carboxylic acid, 2-[(2-{(1R,2R)-2-[(1E)-4-hydroxy-4-methyl-1-decen-1-yl]-5-oxocyclopentyl}ethyl)thio]-1,3-thiazole-4-carboxylic acid, 2-[(2-{(1R,2R)-2-[(1E)-6-cyclobutyl-4-hydroxy-1-hexen-1-yl]-5-oxocyclopentyl}ethyl)thio]-1,3-thiazole-4-carboxylic acid, 2-[(2-{(1R,2R)-2-[(1E)-4-hydroxy-1-nonen-5-yn-1-yl]-5-oxocyclopentyl}ethyl)thio]-1,3-thiazole-4-carboxylic acid, 2-[(2-{(1R,2R)-2-[(1E,4R)-5-cyclohexyl-4-hydroxy-4-methyl-1-penten-1-yl]-5-oxocyclopentyl}ethyl)thio]-1,3-thiazole-4-carboxylic acid, 2-[(2-{(1R,2R)-2-[(1E,4R)-4-hydroxy-4-methyl-1-nonen-1-yl]-5-oxocyclopentyl}ethyl)thio]-1,3-thiazole-4-carboxylic acid, 2-[(2-{(1R,2R)-2-[(1E,4R)-4-hydroxy-4,8-dimethyl-1-nonen-5-yn-1-yl]-5-oxocyclopentyl}ethyl)thio]-1,3-thiazole-4-carboxylic acid, 2-[(2-{(1R,2R)-2-[(1E,4S)-4-hydroxy-4,8-dimethyl-1-nonen-5-yn-1-yl]-5-oxocyclopentyl}ethyl)thio]-1,3-thiazole-4-carboxylic acid, 2-[(2-{(1R,2R)-2-[(1E,4S)-4-hydroxy-4,7-dimethyl-1-octen-1-yl]-5-oxocyclopentyl}ethyl)thio]-1,3-thiazole-4-carboxylic acid, 2-[(2-{(1R,2R)-2-[(1E,4R)-4-hydroxy-4,7-dimethyl-1-octen-1-yl]-5-oxocyclopentyl}ethyl)thio]-1,3-thiazole-4-carboxylic acid, 2-[(2-{(1R,2R)-2-[(1E,4S)-6-cyclobutyl-4-hydroxy-4-methyl-1-hexen-1-yl]-5-oxocyclopentyl}ethyl)thio]-1,3-thiazole-4-carboxylic acid, 2-[(2-{(1R,2R)-2-[(1E,4R)-6-cyclobutyl-4-hydroxy-4-methyl-1-hexen-1-yl]-5-oxocyclopentyl}ethyl)thio]-1,3-thiazole-4-carboxylic acid, 2-[(2-{(1R,2R)-2-[(1E,4R)-4-hydroxy-4-methyl-1-decen-5-yn-1-yl]-5-oxocyclopentyl}ethyl)thio]-1,3-thiazole-4-carboxylic acid, 2-[(2-{(1R,2R)-2-[(1E,4S)-4-hydroxy-4-methyl-1-decen-5-yn-1-yl]-5-oxocyclopentyl}ethyl)thio]-1,3-thiazole-4-carboxylic acid, 2-[(2-{(1R,2R)-2-[(1E,4S)-6-cyclopentyl-4-hydroxy-4-methyl-1-hexen-1-yl]-5-oxocyclopentyl}ethyl)thio]-1,3-thiazole-4-carboxylic acid, 2-[(2-{(1R,5R)-2-oxo-5-[(1E,4S)-9,9,9-trifluoro-4-hydroxy-4-methyl-1-nonen-1-yl]cyclopentyl}ethyl)thio]-1,3-thiazole-4-carboxylic acid, 2-[(2-{(1R,2R)-2-[(1E,4S,7S)-4-hydroxy-4,7-dimethyl-1-nonen-1-yl]-5-oxocyclopentyl}ethyl)thio]-1,3-thiazole-4-carboxylic acid, 2-[(2-{(1R,5R)-2-oxo-5-[(1E,4S)-7,7,7-trifluoro-4-hydroxy-4-methyl-1-hepten-1-yl]cyclopentyl}ethyl)thio]-1,3-thiazole-4-carboxylic acid, 2-[(2-{(1R,2R)-2-[(1E,4S)-6-cyclobutyl-4-hydroxy-1-hexen-1-yl]-5-oxocyclopentyl}ethyl)thio]-1,3-thiazole-4-carboxylic acid, 2-[(2-{(1R,5R)-2-oxo-5-[(1E,4S)-7,7,7-trifluoro-4-hydroxy-1-hepten-1-yl]cyclopentyl}ethyl)thio]-1,3-thiazole-4-carboxylic acid, and 2-[(2-{(1R,2R)-2-[(1E,4S,7S)-4-hydroxy-7-methyl-1-nonen-1-yl]-5-oxocyclopentyl}ethyl)thio]-1,3-thiazole-4-carboxylic acid.

4. A composition comprising the compound which is represented by formula (I-3) according to claim 1, the salt thereof, the N-oxide thereof, the S-oxide thereof, or the cyclodextrin clathrate thereof.

5. The compound according to claim 1, which is represented by formula (I-4):

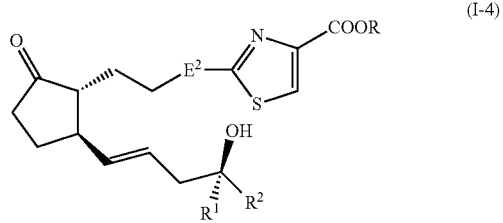

(I-4)

wherein E² is optionally oxidized sulfur, the other symbols have the same meanings as those described in the claim 1.

* * * * *